United States Patent
Mamonkin et al.

(10) Patent No.: US 10,786,549 B2
(45) Date of Patent: Sep. 29, 2020

(54) CD5 CHIMERIC ANTIGEN RECEPTOR FOR ADOPTIVE T CELL THERAPY

(71) Applicant: Baylor College of Medicine, Houston, TX (US)

(72) Inventors: Maksim Mamonkin, Pearland, TX (US); Malcolm K. Brenner, Bellaire, TX (US)

(73) Assignee: Baylor College of Medicine, Houston, TX (US)

( * ) Notice: Subject to any disclaimer, the term of this patent is extended or adjusted under 35 U.S.C. 154(b) by 48 days.

(21) Appl. No.: 15/568,702

(22) PCT Filed: Apr. 22, 2016

(86) PCT No.: PCT/US2016/029014
§ 371 (c)(1),
(2) Date: Oct. 23, 2017

(87) PCT Pub. No.: WO2016/172606
PCT Pub. Date: Oct. 27, 2016

(65) Prior Publication Data
US 2018/0104308 A1  Apr. 19, 2018

Related U.S. Application Data

(60) Provisional application No. 62/151,609, filed on Apr. 23, 2015.

(51) Int. Cl.
| | |
|---|---|
| *A61K 38/17* | (2006.01) |
| *A61K 45/06* | (2006.01) |
| *C07K 14/725* | (2006.01) |
| *C07K 14/705* | (2006.01) |
| *C07K 16/28* | (2006.01) |
| *C12N 5/0783* | (2010.01) |
| *A61K 35/17* | (2015.01) |
| *A61P 35/02* | (2006.01) |
| *A61K 39/395* | (2006.01) |
| *C07K 14/715* | (2006.01) |
| *C07K 16/30* | (2006.01) |

(52) U.S. Cl.
CPC .......... *A61K 38/1774* (2013.01); *A61K 35/17* (2013.01); *A61K 39/395* (2013.01); *A61K 45/06* (2013.01); *A61P 35/02* (2018.01); *C07K 14/7051* (2013.01); *C07K 14/70521* (2013.01); *C07K 14/715* (2013.01); *C07K 16/2896* (2013.01); *C07K 16/30* (2013.01); *C12N 5/0636* (2013.01); *C07K 2317/622* (2013.01); *C07K 2317/92* (2013.01); *C07K 2317/94* (2013.01); *C07K 2319/03* (2013.01)

(58) Field of Classification Search
None
See application file for complete search history.

(56) References Cited

U.S. PATENT DOCUMENTS

2011/0250203 A1  10/2011  Klitgaard et al.

FOREIGN PATENT DOCUMENTS

| | | |
|---|---|---|
| WO | 2013/123061 A1 | 8/2013 |
| WO | 2014/055668 A1 | 4/2014 |
| WO | 2015/075468 A1 | 5/2015 |
| WO | 2016/138491 A1 | 9/2016 |
| WO | 2017/112877 A1 | 6/2017 |

OTHER PUBLICATIONS

Rogers et al. (Vet. Immunol. Immunopathology 2002 85: 233-239), (Year: 2002).*
Cordoba et al., "Chimeric Antigen Receptor Logical AND Gate Based on CD45/CD148 Phosphatases" Molecular Therapy, vol. 22, No. Suppl. 1, p. S59, May 1, 2014.
Antin et al, "Selective depletion of bone marrow T lymphocytes with anti-CD5 monoclonal antibodies: effective prophylazis for graft-versus-hose disease in patients with hematologic malignancies", Blood, 1991, vol. 78, No. 8, pp. 2139-2149.
Antin et al, "B lymphocyte reconstitution after human bone marrow transplantation. Leu-1antigen defines a distinct population of B lymphocytes", J Clin Invest, 1987, vol. 80, No. 2, pp. 325-332.
Mamonkin et al, "A T-cell-directed chimeric antigen receptor for the selective treatment of T-cell malignancies", Blood Epub Jun. 8, 2015, vol. 126, No. 8, pp. 983-992.

* cited by examiner

*Primary Examiner* — Peter J Reddig
(74) *Attorney, Agent, or Firm* — Norton Rose Fulbright US LLP

(57) ABSTRACT

Embodiments of the disclosure include methods and compositions related to immunotherapy that targets CD5. In particular embodiments, immune cells engineered to comprise a chimeric antigen receptor (CAR) that targets CD5 are contemplated, and uses thereof. In particular embodiments, the immune cells expressing the CAR do not commit fratricide to any great extent against T cells that express CD5 and which are endogenous to an individual receiving the immune cells.

19 Claims, 60 Drawing Sheets
Specification includes a Sequence Listing.

CD5 CHIMERIC ANTIGEN RECEPTOR FOR ADOPTIVE T CELL THERAPY

This application is a national phase application under 35 U.S.C. § 371 that claims priority to International Application No. PCT/US16/29014 filed Apr. 22, 2016 which claims priority to U.S. Provisional Patent Application Ser. No. 62/151,609, filed Apr. 23, 2015, all of which are incorporated by reference herein in their entirety.

INCORPORATION OF SEQUENCE LISTING

The instant application contains a Sequence Listing, named "Sequence_Listing.txt" (14,300 bytes), created Oct. 23, 2017, which has been submitted electronically in ASCII format and is hereby incorporated by reference in its entirety.

TECHNICAL FIELD

The present disclosure concerns at least the fields of immunology, cell biology, molecular biology, and medicine, including cancer medicine.

BACKGROUND

Acute Lymphoblastic Leukemia (ALL) is the most common cancer in pediatric patients. T-lineage Acute Lymphoblastic Leukemia (T-ALL) accounts for 15% of ALL cases in children and 20-25% in adults. Cure rates for adult T-ALL cases are low (20-40%) and there is a high risk of incurable relapse.

Chimeric Antigen Receptors (CAR) are a promising and effective technology for adoptive T cell therapy, including that of hematologic malignancies of B-cell origin such as acute lymphoblastic leukemia (B-ALL) and chronic lymphocytic leukemia (B-CLL). However, using CAR T cells against T-cell malignancies is frequently challenging because of shared expression of most surface antigens between normal and malignant T cells, which would lead to T-cell fratricide. Currently, there are no adoptive cell therapy options for T-cell leukemia.

CD5 is a transmembrane receptor highly expressed in ~85% of T-ALLs and ~75% of peripheral T-cell lymphomas. In addition, CD5 is often expressed in mantle cell lymphoma, B-CLL and hairy cell leukemia cells. In normal cells, expression of CD5 is restricted to mature T cells and a subset of B cells, making CD5 a potentially attractive tumor antigen if the issue of fratricide can be addressed.

The present disclosure satisfies a long-felt need in the art to provide effective therapy for CD5-expressing cancers without harming normal T cells.

BRIEF SUMMARY

The present embodiments are directed to methods and/or compositions for the treatment of cancer. In particular cases, the disclosure concerns methods and/or compositions for the treatment of cancers in which the cancer cells comprise CD5, for example as a tumor antigen. Although in certain aspects the cancer may be of any kind, in certain embodiments, the cancer is a liquid tumor, e.g. blood cancer, such as leukemia or lymphoma. In other embodiments the cancer is a solid tumor. In examples wherein the cancer is leukemia, in particular embodiments the leukemia is of a T-lineage. Examples of solid tumors include breast cancer, thymus cancer, or CD5+ B-cell malignancies, such as B-cell chronic lymphocytic leukemia (B-CLL), mantle cell lymphoma and hairy cell leukemia. The individual being treated may be of any gender or age, including an infant, child, adolescent, or adult.

In one aspect, provided herein are methods and/or compositions that enable T cells to effectively target and eliminate CD5-expressing T cells, NKT cells and B cells (including, for example, T-ALL cells, T cell lymphoma, and cutaneous T cell lymphomas, including Sezary syndrome, as well as CD5+ NKT cell lymphomas and CD5+ B-CLL), while displaying only limited or no self-toxicity. Embodiments of the disclosure encompass immune cells that express a CD5-targeting chimeric antigen receptor (CAR). In certain embodiments, the CD5 CAR comprises an antibody, e.g. a scFv specific for CD5.

Embodiments of the disclosure concern a method to target cells expressing CD5, e.g., liquid tumor cells or solid tumor cells, with immune cells, comprising genetically engineering the cells to express a CD5-specific CAR, and contacting the tumor cells with the immune cells, e.g., such that the immune cells kill the tumor cells. Methods and compositions are applicable to the immunotherapy of a broad range of diseases that are CD5 positive. Described herein are engineered T cells that express CD5-specific CARs. In certain embodiments, CD5-specific CARs can be expressed in other immune cells, including but not limited to, NK cells, NKT cells, γδ T cells, or T cells that recognize specific antigens (e.g., viral or other tumor associated antigens) through their native T-cell receptor. In specific embodiments, CD5-specific CARs transmit signals to activate immune cells through CD3 zeta, CD28, and/or 4-1BB pathways, although the intracellular CAR domain could be readily modified to include other signaling moieties.

The CD5-specific CAR provided herein may include one or more costimulatory endodomains, such as CD28, CD27, 4-1BB, OX40, ICOS (CD278) or a combination thereof. In a specific embodiment, the CD5 CAR does not comprise a 4-1BB costimulatory domain. The CAR may include one or more transmembrane domains, such as one selected from the group consisting of CD3-zeta, CD28, CD8a, CD4, or a combination thereof. In some embodiments, the immune cells are one of T cells, NK cells, dendritic cells, or a mixture thereof. In certain aspects, T cells redirected against CD5 control the growth of CD5-expressing cells, including cancer cells, either in vitro or in vivo, e.g., in an individual having a cancer comprising tumor cells that express CD5.

In particular embodiments, one can modify the CD5 CAR, such as to eliminate cellular FcγR interactions to improve T cell persistence and antitumor responses.

In specific embodiments, the immune cells of the disclosure express one or more other entitities besides the CD5 CAR that facilitate a therapeutic activity for the cells. As examples, the immune cells may also express an additional CAR, a cytokine, a cytokine receptor, a chimeric cytokine receptor, or a combination thereof. In embodiments wherein the cells express a CAR other than the CD5 CAR, the other CAR may be an activating CAR or an inhibitory CAR. Inhibitory CARs have the exodomain fused to one or more inhibitory signaling domains (instead of activating endodomains), including PD-1, CTLA4, KIR2/KIR3, LIR, BTLA, FCRL, and CEACAM, for example. The exodomain can target molecules that distinguish normal cells from malignant, such as components of T cell receptor, components of B cell receptor, CD3, heavy chain of immunoglobulin, light chain of immunoglobulin (either kappa or lambda), CD4, CD8 and others.

In one embodiment, there is a method of inhibiting proliferation and/or activity of CD5-positive cells in an individual, comprising the step of contacting the cells with a therapeutically effective amount of immune cells that express a chimeric antigen receptor (CAR) that targets CD5. In specific embodiments, the cells that are contacted are cancer cells. The CD5-positive cells are normal cells or are cancer cells, in particular embodiments, including the CD5-positive normal cells being B cells. The CD5-positive cancer cells may be T cells, B cells, breast cancer cells, or thymus cancer cells, for example.

In certain embodiments, contacting of the CD5-positive cells with the CD5 CAR-specific immune cells is performed in vitro and may be performed in cell culture. In specific embodiments, the contacting is performed in vivo, and the immune cells are cells from an individual. In cases where the contact occurs in vivo, in specific embodiments the immune cells are T cells from an individual, and they may be autologous to the individual or allogeneic to the individual, in certain embodiments. The immune cells are T cells, NK cells, dendritic cells, or a mixture thereof, in particular embodiments, and when the immune cells are T cells, they may be CD4+ T cells, CD8+ T cells, or Treg cells.

In particular embodiments, the CAR comprises an extracellular domain that comprises an anti-CD5 scFv, and in specific embodiments the CAR comprises an extracellular domain that comprises CD72 (Lyb-2). In certain embodiments, the CAR comprises one or more additional scFvs to the anti-CD5 scFv, such as when the additional scFv targets CD19, CD20, CD22, Kappa or light chain, Glypican-3, CD30, CD33, CD123, CD38, ROR1, ErbB2, ErbB3/4, EGFR vIII, carcinoembryonic antigen, EGP2, EGP40, mesothelin, TAG72, PSMA, NKG2D ligands, B7-H6, IL-13 receptor α2, IL-11 receptor R α, MUC1, MUC16, CA9, GD2, GD3, HMW-MAA, CD171, Lewis Y, G250/CAIX, HLA-AI MAGE A1, HLA-A2 NY-ESO-1, PSC1, folate receptor-α, CD44v7/8, 8H9, NCAM, VEGF receptors, 5T4, Fetal AchR, NKG2D ligands, CD44v6 or CD7, for example. In particular embodiments, the CAR comprises a transmembrane domain selected from the group consisting of CD3-zeta, CD28, CD8a, CD4, or a combination thereof. In specific embodiments, the CAR comprises a co-stimulatory molecule endodomain selected from the group consisting of CD2, CD28, CD27, 4-1BB, OX40, ICOS, (CD278), CD30, HVEM (Hepatitis Virus Entry Mediator), CD40, LFA-1 (CD11a/CD18), ICAM-1, and a combination of two or more thereof. In a specific embodiment, the CAR comprises a co-stimulatory molecule endodomain that is not 4-1BB. In certain embodiments, the immune cells provided herein may further express an additional CAR (e.g., directed to a target other than CD5), a cytokine, a cytokine receptor, a chimeric cytokine receptor, or a combination thereof. In certain embodiments, the additional CAR is an activating CAR or an inhibitory CAR. In another specific embodiment, the chimeric antigen receptor does not comprise a 4-1BB costimulatory domain.

In particular embodiments, the individual has received, is receiving, or will receive an additional cancer treatment, such as one that comprises chemotherapy, immunotherapy, radiation, surgery, hormone therapy, or a combination thereof.

In particular embodiments of methods of the disclosure, the CD5-positive cells being targeted are early normal T cells and the individual has an autoimmunity disease or is in need of a transplant. In other embodiments, the CD5-positive cells are normal early T cells and the individual has graft-versus-host disease.

In one embodiments, the immune cells of the disclosure harbor a polynucleotide that encodes the CD5-specific CAR. In a specific embodiment, the polynucleotide further comprises a suicide gene, a cytokine, an additional CAR, a cytokine receptor, or a chimeric cytokine receptor. In some cases, the cells that are contacted are $CD62L^{high}$ T cells.

In one embodiment there is as a composition of matter immune cells that express a chimeric antigen receptor (CAR) that targets CD5. In specific embodiments, the cells are T cells, NK cells, dendritic cells, or a mixture thereof. In a specific embodiment, the CAR is expressed from a recombinant polynucleotide, and in some cases the polynucleotide further comprises a suicide gene, a cytokine, an additional CAR, a cytokine receptor, or a chimeric cytokine receptor. In specific embodiments, the immune cells comprise a polynucleotide that comprises a suicide gene, a cytokine, an additional CAR, a cytokine receptor, or a chimeric cytokine receptor, wherein said polynucleotide is a different molecule than the polynucleotide that expresses the CAR that targets CD5. In particular embodiments, the CAR comprises a co-stimulatory molecule endodomain selected from the group consisting of CD2, CD28, CD27, 4-1BB, (CD137), OX40, ICOS, (CD278), CD30, HVEM, CD40, LFA-1 (CD11a/CD18), ICAM-1, and a combination of two or more thereof. In specific embodiments, the CAR comprises a co-stimulatory molecule endodomain that is not 4-1BB. In some embodiments, the additional CAR is an activating CAR or an inhibitory CAR.

In some embodiments, CD5 CAR-specific cells, such as CD5 CAR-specific immune cells, are utilized for methods that are not for targeting cancer cells. In specific embodiments, the CD5-specific CAR is utilized to target non-cancerous cells, such as normal lymphocytes, for example. Such targeting is useful in diseases or conditions in which suppression of the immune system is desired, such as with autoimmune diseases and following organ, cell (such as stem cells), and/or tissue transplant. In specific embodiments, autoimmune diseases mediated by CD5-positive cells, such as CD5-positive lymphocytes, are treated using therapeutically effective amounts of CD5 CAR-specific cells. Examples of autoimmune diseases that are initiated and/or depend on CD5+ T cells include (but are not limited to) multiple sclerosis, type I diabetes, rheumatoid arthritis and systemic lupus erythematosus (SLE). In addition, graft-versus-host disease may be mediated by alloreactive CD5+ T cells.

In some embodiments, CD5 CAR-specific cells, such as CD5 CAR-specific immune cells, are utilized for methods that are not for targeting cancer cells. In specific embodiments, the CD5-specific CAR is utilized to target non-cancerous cells, such as normal lymphocytes, for example. Such targeting is useful in diseases or conditions in which suppression of the immune system is desired, such as with autoimmune diseases and following organ, cell (such as stem cells), and/or tissue transplant. In specific embodiments, autoimmune diseases mediated by CD5-positive cells, such as CD5-positive lymphocytes, are treated using therapeutically effective amounts of CD5 CAR-specific cells. Examples of autoimmune diseases that are initiated and/or depend on CD5+ T cells include (but are not limited to) multiple sclerosis, type I diabetes, rheumatoid arthritis and systemic lupus erythematosus (SLE). In addition, graft-versus-host disease may be mediated by alloreactive CD5+ T cells.

Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which:

(FIG. 1A) Schematic structure of CD5 CAR and transduction efficiency of primary activated T cells. (FIG. 1B) Expansion of activated T cells transduced with either control CAR (Ctrl CAR) or CD5 CAR. Data denote mean±SD from 4 donors. (FIG. 1C) Surface expression of CD5 on non-transduced (NT) T cells or T cells transduced with control (Ctrl CAR) or CD5 CAR at 7 d post-activation. (FIG. 1D) Relative expression of CD5 mRNA in non-transduced (NT) activated T cells or T cells transduced with CD5 CAR at 7 days post-stimulation.

(FIG. 2A) Autologous GFP+ T cells were mixed with T cells transduced with control (Ctrl) CAR, truncated CD5 CAR (ΔCD5 CAR, without intracellular signaling domains) or full length CD5 CAR at 1:2 E:T ratio and co-cultured for 7 days. Numbers in dot plots denote cell counts of gated GFP+ autologous T cells per well at indicated time points. Right-hand graph summarizes data from 4 donors±SD. (FIG. 2B) Phenotype of activated T cells 10 days after transduction with control CAR or CD5 CAR. Naïve T cells ($T_{NAIVE}$, CD45RA$^+$ CD62L$^+$), central memory ($T_{CM}$, CD45RA$^-$ CD62L$^+$), effector and effector-memory ($T_{EFF}/T_{EM}$, CD45RA$^-$ CD62L$^+$) and $T_{EMRA}$ (CD45RA$^+$ CD62L$^-$) subsets are shown as the mean of 4 donors. (FIG. 2C) Phenotype of autologous GFP+ T cells after co-culture with control CAR- (Ctrl) or CD5 CAR-transduced T cells for 24 h. Representative dot plots with gating strategy (left) and mean data from 4 donors (right) are shown. (FIG. 2D) Autologous GFP+ T cells were co-cultured with control CAR T or CD5 CAR T cells for 72 h and purified by cell sorting. Frequency of T cells specific for CMV, EBV and AdV among sorted cells was measured by IFNγ ELISpot.

(FIG. 3A) Cytotoxicity of CD19 CAR- and CD5 CAR-transduced T cells against T-ALL and T lymphoma cell lines was assessed in a 5 hr Cr release assay. CD19$^+$ CD5$^-$ Raji cells were used as a negative control for CD5 CAR and positive control for CD19 CAR T cells. (FIG. 3B) Production of IFNg and TNFa by CD4$^+$ and CD8$^+$ T cells transduced with CD19 CAR or CD5 CAR was measured by intracellular cytokine staining. Bar graphs show mean±SD from 3 donors. (FIG. 3C) Long-term co-culture of CAR T cells with GFP+ target cell lines Jurkat, CCRF and MOLT4 at an initial E:T ratio 1:4. Numbers in dot plots denote percentage of target GFP$^+$ cells at indicated time points. (FIG. 3D) Sequential killing of GFP$^+$ Jurkat cells by CD5 CAR T cells. Graph indicates number of target Jurkat cells per well at the beginning and the end of each cycle of cell killing. Data from 3 individual donors are shown.

(FIG. 4A) Inhibition of cytotoxicity of CD5 CAR T cells against autologous T cells and Jurkat cells by blocking either FasL (BFA+aFasL), perforin (CMA+EGTA) or both pathways. Cell death was measured by Annexin V after 2 h of co-culture. (FIG. 4B) Expression of PI-9 protein in CD5 CAR T cells and malignant T cell lines was measured by intracellular staining and flow cytometry. Bar graphs show MFI of PI-9. (FIG. 4C) Expression of cathepsin B transcript in CD5 CAR T cells and target cell lines was measured by qPCR. (FIG. 4D) Levels of bcl-2 transcript in CD5 CAR T cells and target cell lines. (FIG. 4E) Protein expression of Bcl-2 was measured by intracellular staining and flow cytometry. (FIG. 4F) Bid expression in CD5 CAR T cells and target cell lines was measured by qPCR. Error bars denote SD for 3 different T cell donors.

(FIG. 5A) Production of IFNg upon co-culture with different primary T-ALL samples was assessed by intracellular cytokine staining. Numbers indicate percent or CAR+ T cells positive for IFNg. (FIG. 5B) Production of IFNg, TNFa and expression of CD107a by CD5 CAR T cells upon mixing with thawed T-ALL blasts from 2 patients (T-ALL #295 and #315). Bar graphs depict frequency of cytokine-producing CD4+ and CD8+ T cells as average±SEM from 4 donors. (FIG. 5C) Cytotoxicity of CD5 CAR T cells against fresh primary T-ALL blasts isolated from PBMC of a T-ALL patient #394 was measured in a 5 h Cr release assay. Protein expression of PI-9 (FIG. 5D) and Bcl-2 (FIG. 5E) in T-ALL blasts from donor #394 was measured by intracellular staining and flow cytometry. Bar graphs depict corresponding MFI compared to CD5 CAR T cells (mean±SD from 3 donors) and Jurkat T-ALL cell line.

(FIG. 6A) Jurkat-FFluc cells ($3\times10^6$ per mouse) were injected i.v. followed by injection of CAR T cells ($10\times10^6$ per mouse) i.v. on days 3 and 6 post-implantation. Tumor burden was assessed by IVIS imaging at indicated time points. (FIG. 6B) Kaplan-Meier survival curve; mice were euthanized after developing hind limb paralysis. (FIG. 6C) Eradication of systemic disease by CD5 CAR T cells. Mice were engrafted with Jurkat-FFluc cells, which established systemic disease by day 6. (FIG. 6D) Total luminescence from Jurkat cells recorded on day 6 (prior to CAR T cell injection) and day 12. (FIG. 6E) CCRF-CEM-FFluc cells ($1\times10^6$ per mouse) were injected i.v., followed by injection of CAR T cells ($10\times10^6$ per mouse) i.v. on day 3 and 6 post-implantation. Tumor burden was assessed by IVIS imaging at indicated time points. (FIG. 6F) Relative frequency CCRF-GFP in peripheral blood of mice on day 18 post-engraftment is shown on representative dot plots. (FIG. 6G) Kaplan-Meier survival curve for the CCRF model.

(FIG. 9A) Surface expression of CD5 in T-ALL (MOLT4, CCRF-CEM, Jurkat) and T-lymphoma (Sup-T1, Hut-78) cell lines. CD5-negative Burkitt lymphoma cell lines Raji and Daudi are shown as negative control. (FIG. 9B) CD5 expression in CD5 CAR T cells, autologous activated T cells (ATC) and Jurkat cells. CD5-negative Raji cells serve as a negative control. (FIG. 9C) Surface expression of CD5 antigen on the cell surface of activated autologous T cells (left) and Jurkat (right) upon co-culture with CD5 CAR T cells at a 1:1 E:T ratio. At indicated time points (0, 5 and 10 minutes) cells were chilled on ice to prevent further downregulation of CD5 and stained with anti-CD5 antibodies (clone UCHT-2) on ice. (FIG. 9D) Surface staining of CD5 on target cells upon longer co-culture (up to 6 h). Data from one representative donor are shown (n=3).

(FIG. 12A) Peripheral blood from mice previously engrafted with GFP+Jurkat (top panel) and CCRF (bottom panel) cells was collected 3 days after CAR T injection by tail vein bleeding and the frequency of hCD45+ GFP− (CAR T cells) was analyzed by flow cytometry. Five individual mice in each group are depicted. Bar graphs show the summary of the data. (FIG. 12B) Average proportion of CD4 and CD8 cells within each group is shown in the pie charts. (FIG. 12C) Frequency of CAR T cells was analyzed in peripheral blood of mice engrafted with Jurkat cells and collected 12 days after CAR T injection. (FIG. 12D) Average proportion of CD4 and CD8 CAR T cells in both groups 12 days after CAR T injection is shown in pie charts.

FIGS. 14—4-1BB signaling enhances fratricide of CD5 CAR T cells.

DETAILED DESCRIPTION OF THE INVENTION

Figure 1A:
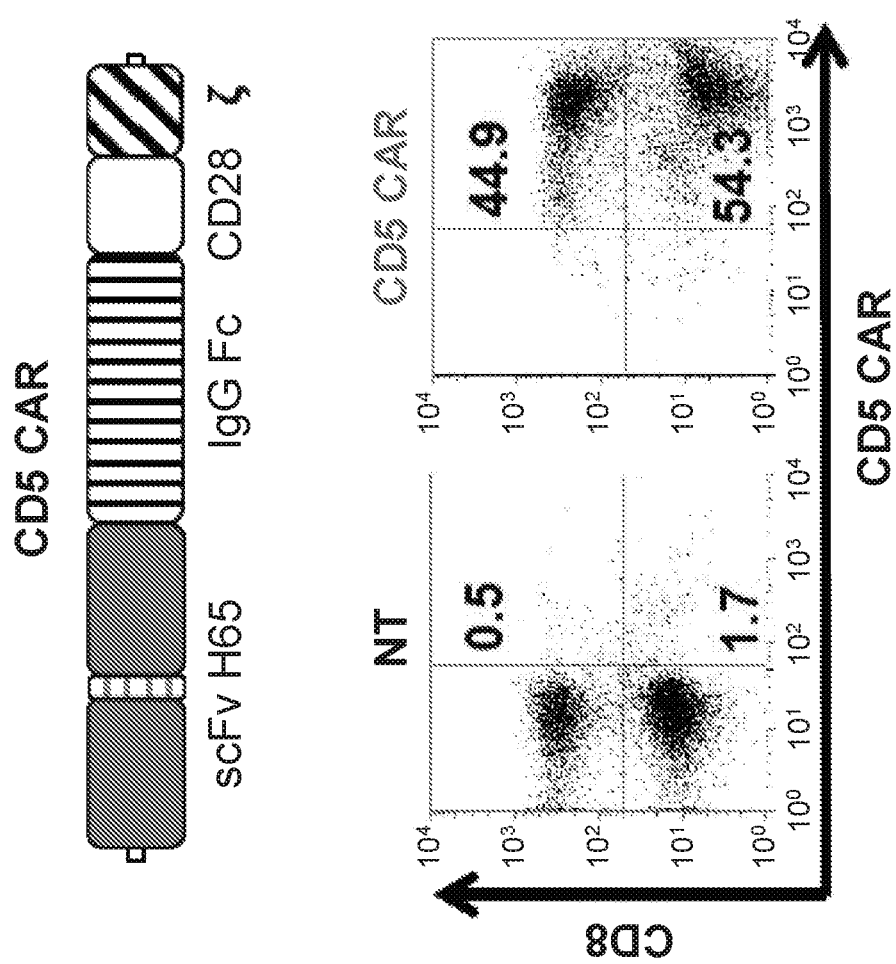
FIG. 1A-1D—CD5 CAR T cells expand and downregulate CD5.

As used herein the specification, "a" or "an" may mean one or more. As used herein in the claim(s), when used in conjunction with the word "comprising", the words "a" or "an" may mean one or more than one. As used herein "another" may mean at least a second or more. In specific embodiments, aspects of the subject matter may "consist essentially of" or "consist of" one or more elements or steps of the subject matter, for example. Some embodiments of the subject matter may consist of or consist essentially of one or more elements, method steps, and/or methods of the subject matter. It is contemplated that any method or composition described herein can be implemented with respect to any other method or composition described herein.

In the present disclosure, adoptive transfer of chimeric antigen receptor (CAR)-redirected T lymphocytes is extended to certain CD5-expressing cancers by targeting the CD5 antigen with a CD5 CAR. Particular aspects of the disclosure include methods of treating CD5-expressing cancers. The cancers may be of any kind, including leukemia, lymphoma, breast cancer, and thymus cancer, for example. In particular embodiments, the cancers are T-cell or B-cell malignancies. In other aspects of the disclosure, immune cells expressing the CD5 CAR are utilized for medical conditions other than cancer. As an example, the cells may be used to target unwanted/self-reactive T cells, such as in graft-versus-host disease or autoimmunity disorders, given that the immune cells of the disclosure can kill autologous T cells.

Described herein is a novel CAR targeting CD5, a common marker expressed in most T-cell leukemia/lymphoma blasts and normal T cells. Upon transduction with CD5 CAR, T cells produced limited and transient fratricide and eventually acquired resistance to self-killing. Expansion of CD5 CAR T cells coincided with downregulation of CD5 from the cell surface. At the same time, CD5 CAR T cells efficiently recognized and completely eliminated CD5-positive T-ALL and T cell lymphoma cell lines in vitro. Moreover, CD5 CAR T cells dramatically suppressed systemic in vivo disease progression in xenograft mouse models. Importantly, CD5 CAR T cells demonstrated significant cytotoxicity against primary T-ALL cells, highlighting the therapeutic potential of CD5 CAR for patients with T-cell malignancies. Overall, CD5 CAR can redirect normal T cells to eliminate CD5-positive malignant T-cells while producing only limited fratricide.

I. CD5

CD5 (for cluster of differentiation 5) is a transmembrane receptor that is expressed only in certain cells, including at least T- and some B-lymphocytes. CD5 is upregulated upon T cell activation and inhibits TCR signaling. CD5 is highly expressed in most T-cell leukemias/lymphomas as well as in B-cell chronic lymphocytic leukemia, mantle cell lymphoma, and hairy cell leukemia. CD5 also known to increase resistance to apoptosis.

An example of a human CD5 nucleic acid is at National Center for Biotechnology Information's GenBank® database at Accession No. NM_014207. An example of a human CD5 polypeptide is at GenBank®'s Accession No. NP_055022. One of skill in the art is able to generate antibodies, including scFv's against CD5 based on knowledge at least of the polypeptide and routine practices, although numerous anti-CD5 scFvs and monoclonal antibodies are already present in the art.

II. Chimeric Antigen Receptors

Genetic engineering of human immune cells to express tumor-directed chimeric antigen receptors (CAR) can produce antitumor effector cells that bypass tumor immune escape mechanisms that are due to abnormalities in protein-antigen processing and presentation. In certain embodiments of the invention there are CTLs that are modified to comprise a CAR that targets CD5. As used herein, "chimeric antigen receptor" or "CAR" indicates an artificial, recombinant polypeptide comprising at least an extracellular domain that binds to a particular antigen, e.g., a tumor-specific antigen or a tumor-associated antigen; a transmembrane domain, and a primary signaling domain, such as the endodomain from CD3. CARs preferably also comprise one or more co-stimulatory domains, as described elsewhere herein. The CAR, when expressed by an immune cell, e.g., a T lymphocyte, and when the antigen-binding domain binds to the targeted antigen, causes the CAR-expressing cell to kill a cell expressing the targeted antigen.

In particular cases, immune cells include a chimeric antigen receptor that is non-natural and engineered at least in part by the hand of man. In particular cases, the engineered CAR has one, two, three, four, or more components, and in some embodiments the one or more components facilitate targeting or binding of the T lymphocyte to the CD5-comprising cancer cell. In specific embodiments, the CAR comprises an antibody for CD5, part or all of a cytoplasmic signaling domain, and/or part or all of one or more co-stimulatory molecules, for example endodomains of co-stimulatory molecules. In specific embodiments, the antibody is a single-chain variable fragment (scFv).

In particular embodiments, the CD5-specific CAR comprises an extracellular domain that targets the CAR to CD5. In certain embodiments, the extracellular domain is, or comprises, an antibody that binds to CD5. In specific embodiments, the antibody is an scFv. The antibody, e.g., scFv, may be derived from any monoclonal antibody that binds to CD5, such as from one of the following: H65 (Santa Cruz Biotechnology; Santa Cruz, Calif.); clone CRIS1 or clone 4C7 (Abnova Corporation; Walnut, Calif.); OX-19 (Santa Cruz Biotechnology; Santa Cruz, Calif.); Leu-1 (Becton-Dickinson; Mountain View, Calif.) and UCHT2 (Accurate Scientific; Westbury, N.Y.); 53-7.3 (Affymetrix; Santa Clara, Calif.); 4H8E6 (Life Technologies; Grand Island, N.Y.); T101; EP2952 (Abcam, Cambridge Mass.); or L17F12. In other embodiments, the antibody, e.g., scFv, is or is derived from anti-CD5 antibodies D-9, H-3, HK231, N-20, Y2/178, H-300, L17F12, CD5/54/F6, Q-20, or CC17 (all available from Santa Cruz Biotechnology, Dallas Tex.). The antibody may also be one that is generated de novo against CD5, and the scFv sequence may be obtained, or derived, from such de novo antibodies.

Examples of specific anti-CD5 scFv include at least MOM-18539-S(P) and MOM-18885-S(P) (Creative Diagnostics; Suffolk County, N.Y.).

In certain embodiments, the anti-CD5 CAR comprises an extracellular domain that is or comprises a ligand for CD5. In specific embodiments, the anti-CD5 CAR comprises an extracellular domain that comprises CD72 (Lyb-2) and fragments and mimetics thereof. An example of a human CD72 nucleic acid is at GenBank® Accession No. NM_001782 and an example of a human CD72 protein is at NP 001773.

In certain embodiments, the CD5-specific CAR comprises a cytoplasmic signaling domain, such as one derived from the T cell receptor zeta-chain (CD3), e.g., to produce a primary T cell activation signal. Preferably the CD5-specific CAR additionally comprises one or more stimulatory domains that, e.g., produce stimulatory signals for T lymphocyte proliferation and effector function following engagement of the chimeric receptor with the target antigen. Examples of such costimulatory domains include, but are not limited to, costimulatory endodomains from co-stimulatory molecules such as CD2, CD28, CD27, CD137 (4-1BB), Inducible T-cell Costimulator (ICOS), OX40, CD30, HVEM, CD40, LFA-1 (CD11a/CD18), ICAM-1, and a combination of two or more thereof, and/or the signaling components of cytokine receptors such as IL7, IL15, or IL21. However, in specific embodiments, 4-1BB is not employed in the CAR, because 4-1BB signaling can enhance fratricide of CD5 CAR T cells (see, e.g., FIG. 14). In particular embodiments, co-stimulatory molecules are employed to enhance the activation, proliferation, and cytotoxicity of T cells produced by the CD5-comprising CAR after antigen engagement. In specific embodiments, the co-stimulatory molecules are CD28, OX40, and/or 4-1BB, for example.

The CAR may be first generation (e.g., comprising a CD5-targeting extracellular domain, transmembrane domain, and CD3ζ only), second generation (e.g., comprising a CD5-targeting extracellular domain, transmembrane domain, CD3ζ and CD28 costimulatory endodomain), or third generation (CAR in which signaling is provided by CD3ζ together with co-stimulation provided by CD28 and, for example, a tumor necrosis factor receptor (TNFR), such as 4-1BB or OX40).

In particular cases the CAR is specific for CD5, and in certain embodiments, the present invention provides chimeric T cells specific for CD5 by joining an extracellular antigen-binding domain derived from a CD5-specific antibody to cytoplasmic signaling domains derived from the T-cell receptor ζ-chain, optionally with the endodomains of the exemplary costimulatory molecules CD28 and OX40, for examples. In embodiments, the CAR is expressed in human cells, including human T cells, and the targeting of CD5-positive cancers is encompassed herein.

The CD5 CARs of the present disclosure may have a linker (which may also be referred to as a spacer) and/or a hinge. The hinge region is the connecting sequence between the ectodomain and the transmembrane domain, and in some embodiments the CD5 CAR utilizes a hinge, whereas in other embodiments the CD5 CAR does not utilize a hinge. In specific embodiments, the hinge is of a particular length, such as 10-20, 10-15, 11-20, 11-15, 12-20, 12-15, or 15-20 amino acids in length, for example. In specific embodiments, the hinge is a small flexible polypeptide that connects CH2-CH3 and CH1 domains of IgG Fc.

A spacer of any suitable length is utilized for the CD5 scFv to properly bind its ligand. In specific embodiments, the spacer facilitates CAR detection with spacer-specific antibodies, although in some cases of the present disclosure a linker is not used.

Any combination of linkers and hinges may be employed in the CD5 CAR. For example, one may utilize CH2-CH3 hinge (part or all) from various IgG subclasses (IgG1-4, either modified or not). However, in some cases the entire CH2-CH3 hinge is not utilized but instead a portion of the hinge is used (such as CH3 by itself or part of CH3 by itself). In particular embodiments, the CH2-CH3 hinge derived from IgG1 is utilized, and in some cases the entire CH2-CH3 hinge is used (all 229 amino acids), only the CH3 hinge (119 amino acids) is used, or a short hinge (12 amino acids) is used.

In specific cases, one can modify the identity or length of the spacer and/or hinge to optimize efficiency of the CAR. See, for example, Hudecek et al. (2014) and Jonnalagadda et al. (2015) In specific embodiments, the CD5 CAR utilizes IgG4 hinge+CH3 or utilizes CD8a stalk, for example.

Thus, in specific embodiments a spacer domain that is commonly used in CAR design comprises an IgG hinge region, typically IgG1 or IgG4, and the CH2-CH3 domain of IgG Fc. The use of the IgG Fc domain can provide flexibility to the CAR, has low immunogenicity, facilitates detection of CAR expression using anti-Fc reagents, and allows removal of one or more CH2 or CH3 modules to accommodate different spacer lengths. However, in one embodiment mutations in certain spacers to avoid FcγR binding may improve CAR+ T cell engraftment and antitumor efficacy to avoid binding of soluble and cell surface Fc gamma receptors, for example, yet maintain the activity to mediate antigen-specific lysis. For example, one can employ IgG4-Fc spacers that have either been modified in the CH2 region. For example, the CH2 region may be mutated, including point mutations and/or deletions. Specific modifications have been demonstrated at two sites (L235E; N297Q) within the CH2 region and/or incorporate a CH2 deletion (Jonnalagadda et al, 2015). In specific embodiments, one may employ the IgG4 hinge-CH2-CH3 domain (229 aa in length) or only the hinge domain (12 aa in length) (Hudecek et al., 2015). In particular embodiments, the spacer region is 10-250 amino acids in length, although it may be 10-225, 10-200, 10-175, 10-150, 10-100, 10-50, 10-25, 12-250, 12-225, 12-200, 12-175, 12-150, 12-100, 12-50, 12-25, 25-250, 25-225, 25-200, 25-175, 25-150, 25-100, 25-50, 50-250, 50-225, 50-200, 50-175, 50-150, 50-100, 100-250, 100-225, 100-200, 100-175, 100-150, 100-125, 150-250, 150-225, 150-200, 150-175, 175-250, 175-225, 175-200, 200-250, or 225-250 amino acids in length, for example, any range therein between, and so forth.

Preferably the CD5-specific chimeric antigen receptors provided herein comprise a transmembrane (TM) domain. In certain embodiments, the transmembrane domain is, or is derived from, the TM domain of CD3 epsilon, CD4, CD5, CD8, CD9, CD16, CD22, CD28, CD33, CD37, CD45, CD64, CD80, CD86, CD134, CD137, or CD154.

In certain embodiments of a CD5 CAR expression construct, the expression construct comprises at least 1) the CD5 CAR; 2) full CH2-CH3 from IgG1, IgG2, IgG3, or IgG4 (or CH3 or stalk from CD8a); 3) transmembrane domain; and 4) CD28 (or one or more other costimulatory domains; and 5) CD3ζ. SEQ ID NO:13 (which consists of the amino acid sequences shown in SEQ ID NOS:14-17 below, in order) provides an example of a CD5 CAR, including CD5scFv plus leader; IgG1 spacer (CH2+CH3)+hinge; CD28 TM+cyto; and zeta as follows:

```
                                          (SEQ ID NO: 14)
MEFGLSWLFLVAILKGVQCIDAMGNIQLVQSGPELKKPGETVKISCKASG

YTFTNYGMNWVKQAPGKGLRWMGWINTHTGEPTYADDFKGRFAFSLETSA

STAYLQINNLKNEDTATYFCTRRGYDWYFDVWGAGTTVTVSSGGGGSGGG

GSGGGGSDIKMTQSPSSMYASLGERVTITCKASQDINSYLSWFHHKPGKS

PKTLIYRANRLVDGVPSRFSGSGSGQDYSLTISSLDYEDMGIYYCQQYDE

SPWTFGGGTKLEMKGSGDPA (CD5 scFv + leader)

(SEQ ID NO: 15)
EPKSPDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSRDELTKNQVSL

TCLVKGFYPSDIAVEWESNGQPENNYKTTPPVLDSDGSFFLYSKLTVDKS

RWQQGNVFSCSVMHEALHNHYTQKSLSLSPGKKDPK (IgG1 spacer (CH2 + CH3) + hinge)

(SEQ ID NO: 16)
FWVLVVVGGVLACYSLLVTVAFIIFWVRSKRSRLLHSDYMNMTPRRPGPT

RKHYQPYAPPRDFAAYRS (CD28 TM + cyto)

(SEQ ID NO: 17)
RVKFSRSADAPAYQQGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR (zeta)
```

The immune cell comprising the CD5 CAR in the cell may additionally comprise one or more other CARs, such as those specific for B Cell Maturation Antigen (BCMA), CD19, CD20, CD22, Kappa or light chain, Glypican-3, CD30, CD33, CD123, CD38, ROR1, ErbB2, ErbB3/4, EGFR vIII, carcinoembryonic antigen, EGP2, EGP40, mesothelin, TAG72, PSMA, NKG2D ligands, B7-H6, IL-13 receptor α2, IL-11 receptor R α, MUC1, MUC16, CA9, GD2, GD3, HMW-MAA, CD171, Lewis Y, G250/CAIX, HLA-AI MAGE A1, HLA-A2 NY-ESO-1, PSC1, folate receptor-α. CD44v7/8, 8H9, NCAM, VEGF receptors, 5T4, Fetal AchR, NKG2D ligands, CD44v6, CD7, and other tumor-associated antigens or actionable mutations that are identified through genomic analysis and or differential expression studies of tumors, for example. In specific embodiments, the CAR utilizes two or more antigen recognizing domains, such as two or more scFvs. That is, in particular embodiments, the CAR of the present disclosure utilizes a CD5 scFv in tandem with another scFv (which may be referred to as a tandem CAR or TanCAR). In certain embodiments, in a configuration of a single CAR the CD5 scFv is utilized with another scFv (or embedded or fused with another receptor) to provide recognition of both CD5 and another antigen to which the other antibody or receptor binds.

III. Cells

Provided herein are cells e.g., immune cells that express a CD5-targeting chimeric antigen receptor.

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a eukaryotic cell that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny. As used herein, the terms "engineered" and "recombinant" cells or host cells are intended to refer to a cell into which an exogenous nucleic acid sequence, such as, for example, a vector, has been introduced. Therefore, recombinant cells are distinguishable from naturally occurring cells which do not contain a recombinantly introduced nucleic acid. In embodiments of the invention, a host cell is a T cell or T lymphocyte, including a cytotoxic T cell (also known as TC, Cytotoxic T Lymphocyte, CTL, T-Killer cell, cytolytic T cell, CD8+ T-cells, CD4+ T cells, or killer T cell); NK cells and NKT cells are also encompassed in the invention.

In certain embodiments, the cells, e.g., CD5-specific CAR T cells described herein, are provided in a form suitable for administration to a recipient, e.g., a human recipient, e.g., an individual having a CD5-expressing tumor. In a specific embodiment, the form suitable for administration to a recipient is a pharmaceutical composition.

In certain embodiments, the immune cells provided herein are transformed with a vector that expresses a nucleotide sequence encoding the CD5-specific CAR provided herein. The vector may be any vector that can (1) replicate in an immune cell and (2) express a protein within a T cell. in specific embodiments, the vector is a retroviral vector.

In specific embodiments, the vector comprises control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

With respect to a potential recipient of the CD5-specific CAR T cells provided herein, the cells can be autologous, syngeneic, allogenic or xenogeneic cells.

In many situations one may wish to be able to kill the modified CTLs, where one wishes to terminate the treatment, the cells become neoplastic, in research where the absence of the cells after their presence is of interest, and/or another event. For this purpose, one can provide for the expression of certain gene products in which one can kill the modified cells under controlled conditions, such as inducible suicide genes, such as caspase 9.

In particular embodiments, the immune cells of the present disclosure are modified in one or more ways other than expressing a CD5 CAR. For example, the CD5 CAR may have additional modifications to its molecule, or the cells may have a second, third, fourth, or more modification other than the CD5 CAR. Any modification to the immune cells may manifest as one or more additional polynucleotides. For example, the polynucleotide that expresses the CD5 CAR may also express a suicide gene product, a cytokine, an additional CAR, a cytokine receptor, and/or a chimeric cytokine receptor. In specific embodiments, the CD5 CAR is a CAR that recognizes two different antigens by comprising two different scFvs that bind two separate antigens, one of which is CD5 scFv.

Alternative to, or in addition to, the immune cells harboring a polynucleotide that expresses the CD5 CAR and also expresses one or more modifications, the immune cells may harbor one or more separate polynucleotides that encode a suicide gene product, a cytokine, an additional CAR, a cytokine receptor, and/or a chimeric cytokine receptor.

In embodiments wherein a cytokine is expressed in the immune cells from a recombinant polynucleotide, the cytokine may any particular suitable one, but in specific embodiments the cytokine is one or more of IL-2, IL-7, IL-15, IL-21, IL-12, GM-CSF, G-CSFm and others. Cytokine receptors may be included in the cells, including receptors for IL-4, IL-10, TGF beta, and others.

Additional CAR molecules may be expressed on the cells, including, for example, CARs that target CD19, CD20, CD22, Kappa or light chain, Glypican-3, CD30, CD33, CD123, CD38, ROR1, ErbB2, ErbB3/4, EGFR vIII, carcinoembryonic antigen, EGP2, EGP40, mesothelin, TAG72, PSMA, NKG2D ligands, B7-H6, IL-13 receptor α2, IL-11 receptor R α, MUC1, MUC16, CA9, GD2, GD3, HMW-MAA, CD171, Lewis Y, G250/CAIX, HLA-AI MAGE A1, HLA-A2 NY-ESO-1, PSC1, folate receptor-α, CD44v7/8, 8H9, NCAM, VEGF receptors, 5T4, Fetal AchR, NKG2D ligands, CD44v6, CD7, or other tumor-associated antigens or actionable mutations that are identified through genomic analysis and or differential expression studies of tumors.

In some embodiments, the cells comprise one or more chimeric cytokine receptors that may or may not be expressed from the same molecule as the CD5 CAR. A chimeric cytokine receptor comprises an exodomain and an endodomain that are not naturally of the same molecule. In specific embodiments, the exodomain is from the exodomain of a receptor. The exodomain of the chimeric cytokine receptor binds a cytokine, in particular embodiments. The exodomain may be from a receptor or molecule that can bind to TGFβ, IL10, IL4, IL13, IL6, IL8, IL5, VEGF, IL22, IL1, IL1β, IL35, TNF, GM-CSF, M-CSF, G-CSF, LAG3, or TIM3, for example. The exodomain may be from a chemokine receptor. For the endodomain component of the chimeric cytokine receptor, the endodomain may be a signal transducing endodomain. Examples of signal transducing domains include endodomains from TLR1, TLR2, TLR3, TLR4, TLR5, TLR6, TLR7, TLR8, TLR9, CD28, OX-40, 4-1BB, CD80, CD86, ICOS, CD40, CD27, CD30, CD226, IL7, IL2, IL15, IL21, IL12 and IFN-gamma. In some embodiments, the endodomain is an inhibitory endodomain, such as endodomains from PD-1, CTLA4, KIR2/KIR3, LIR, BTLA, or CEACAM, for example. Specific examples of chimeric cytokine receptors include IL4/7 receptor (Leen et al. Mol Ther 2014); TGFbeta/TLR4 receptor, and others.

IV. Illustrative Exemplifications and Therapeutic Uses of the Cells

Embodiments of the disclosure further encompass a process for the production of the CD5-specific immune cells, e.g., CD5-specific CAR T cells, provided herein, a method for the prevention, treatment or amelioration of cancer, and the use of the cells in the prevention, treatment or amelioration of cancer.

In various embodiments the expression constructs, nucleic acid sequences, vectors, host cells and/or pharmaceutical compositions comprising the same are used for the prevention, treatment or amelioration of a cancerous disease, such as a tumorous disease. In particular embodiments, the pharmaceutical composition of the present disclosure may be particularly useful in preventing, ameliorating and/or treating cancer, including cancer having solid tumors, for example.

As such, in one embodiment, provided herein is a method of treating an individual having a cancer, wherein cells of the cancer express CD5, comprising administering to the individual a therapeutically effective amount of immune cells that express a chimeric antigen receptor that targets CD5. In another embodiment, provided herein is the use of a therapeutically effective amount of immune cells that express a chimeric antigen receptor that targets CD5 for the treatment of an individual having a cancer, wherein the cells of the cancer express CD5. In another embodiment, provided herein is use of a therapeutically effective amount of immune cells that express a chimeric antigen receptor that targets CD5 for the manufacture of a medicament for treatment of an individual having a cancer, wherein the cells of the cancer express CD5. In specific embodiments, the immune cells are T-cells, CTLs, NK cells, or NKT cells. In certain specific embodiments, the immune cells are not T-cells, or are not NK cells.

In specific embodiments, the chimeric antigen receptor that targets CD5 is any of the chimeric antigen receptors described herein. In a more specific embodiment, the chimeric antigen receptor comprises a CD5 targeting moiety, a CD3ζ signaling domain, and a CD28 costimulatory domain. In another more specific embodiment, the chimeric antigen receptor comprises a CD5 targeting moiety, a CD3ζ signaling domain, and a CD137 (4-1BB) costimulatory domain. In another more specific embodiment, the chimeric antigen receptor comprises a CD5 targeting moiety, a CD3ζ signaling domain, a CD28 costimulatory domain and a CD137 (4-1BB) costimulatory domain. In another more specific embodiment, the chimeric antigen receptor comprises amino acid sequence of one or more of SEQ ID NO:14, SEQ ID NO:15, SEQ ID NO:16, and/or SEQ ID NO:17. In a more specific embodiment, the chimeric antigen receptor comprises the amino acid sequence of SEQ ID NO:13.

In certain embodiments, of the methods or uses herein, the cancer expresses CD5, e.g., an amount of CD5 detectable by, e.g., an ELISA assay or flow cytometry. In certain embodiments of the methods or uses herein, the cancer is a blood cancer. In a more specific embodiment, the blood cancer is a cancer of aberrant T cells, e.g., a T-cell leukemia or a T-cell lymphoma. In another more specific embodiment, the blood cancer is a cancer of aberrant B cells, e.g., a B-cell leukemia or a B-cell lymphoma. In more specific embodiments, the T-cell leukemia or T-cell lymphoma is T-lineage Acute Lymphoblastic Leukemia (T-ALL), Hodgkin's lymphoma, or a non-Hodgkin's lymphoma, acute lymphoblastic leukemia (ALL), chronic lymphocytic leukemia (CLL), large granular lymphocytic leukemia, adult T-cell leukemia/lymphoma (ATLL), T-cell prolymphocytic leukemia (T-PLL), T-cell chronic lymphocytic leukemia, "knobby" T-cell leukemia, T-prolymphocytic leukemia, T-cell lymphocytic leukemia, B-cell chronic lymphocytic leukemia, mantle cell lymphoma, peripheral T-cell lymphoma not otherwise specified (PTCL-NOS), anaplastic large-cell lymphoma (e.g., anaplastic lymphoma kinase (+) or anaplastic lymphoma kinase (−)), cutaneous T-cell lymphoma (e.g., mycosis fungoides), angioimmunoblastic lymphoma, cutaneous anaplastic large cell lymphoma, enteropathy-type T-cell lymphoma, hematosplenic gamma-delta T-cell lymphoma, lymphoblastic lymphoma, or hairy cell leukemia. In another more specific embodiment, the cancer is a treatment-related T-cell lymphoma, e.g., a T-cell lymphoma that arises after drug therapy, chemotherapy, or after bone marrow transplantation. In other specific embodiments, the blood cancer is acute lymphoblastic leukemia (B-ALL) or chronic lymphocytic leukemia (B-CLL). In other embodiments, the cancer is a solid tumor, wherein the cells of the solid tumor express CD5.

In various embodiments, the administration of the composition(s) of the disclosure is useful for the treatment of specific stages of cancer, including for indolent forms, acute forms, minimal residual disease, early solid tumor, advanced solid tumor and/or metastatic solid tumor.

As used herein "treatment" or "treating," includes any beneficial or desirable effect on the symptoms or pathology of a disease or pathological condition, and may include even minimal reductions in one or more measurable markers of the disease or condition being treated, e.g., cancer. Treatment can involve optionally either the reduction or amelioration of symptoms of the disease or condition, or the delaying of the progression of the disease or condition. "Treatment" does not necessarily indicate complete eradication or cure of the disease or condition, or associated symptoms thereof.

As used herein, "prevent," and similar words such as "prevented," "preventing" etc., indicate an approach for preventing, inhibiting, or reducing the likelihood of the occurrence or recurrence of, a disease or condition, e.g., cancer. It also refers to delaying the onset or recurrence of a disease or condition or delaying the occurrence or recurrence of the symptoms of a disease or condition. As used herein, "prevention" and similar words also includes reducing the intensity, effect, symptoms and/or burden of a disease or condition prior to onset or recurrence of the disease or condition.

In particular embodiments, the present invention contemplates, in part, viruses, expression constructs, nucleic acid molecules and/or vectors that can administered either alone or in any combination with another therapy, and in at least some aspects, together with a pharmaceutically acceptable carrier or excipient. In certain embodiments, prior to administration of the viruses, they may be combined with suitable pharmaceutical carriers and excipients that are well known in the art. The compositions prepared according to the disclosure can be used for the prevention or treatment or delaying of onset or worsening of cancer.

Furthermore, the disclosure relates to a method for the prevention, treatment or amelioration of a cancerous (including tumorous) disease comprising the step of administering to a subject in need thereof an effective amount of immune cells of the disclosure, wherein the virus expresses a molecule comprising an activation domain that binds to a target on an immune cell and an antigen recognition domain that binds one or more molecules produced by or present on a target cell. The disclosure includes nucleic acid sequence that encodes a CD5-expressing CAR, vector(s) that encodes the CD5-expressing CAR, as contemplated herein and/or produced by a process as contemplated herein.

The disclosure further encompasses co-administration protocols with other cancer therapies, e.g. bispecific antibody constructs, targeted toxins or other compounds, including those which act via immune cells, including T-cell therapy. The clinical regimen for co-administration of the inventive composition(s) may encompass co-administration at the same time, before and/or after the administration of the other component. Particular combination therapies include chemotherapy, radiation, surgery, hormone therapy, and/or other types of immunotherapy.

In certain embodiments, provided herein is a kit comprising one or more oncolytic viruses as described herein, a nucleic acid sequence as described herein, a vector as described herein and/or a host as described herein. It is also contemplated that the kit of this disclosure comprises a pharmaceutical composition as described herein above, either alone or in combination with further medicaments to be administered to an individual in need of medical treatment or intervention. In particular embodiments, the kit comprises a set of instructions for use of the cells, viruses, vectors, nucleic acid sequences, and/or pharmaceutical compositions described herein.

In particular embodiments, nucleic acid introduction into the immune cells need not result in integration in every case. In some situations, transient maintenance of the nucleic acid introduced may be sufficient. In this way, one could have a short term effect, where cells could be introduced into the host and then turned on after a predetermined time, for example, after the cells have been able to home to a particular site.

The viruses may be introduced into a host organism, e.g., a mammal, in a wide variety of ways. The viruses may be introduced at the site of the tumor, in specific embodiments, although in alternative embodiments viruses hone to the cancer or are modified to hone to the cancer. The number of viruses that are employed will depend upon a number of circumstances, the purpose for the introduction, the lifetime of the cells, the protocol to be used, for example, the number of administrations, the stability of the viruses, and the like. The viruses may be applied in a dispersion, and may be injected at or near the site of interest. The viruses may be in a physiologically-acceptable medium.

By way of illustration, individuals with cancer or at risk for cancer (such as having one or more risk factors) or suspected of having cancer may be treated as follows. The immune cells modified as described herein may be administered to the individual and retained for extended periods of time. The individual may receive one or more administrations of the cells. In some embodiments, the genetically modified cells are encapsulated to inhibit immune recognition and placed at the site of the tumor.

Embodiments of the disclosure also include methods of suppressing the autoimmune system in an individual using cells bearing CD5 CARs, such as methods of treating autoimmune disease and methods of suppressing rejection of organs, cells, and/or tissue, including in graft-versus-host disease. The disclosure includes methods of preventing rejection of organs, cells, and/or tissue following their transplant or treating rejection upon its occurrence following their transplant.

Embodiments of the disclosure also include methods of suppressing the autoimmune system in an individual using cells bearing CD5 CARs, such as methods of treating autoimmune disease and methods of suppressing rejection of organs, cells, and/or tissue, including in graft-versus-host disease. The disclosure includes methods of preventing rejection of organs, cells, and/or tissue following their transplant or treating rejection upon its occurrence following their transplant.

V. Introduction of Constructs into CTLs

Expression vectors that encode the CD5 CARs can be introduced as a DNA molecule or construct. In certain embodiments, the DNA molecule or construct is, or is comprised within, a vector. In specific embodiments, the vector comprises at least one marker that allows for selection of host cells that contain the construct(s). The constructs can be prepared in conventional ways, where the genes and regulatory regions may be isolated, as appropriate, ligated, cloned in an appropriate cloning host, analyzed by restriction or sequencing, or other convenient means. Particularly, using PCR, individual fragments including all or portions of a functional unit may be isolated, where one or more mutations may be introduced using "primer repair", ligation, in vitro mutagenesis, etc., as appropriate. The construct(s) once completed and demonstrated to have the appropriate sequences may then be introduced into the CTL by any convenient means. The constructs may be integrated and packaged into non-replicating, defective viral genomes like Adenovirus, Adeno-associated virus (AAV), or Herpes simplex virus (HSV) or others, including retroviral vectors or lentiviral vectors, for infection or transduction into cells, e.g., T cells. The constructs may include viral sequences for transfection, if desired. Alternatively, the construct may be introduced by fusion, electroporation, transfection, lipofection, or the like. The host cells may be grown and expanded in culture before introduction of the construct(s), followed by the appropriate treatment for introduction of the construct (s) and integration of the construct(s). The cells are then expanded and screened by virtue of a marker present in the construct. Various markers that may be used successfully include hprt, neomycin resistance, thymidine kinase, hygromycin resistance, etc. A detailed discussion of vectors suitable for use in the methods provided herein is presented in Section VII, below.

In some instances, one may have a target site for homologous recombination, where it is desired that a construct be integrated at a particular locus. For example,) can knock-out an endogenous gene and replace it (at the same locus or elsewhere) with the gene encoded for by the construct using materials and methods as are known in the art for homologous recombination. For homologous recombination, one may use either OMEGA or O-vectors. See, for example, Thomas and Capecchi, Cell (1987) 51, 503-512; Mansour, et al., Nature (1988) 336, 348-352; and Joyner, et al., Nature (1989) 338, 153-156.

Vectors containing useful elements such as bacterial or yeast origins of replication, selectable and/or amplifiable markers, promoter/enhancer elements for expression in prokaryotes or eukaryotes, etc. that may be used to prepare stocks of construct DNAs and for carrying out transfections are well known in the art, and many are commercially available.

VI. Administration of Cells

In certain embodiments, the immune cells that have been modified with the CD5 CAR and optionally other construct (s) are then grown in culture under selective conditions and cells that are selected as having the construct may then be expanded and further analyzed, using, for example, the polymerase chain reaction for determining the presence of the construct in the host cells. Once the modified host cells have been identified, they may then be used as planned, e.g. expanded in culture or introduced into a host organism.

Depending upon the nature of the cells, the cells may be introduced into a host organism, e.g. a mammal, e.g., human, e.g., human individual having a CD5-expressing cancer, in a wide variety of ways. The cells may be introduced at the site of the tumor, in specific embodiments, although in alternative embodiments the cells home to the cancer or are modified to home to the cancer. The number of cells that are employed will depend upon a number of circumstances, the purpose for the introduction, the lifetime of the cells, the protocol to be used, for example, the number of administrations, the ability of the cells to multiply, the stability of the recombinant construct, and the like. The cells may be applied as a dispersion, generally being injected at or near the site of interest. The cells may be in a physiologically-acceptable medium.

In specific embodiments of the methods of treatment or uses disclosed herein, the therapeutically effective dose or dosage of the immune cells provided herein, which express a CD5-specific chimeric antigen receptor, can comprise about $10^5/m^2$, $10^6/m^2$, $10^7/m^2$, $10^8/m^2$, $10^9/m^2$, or $10^{10}/m^2$ are employed in methods of the disclosure. In certain embodiments, the number of cells provided to an individual in need thereof is from $10^6/m^2$ to $10^{10}/m^2$; $10^7/m^2$ to $10^{10}/m^2$; $10^8/m^2$ to $10^{10}/m^2$; $10^9/m^2$ to $10^{10}/m^2$; $10^6/m^2$ to $10^9/m^2$; $10^7/m^2$ to $10^9/m^2$; $10^8/m^2$ to $10^9/m^2$; $10^7/m^2$ to $10^{10}/m^2$; $10^7/m^2$ to $10^9/m^2$; $10^7/m^2$ to $10^8/m^2$; $10^8/m^2$ to $10^9/m^2$; or $10^9/m^2$ to $10^{10}/m^2$.

In other specific embodiments, the therapeutically effective dose or dosage of the immune cells provided herein, which express a CD5-specific chimeric antigen receptor, can comprise about $1\times10^5$/kg, $5\times10^5$/kg, $1\times10^6$/kg, $5\times10^6$/kg, $1\times10^7$/kg, $5\times10^7$/kg, $1\times10^8$/kg, $5\times10^8$/kg, $1\times10^9$/kg, $5\times10^9$/kg, $1\times10^{10}$/kg, or $5\times10^{10}$/kg. In certain embodiments, the number of cells provided to an individual in need thereof is from $10^5$/kg to $106$/kg; $10^6$/kg to $10^7$/kg, $10^7$/kg to $10^8$/kg, $10^6$/kg to $10^{10}$/kg; $10^7$/kg to $10^{10}$/kg; $10^8$/kg to $10^{10}$/kg; $10^9$/kg to $10^{10}$/kg; $10^6$/kg to $10^9$/kg; $10^7$/kg to $10^9$/kg; $10^8$/kg to $10^9$/kg; $10^7$/kg to $10^{10}$/kg; $10^7$/kg to $10^9$/kg; $10^7$/kg to $10^8$/kg; $10^8$/kg to $10^9$/kg; or $10^9$/kg to $10^{10}$/kg.

An effective dose of the immune cells provided herein can vary according to the needs of a particular individual and of the cancer that that individual has. Therefore, it is expected that for each individual patient, even if there were cells that could be administered to the population at large, each patient would be monitored for the proper dosage for the individual, and such practices of monitoring a patient are routine in the art. Indicia of successful treatment could be, e.g., detectable reduction in the growth of a tumor (e.g., as seen by MRI or the like), or reduction in one or more symptoms of a cancer or other medical condition that expresses CD5.

In specific embodiments, the tumor load of an individual receiving therapy of the disclosure is monitored. In particular cases, tumor load is monitored in peripheral blood by flow cytometric analysis of T cell blasts (CD5 and other markers, depending on their phenotype) and in the bone marrow aspirates (percent blasts). In specific embodiments, CT/MRI scans are utilized. In particular embodiments, CD5-specific CAR T cells are provided to the individual more than once and, in some embodiments, the cells are re-administered upon ascertaining a tumor load of the individual.

In particular cases, an individual is provided with therapeutic immune cells modified to comprise a CAR specific for CD5 in addition to other types of therapeutic cells, such as other immune cells. The cells may be delivered at the same time or at different times. The cells may be delivered in the same or separate formulations. The cells may be provided to the individual in separate delivery routes. The cells (either the CD5-specific CAR T cells or the other type of therapeutic cells, or both) may be delivered by injection at a tumor site or intravenously or intraarterially, subcutaneously, intraperitoneally, intrathecally, intramuscularly, intracranially, or directly into an affected organ, or orally, for example. Routine delivery routes for such compositions are known in the art.

VII. Nucleic Acid-Based Expression Systems

A polynucleotide encoding the CD5 CAR and, optionally, another gene, such as a cytokine and/or suicide gene, may comprise an expression vector.

A. Vectors

The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., yeast artificial chromosomes, or YACs). One of skill in the art would be well equipped to construct a vector through standard recombinant techniques (see, for example, Maniatis et al., 1988 and Ausubel et al., 1994, both incorporated herein by reference).

The term "expression vector" refers to any type of genetic construct comprising a nucleic acid coding for a RNA capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host cell. In addition to control sequences that govern transcription and translation, vectors and expression vectors may contain nucleic acid sequences that serve other functions as well and are described infra.

B. Promoters and Enhancers

A "promoter" is a control sequence that is a region of a nucleic acid sequence at which initiation and rate of transcription are controlled. It may contain genetic elements at which regulatory proteins and molecules may bind, such as RNA polymerase and other transcription factors, to initiate the specific transcription a nucleic acid sequence. The phrases "operatively positioned," "operatively linked," "under control," and "under transcriptional control" mean that a promoter is in a correct functional location and/or orientation in relation to a nucleic acid sequence to control transcriptional initiation and/or expression of that sequence.

A promoter generally comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30 110 bp upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription. A promoter may or may not be used in conjunction with an "enhancer," which refers to a cisacting regulatory sequence involved in the transcriptional activation of a nucleic acid sequence.

A promoter may be one naturally associated with a nucleic acid sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other virus, or prokaryotic or eukaryotic cell, and promoters or enhancers not "naturally occurring," i.e., containing different elements of different transcriptional regulatory regions, and/or mutations that alter expression. For example, promoters that are most commonly used in recombinant DNA construction include the beta-lactamase (penicillinase), lactose and tryptophan (trp) promoter systems. In addition to producing nucleic acid sequences of promoters and enhancers synthetically, sequences may be produced using recombinant cloning and/or nucleic acid amplification technology, including PCR, in connection with the compositions disclosed herein (see U.S. Pat. Nos. 4,683,202 and 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the organelle, cell type, tissue, organ, or organism chosen for expression. Those of skill in the art of molecular biology generally know the use of promoters, enhancers, and cell type combinations for protein expression, (see, for example Sambrook et al. 1989, incorporated herein by reference). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Additionally any promoter/enhancer combination could also be used to drive expression. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

The identity of tissue-specific promoters or elements, as well as assays to characterize their activity, is well known to those of skill in the art.

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals.

In certain embodiments of the invention, the use of internal ribosome entry sites (IRES) elements are used to create multigene, or polycistronic, messages, and these may be used in the invention.

Vectors can include a multiple cloning site (MCS), which is a nucleic acid region that contains multiple restriction enzyme sites, any of which can be used in conjunction with standard recombinant technology to digest the vector. "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

Splicing sites, termination signals, origins of replication, and selectable markers may also be employed.

C. Plasmid Vectors

In certain embodiments, a plasmid vector is contemplated for use to transform a host cell. In general, plasmid vectors containing replicon and control sequences which are derived from species compatible with the host cell are used in connection with these hosts. The vector ordinarily carries a replication site, as well as marking sequences which are capable of providing phenotypic selection in transformed cells. In a non-limiting example, E. coli is often transformed using derivatives of pBR322, a plasmid derived from an E. coli species. pBR322 contains genes for ampicillin and tetracycline resistance and thus provides easy means for identifying transformed cells. The pBR plasmid, or other microbial plasmid or phage must also contain, or be modified to contain, for example, promoters which can be used by the microbial organism for expression of its own proteins.

In addition, phage vectors containing replicon and control sequences that are compatible with the host microorganism can be used as transforming vectors in connection with these hosts. For example, the phage lambda GEM™ 11 may be utilized in making a recombinant phage vector which can be used to transform host cells, such as, for example, E. coli LE392.

Further useful plasmid vectors include pIN vectors (Inouye et al., 1985); and pGEX vectors, for use in generating glutathione S transferase (GST) soluble fusion proteins for later purification and separation or cleavage. Other suitable fusion proteins are those with ☐ galactosidase, ubiquitin, and the like.

Bacterial host cells, for example, E. coli, comprising the expression vector, are grown in any of a number of suitable media, for example, LB. The expression of the recombinant protein in certain vectors may be induced, as would be understood by those of skill in the art, by contacting a host cell with an agent specific for certain promoters, e.g., by adding IPTG to the media or by switching incubation to a higher temperature. After culturing the bacteria for a further period, generally of between 2 and 24 h, the cells are collected by centrifugation and washed to remove residual media.

D. Viral Vectors

The ability of certain viruses to infect cells or enter cells via receptor mediated endocytosis, and to integrate into host cell genome and express viral genes stably and efficiently have made them attractive candidates for the transfer of foreign nucleic acids into cells (e.g., mammalian cells). Components of the present invention may be a viral vector that encodes one or more CARs of the invention. Non-limiting examples of virus vectors that may be used to deliver a nucleic acid of the present invention are described below.

E. Adenoviral Vectors

A particular method for delivery of the nucleic acid involves the use of an adenovirus expression vector. Although adenovirus vectors are known to have a low capacity for integration into genomic DNA, this feature is counterbalanced by the high efficiency of gene transfer afforded by these vectors. "Adenovirus expression vector" is meant to include those constructs containing adenovirus sequences sufficient to (a) support packaging of the construct and (b) to ultimately express a tissue or cell specific construct that has been cloned therein. Knowledge of the genetic organization or adenovirus, a 36 kb, linear, double stranded DNA virus, allows substitution of large pieces of adenoviral DNA with foreign sequences up to 7 kb (Grunhaus and Horwitz, 1992).

F. AAV Vectors

The nucleic acid may be introduced into the cell using adenovirus assisted transfection. Increased transfection efficiencies have been reported in cell systems using adenovirus coupled systems (Kelleher and Vos, 1994; Cotten et al., 1992; Curiel, 1994). Adeno associated virus (AAV) is an attractive vector system for use in the cells of the present invention as it has a high frequency of integration and it can infect nondividing cells, thus making it useful for delivery of genes into mammalian cells, for example, in tissue culture (Muzyczka, 1992) or in vivo. AAV has a broad host range for infectivity (Tratschin et al., 1984; Laughlin et al., 1986; Lebkowski et al., 1988; McLaughlin et al., 1988). Details concerning the generation and use of rAAV vectors are described in U.S. Pat. Nos. 5,139,941 and 4,797,368, each incorporated herein by reference.

G. Retroviral Vectors

Retroviruses are useful as delivery vectors because of their ability to integrate their genes into the host genome, transferring a large amount of foreign genetic material, infecting a broad spectrum of species and cell types and of being packaged in special cell lines (Miller, 1992).

In order to construct a retroviral vector, a nucleic acid (e.g., one encoding the desired sequence) is inserted into the viral genome in the place of certain viral sequences to produce a virus that is replication defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into a special cell line (e.g., by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

Lentiviruses are complex retroviruses, which, in addition to the common retroviral genes gag, pol, and env, contain other genes with regulatory or structural function. Lentiviral vectors are well known in the art (see, for example, Naldini et al., 1996; Zufferey et al., 1997; Blomer et al., 1997; U.S. Pat. Nos. 6,013,516 and 5,994,136). Some examples of lentivirus include the Human Immunodeficiency Viruses: HIV-1, HIV-2 and the Simian Immunodeficiency Virus: SIV. Lentiviral vectors have been generated by multiply attenuating the HIV virulence genes, for example, the genes env, vif, vpr, vpu and nef are deleted making the vector biologically safe.

Recombinant lentiviral vectors are capable of infecting non-dividing cells and can be used for both in vivo and ex vivo gene transfer and expression of nucleic acid sequences. For example, recombinant lentivirus capable of infecting a non-dividing cell wherein a suitable host cell is transfected with two or more vectors carrying the packaging functions, namely gag, pol and env, as well as rev and tat is described in U.S. Pat. No. 5,994,136, incorporated herein by reference. One may target the recombinant virus by linkage of the envelope protein with an antibody or a particular ligand for targeting to a receptor of a particular cell-type. By inserting a sequence (including a regulatory region) of interest into the viral vector, along with another gene which encodes the ligand for a receptor on a specific target cell, for example, the vector is now target-specific.

H. Other Viral Vectors

Other viral vectors may be employed as vaccine constructs in the present invention. Vectors derived from viruses such as vaccinia virus (Ridgeway, 1988; Baichwal and Sugden, 1986; Coupar et al., 1988), sindbis virus, cytomegalovirus and herpes simplex virus may be employed. They offer several attractive features for various mammalian cells (Friedmann, 1989; Ridgeway, 1988; Baichwal and Sugden, 1986; Coupar et al., 1988; Horwich et al., 1990).

I. Delivery Using Modified Viruses

A nucleic acid to be delivered may be housed within an infective virus that has been engineered to express a specific binding ligand. The virus particle will thus bind specifically to the cognate receptors of the target cell and deliver the contents to the cell. A novel approach designed to allow specific targeting of retrovirus vectors was developed based on the chemical modification of a retrovirus by the chemical addition of lactose residues to the viral envelope. This modification can permit the specific infection of hepatocytes via sialoglycoprotein receptors.

Another approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

J. Vector Delivery and Cell Transformation

Suitable methods for nucleic acid delivery for transfection or transformation of cells are known to one of ordinary skill in the art. Such methods include, but are not limited to, direct delivery of DNA such as by ex vivo transfection, by injection, and so forth. Through the application of techniques known in the art, cells may be stably or transiently transformed.

K. Ex Vivo Transformation

Methods for transfecting eukaryotic cells and tissues removed from an organism in an ex vivo setting are known to those of skill in the art. Thus, it is contemplated that cells or tissues may be removed and transfected ex vivo using nucleic acids of the present invention. In particular aspects, the transplanted cells or tissues may be placed into an organism. In certain facets, a nucleic acid is expressed in the transplanted cells.

VIII. Kits

Any of the CD5-CAR compositions described herein may be comprised in a kit. In a non-limiting example, one or more cells for use in cell therapy and/or the reagents to generate one or more cells for use in cell therapy that harbors recombinant expression vectors may be comprised in a kit. Polynucletoides that encodes the CD5-CAR or portions thereof may be included in the kit. The kit components are provided in suitable container means.

Some components of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present invention also will typically include a means for containing the components in close confinement for commercial sale. Such containers may include injection or blow molded plastic containers into which the desired vials are retained.

When the components of the kit are provided in one and/or more liquid solutions, the liquid solution is an aqueous solution, with a sterile aqueous solution being particularly useful. In some cases, the container means may itself be a syringe, pipette, and/or other such like apparatus, from which the formulation may be applied to an infected area of the body, injected into an animal, and/or even applied to and/or mixed with the other components of the kit.

However, the components of the kit may be provided as dried powder(s). When reagents and/or components are provided as a dry powder, the powder can be reconstituted by the addition of a suitable solvent. It is envisioned that the solvent may also be provided in another container means. The kits may also comprise a second container means for containing a sterile, pharmaceutically acceptable buffer and/or other diluent.

In particular embodiments of the invention, cells that are to be used for cell therapy are provided in a kit, and in some cases the cells are essentially the sole component of the kit. The kit may comprise reagents and materials to make the desired cell. In specific embodiments, the reagents and materials include primers for amplifying desired sequences, nucleotides, suitable buffers or buffer reagents, salt, and so forth, and in some cases the reagents include vectors and/or DNA that encodes a CAR as described herein and/or regulatory elements therefor.

In particular embodiments, there are one or more apparatuses in the kit suitable for extracting one or more samples from an individual. The apparatus may be a syringe, scalpel, and so forth.

In some cases of the invention, the kit, in addition to cell therapy embodiments, also includes a second cancer therapy, such as chemotherapy, hormone therapy, and/or immunotherapy, for example. The kit(s) may be tailored to a particular cancer for an individual and comprise respective second cancer therapies for the individual.

IX. Combination Therapy

In certain embodiments of the invention, methods of the present invention for clinical aspects are combined with other agents effective in the treatment of hyperproliferative disease, such as anti-cancer agents. An "anti-cancer" agent is capable of negatively affecting cancer in a subject, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer. More generally, these other compositions would be provided in a combined amount effective to kill or inhibit proliferation of the cell. This process may involve contacting the cancer cells with the expression construct and the agent(s) or multiple factor(s) at the same time. This may be achieved by contacting the cell with a single composition or pharmacological formulation that includes both agents, or by contacting the cell with two distinct compositions or formulations, at the same time, wherein one composition includes the expression construct and the other includes the second agent(s).

Cancer cell resistance to chemotherapy and radiotherapy agents, for example, represents a major problem in clinical oncology. One goal of current cancer research is to find ways to improve the efficacy of chemo- and radiotherapy by combining it with another therapy In the context of the present invention, it is contemplated that the cell therapy could be used similarly in conjunction with chemotherapeutic, radiotherapeutic, or immunotherapeutic intervention. In specific embodiments, the therapy of the present disclosure is given in conjunction with vincristine, prednisone, cyclophosphamide, doxorubicin, L-asparaginase, cytarabine, methotrexate, 6-mercaptopurine, steroids, mitoxantrone. imatinib, dasatinib, ponatinib, Rituximab, Campath, Lenalidomide, Nelarabine, or a combination thereof, for example. In specific embodiments, checkpoint inhibitors are utilized. In certain embodiments, antibodies against or small molecule antagonists of PD-1, PD-L1, and/or CTLA4 may be utilized.

The present inventive therapy may precede or follow the other agent treatment by intervals ranging from minutes to weeks. In embodiments where the other agent and present invention are applied separately to the individual, one would generally ensure that a significant period of time did not expire between the time of each delivery, such that the agent and inventive therapy would still be able to exert an advantageously combined effect on the cell. In such instances, it is contemplated that one may contact the cell with both modalities within about 12-24 h of each other and, more preferably, within about 6-12 h of each other. In some situations, it may be desirable to extend the time period for treatment significantly, however, where several d (2, 3, 4, 5, 6 or 7) to several wk (1, 2, 3, 4, 5, 6, 7 or 8) lapse between the respective administrations.

Various combinations may be employed, present invention is "A" and the secondary agent, such as radio- or chemotherapy, is "B":

A/B/A B/A/B B/B/A A/A/B A/B/B B/A/A A/B/B/B B/A/B/B

B/B/B/A B/B/A/B A/A/B/B A/B/A/B A/B/B/A B/B/A/A B/A/B/A B/A/A/B A/A/A/B B/A/A/A A/B/A/A A/A/B/A

It is expected that the treatment cycles would be repeated as necessary. It also is contemplated that various standard therapies, as well as surgical intervention, may be applied in combination with the inventive cell therapy.

A. Chemotherapy

Cancer therapies also include a variety of combination therapies with both chemical and radiation based treatments.

Combination chemotherapies include, for example, vincristine, prednisone, cyclophosphamide, doxorubicin, L-asparaginase, cytarabine, methotrexate, 6-mercaptopurine, steroids, mitoxantrone. imatinib, dasatinib, ponatinib, or a combination thereof, or any analog or derivative variant of the foregoing and also combinations thereof.

In specific embodiments, chemotherapy for the individual is employed in conjunction with the invention, for example before, during and/or after administration of the invention.

B. Radiotherapy

Other factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

C. Immunotherapy

Immunotherapeutics generally rely on the use of immune effector cells and molecules to target and destroy cancer cells. In specific embodiments the immunotherapy is a different immunotherapy than that of the present disclosure. The additional immunotherapy may or may not target CD5, as with the present disclosure. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Immunotherapy other than the inventive therapy described herein could thus be used as part of a combined therapy, in conjunction with the present cell therapy. The general approach for combined therapy is discussed below. Generally, the tumor cell must bear some marker that is amenable to targeting, i.e., is not present on the majority of other cells. Many tumor markers exist and any of these may be suitable for targeting in the context of the present invention.

In specific embodiments, the immunotherapy for use with the methods of the present disclosure is Rituximab.

D. Genes

In yet another embodiment, the secondary treatment is a gene therapy in which a therapeutic polynucleotide is administered before, after, or at the same time as the present invention clinical embodiments. A variety of expression products are encompassed within the invention, including inducers of cellular proliferation, inhibitors of cellular proliferation, or regulators of programmed cell death.

E. Surgery

In some embodiments, the cancer is a solid tumor and requires surgery. Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and miscopically controlled surgery (Mohs' surgery). It is further contemplated that the present invention may be used in conjunction with removal of superficial cancers, precancers, or incidental amounts of normal tissue.

Upon excision of part of all of cancerous cells, tissue, or tumor, a cavity may be formed in the body. Treatment with embodiments of the disclosure may be accomplished by perfusion, direct injection or local application of the area with an additional anti-cancer therapy, such as during and/or following the excision. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

F. Other Agents

It is contemplated that other agents may be used in combination with the present invention to improve the therapeutic efficacy of treatment. These additional agents include immunomodulatory agents, agents that affect the upregulation of cell surface receptors and GAP junctions, cytostatic and differentiation agents, inhibitors of cell adhesion, or agents that increase the sensitivity of the hyperproliferative cells to apoptotic inducers. Immunomodulatory agents include tumor necrosis factor; interferon alpha, beta, and gamma; IL-2 and other cytokines; F42K and other cytokine analogs; or MIP-1, MIP-lbeta, MCP-1, RANTES, and other chemokines, for example. It is further contemplated that the upregulation of cell surface receptors or their ligands such as Fas/Fas ligand, DR4 or DR5/TRAIL would potentiate the apoptotic inducing abililties of the present invention by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents can be used in combination with the present invention to improve the anti-hyerproliferative efficacy of the treatments. Inhibitors of cell adhesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present invention to improve the treatment efficacy.

EXAMPLE 1

CD5 CAR for T-Cell Malignancies

Chimeric antigen receptors (CARs) have emerged as a powerful therapeutic tool redirecting patient's own T cells to treat hematologic malignancies—in particular, those of B cell origin. However, T cell malignancies remain a more challenging task for CAR T cells owing to the shared expression of targetable tumor-associated antigens, e.g., CD5, between normal and cancerous T cells, potentially invoking fratricide of CAR T cells.

The present disclosure provides a novel CAR targeting CD5, a common marker expressed in most T-cell leukemia/lymphoma blasts and normal T cells. As described below, upon transduction with a CD5 CAR, T cells displayed limited and transient fratricide and eventually acquired resistance to self-killing. Expansion of CD5 CAR T cells coincided with downregulation of CD5 from the cell surface. At the same time, CD5 CAR T cells efficiently recognized and completely eliminated CD5-positive T-ALL and T cell lymphoma cell lines in vitro. Moreover, CD5 CAR T cells dramatically suppressed systemic in vivo disease progression in xenograft mouse models. Importantly, CD5 CAR T cells demonstrated significant cytotoxicity against primary T-ALL cells, showcasing the therapeutic utility of CD5 CAR for patients with T-cell malignancies. As described herein for the first time, CD5 CAR can redirect normal T cells to eliminate CD5-positive malignant T-cells while producing only limited fratricide.

EXAMPLE 2

A T Cell-Directed Chimeric Antigen Receptor for the Selective Treatment of T Cell Malignancies Lymphoid malignancies produce significant morbidity and mortality in pediatric and adult patients (Dores, et al., 2012). Although recent advances in chemotherapy have improved disease-free survival, prognosis remains poor for primary chemotherapy-refractory or relapsed patients, and all patients may have significant short-term and long-term toxicities from their treatment (Kantarjian, et al., 2010; Gökbuget, et al., 2012; DeAngelo, et al., 2007; Goldberg, et al., 2003; Oudot, et al., 2008; O'Brien, et al., 2008). Recent studies in patients with B lymphoid malignancies have demonstrated the remarkable potency of chimeric antigen receptors (CARs) that can redirect T cells to the CD19 antigen present on normal and malignant B cells with complete response rates of >90% even in patients with refractory or relapsed disease (Brentjens, et al., 2013; Maude, et al., 2014). Such response rates, however, are accompanied by elimination of the normal B cell population. The concern that loss of normal T lymphocytes would produce a more profound immunodeficiency than loss of B cells has impeded parallel approaches that would treat T-cell malignancies by targeting an antigen consistently expressed by both normal and malignant T cells. Moreover, any CAR-T cell that targeted a tumor antigen shared between normal and malignant T cells might lead to fratricide of CAR T cells, thus jeopardizing their therapeutic efficacy.

CD5 is one of the characteristic surface markers of malignant T cells, present in ~80% of T cell acute lymphoblastic leukemia (T-ALL) and T cell lymphomas (Campana, et al., 1991; Pui, et al., 1993). In addition, CD5 is often expressed in B-CLL and mantle cell lymphoma. Expression of CD5 by normal cells is restricted to components of the immune system: thymocytes, peripheral T cells and a minor subpopulation of B lymphocytes (B-1 cells) (Berland & Wortis, 2002; Jones, et al., 1986). CD5 is a negative regulator of TCR signaling (Brossard, et al., 2003; Perez-Villar, et al., 1999; Bamberger, et al., 2011) implicated in promoting survival of normal and malignant human lymphocytes (Gary-Gouy, et al., 2007; Friedlein, et al., 2007; Gary-Gouy, et al., 2002; Ryan, et al., 2005), and was validated as a tumor target antigen in earlier clinical trials using immunotoxin-conjugated CD5 antibodies (Bertram, et al., 1986; LeMaistre, et al., 1991; Kernan, et al., 1984). These clinical trials demonstrated efficient depletion of malignant T cells in patients with cutaneous T cell lymphoma and T-ALL.

CD5 CAR-Transduced T Cells Expand and Downregulate CD5 from Cell Surface.

Figure 1B:
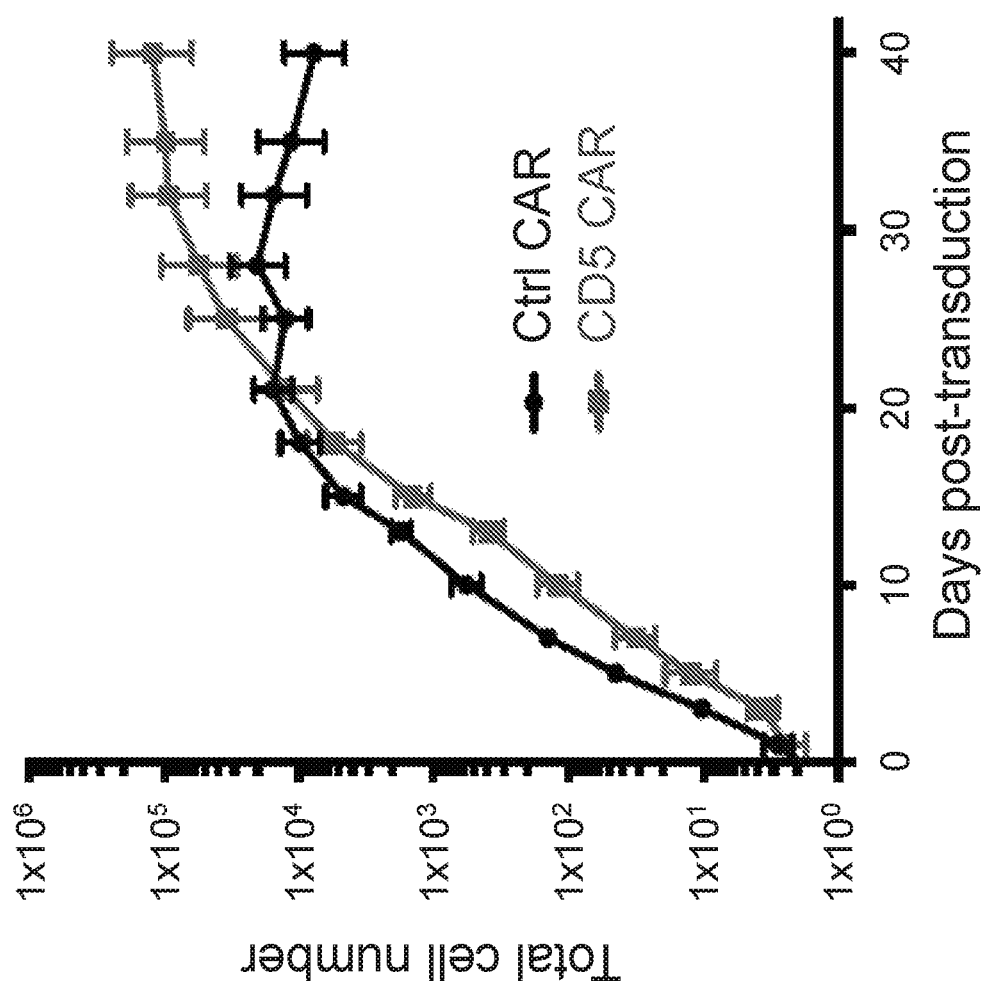

A CD5 CAR was designed comprising anti-CD5 scFv (derived from clone H65 (Kernan et al., 1984)), an IgG Fc spacer and intracellular signaling domains from CD28 and TCR zeta chain (FIG. 1A). After transduction, both CD4+ and CD8+ T cells expressed the CD5 CAR (FIG. 1A). Initial expansion of CD5 CAR-transduced T cells was delayed by 2-3 days due to transient fratricide but subsequent expansion superseded that of T cells transduced with a control CD19 CAR (FIG. 1B).

Figure 1C:
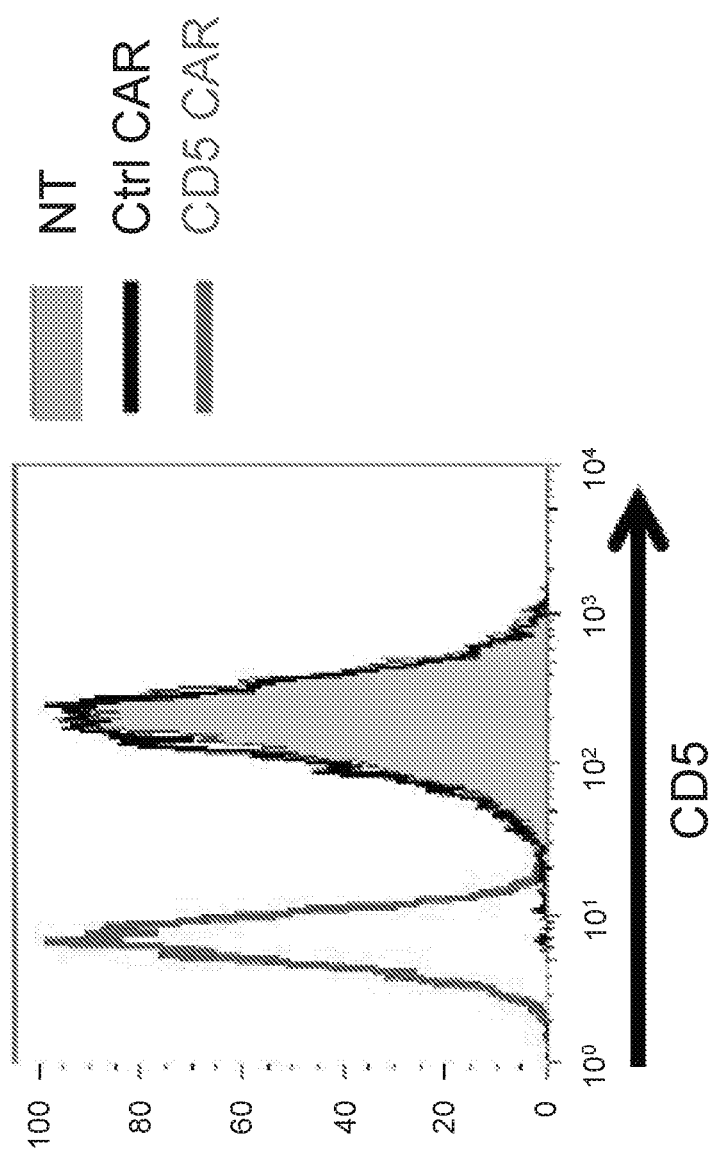
Figure 1D:
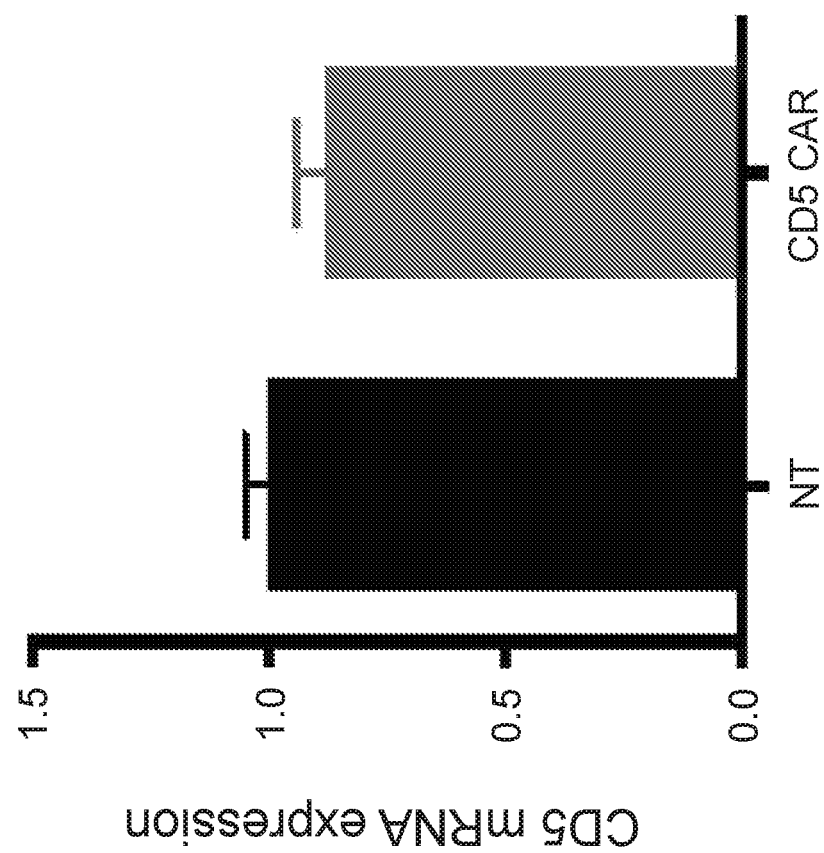
Figure 7:
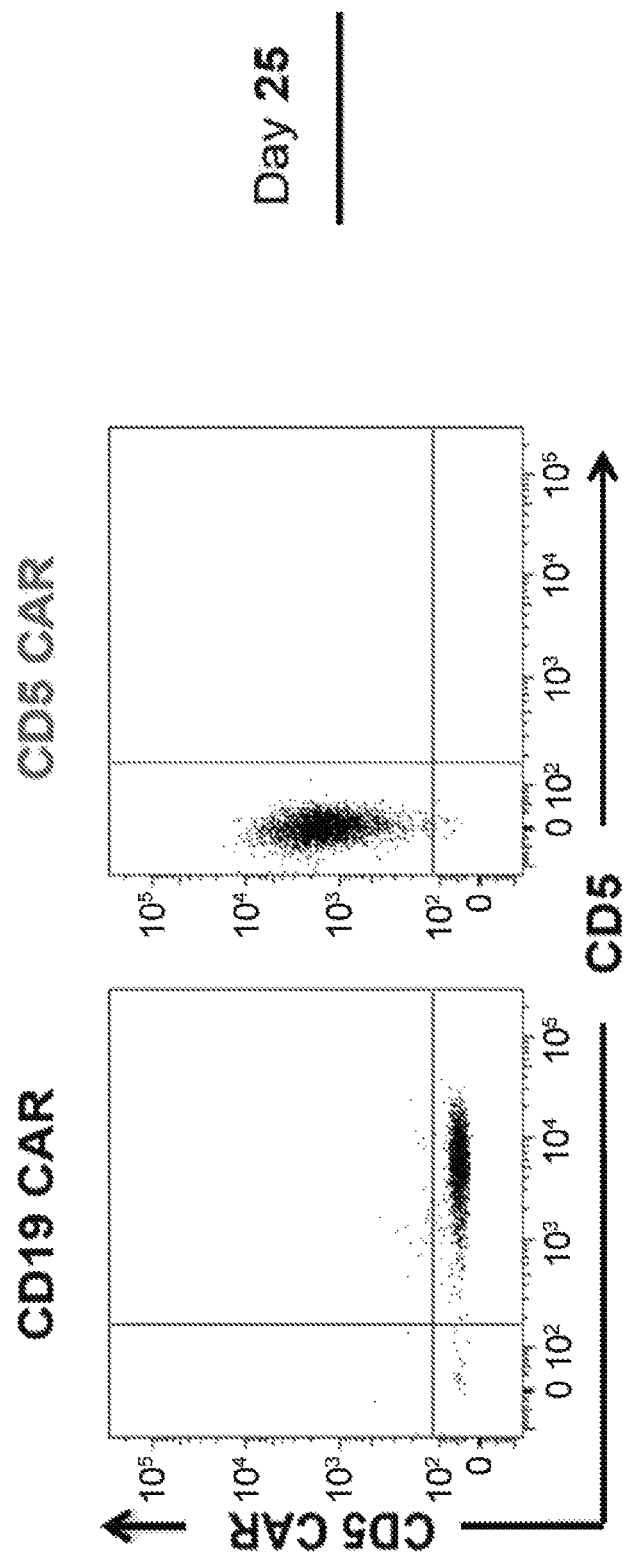
FIG. 7—Long-term expression of CD5 CAR in T cells. Surface staining of CD5 CAR (anti-IgG Fc) and CD5 antigen in activated T cells transduced with CD5 CAR or CD19 CAR 25 days prior. Data from one representative donor are shown (n=4).

Expression of CD5 CAR in T cells was stable for >25 days post-transduction (FIG. 7). CAR expression was associated with loss of CD5 expression (FIG. 1C), possibly facilitating expansion of CD5 CAR T cells and limiting fratricide. Loss of surface CD5 expression was not a result of preferential survival of CD5-negative T cells as overall transcription of CD5 gene was intact (FIG. 1D), meaning CD5 downregulation occurred at the translational and/or post-translational level.

CD5 CAR T Cells Demonstrate Limited and Transient Fratricide.

Figure 2A:
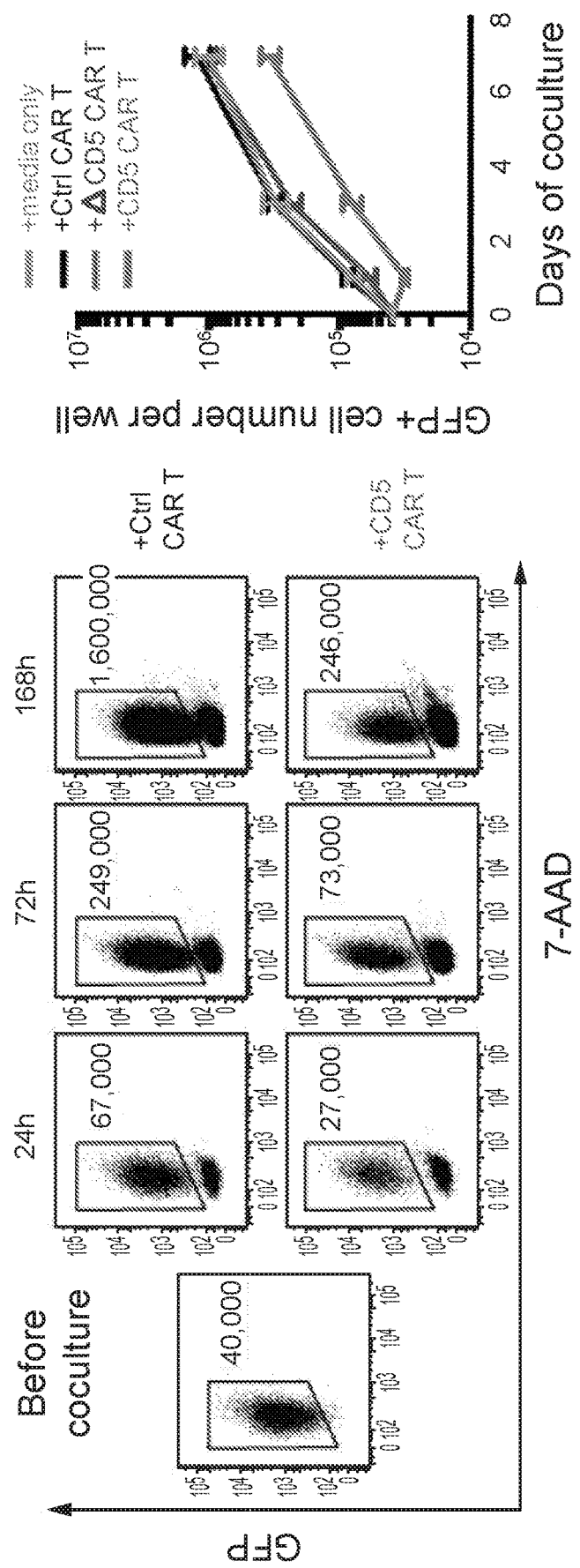
FIG. 2A-2D—CD5 CAR T cells produce limited fratricide and spare VSTs.

To assess the extent of fratricide among CD5 CAR T cells against autologous T cells, expansion was compared of autologous GFP$^+$ activated T cells co-cultured with CD5 CAR- or control CAR-transduced T cells for 7 days. There was a transient decline in the number of autologous GFP$^+$ T cells after 24 h of co-culture with CD5 CAR T cells followed by sustained expansion (FIG. 2A). As expected, autologous T cells expanded in co-culture with T cells transduced with either control CAR or truncated CD5 CAR (ΔCD5 CAR, lacking cytoplasmic activation domains) (FIG. 2A).

Figure 2B:
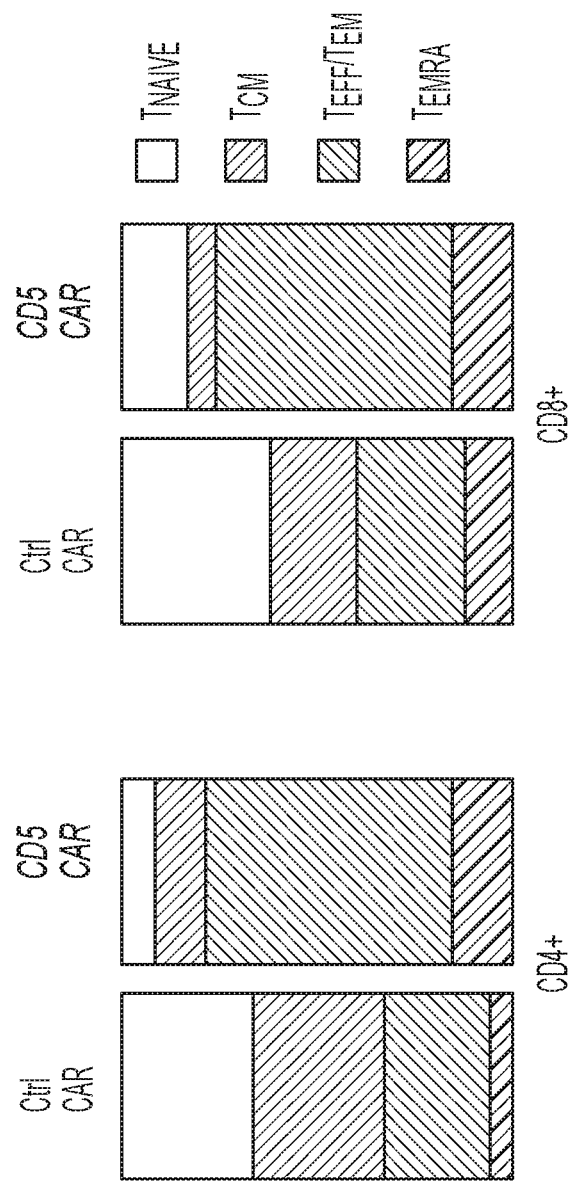
Figures 1, 2C:
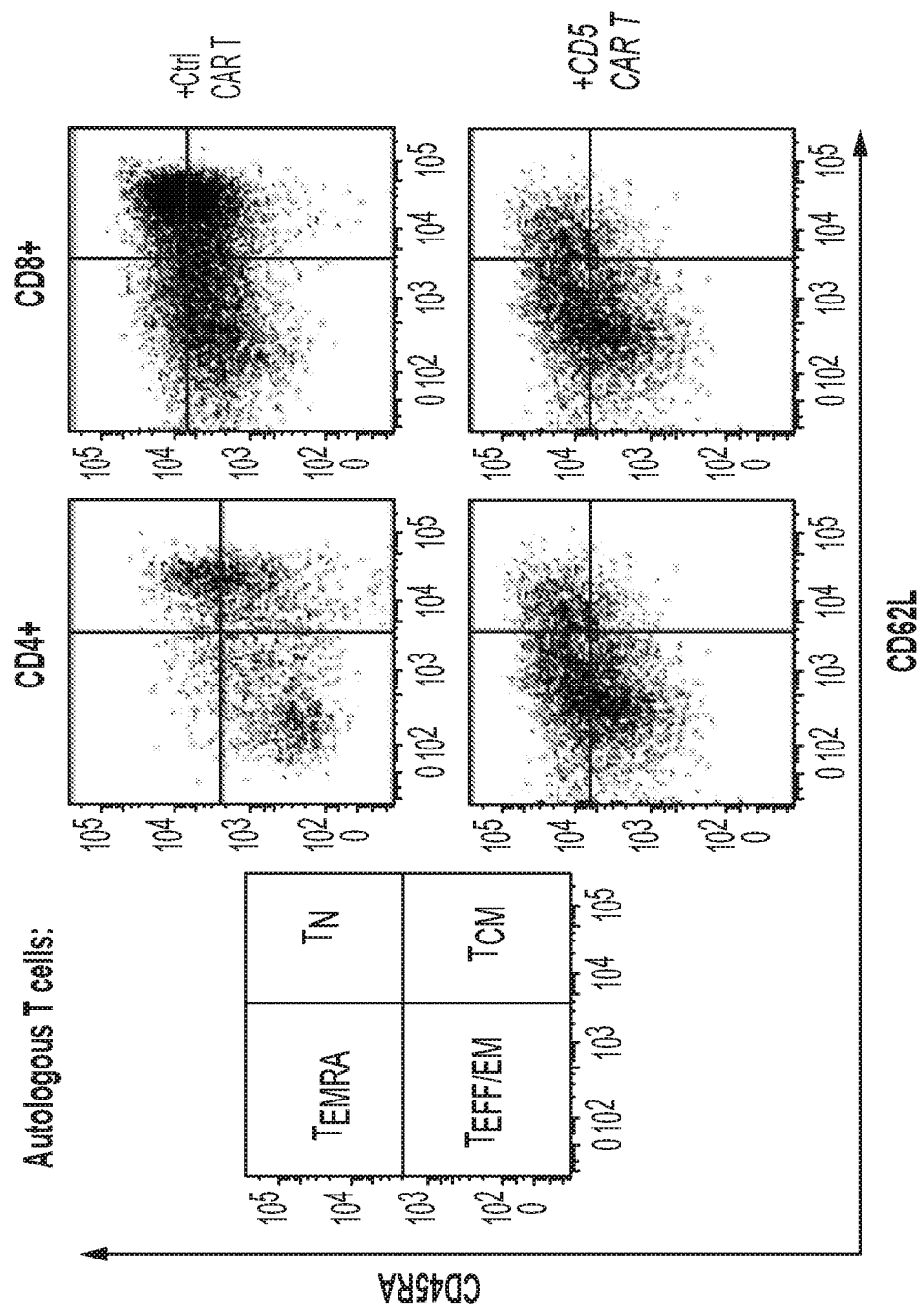
Figures 2, 2C:
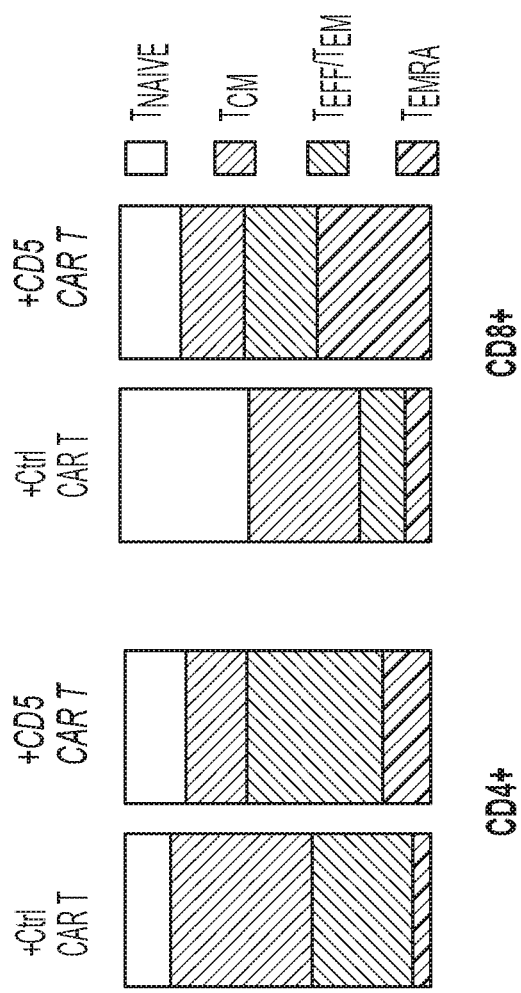

Following expansion, CD5 CAR T cells were enriched for effector and effector memory cells (CD45RA$^-$ CD62L$^{low}$) compared with T cells transduced with a control CAR (FIG. 2B). To discover whether the prevalence of CD62L$^{low}$ effector and effector memory populations in CD5 CAR T cells results from preferential survival of those subsets during the initial period of fratricide, the phenotype was analyzed of autologous T cells co-cultured with CD5 CAR T cells for 24 h to identify populations that were preferentially targeted by CD5 CAR T cells. Fratricide was primarily directed against CD62$^{high}$ central memory and naïve-phenotype GFP$^+$ T cells, resulting in preferential survival of CD62L$^{low}$ effector and effector memory T cells (FIG. 2C). The combined mean frequency of effector and effector memory phenotype cells among autologous T cells increased from 23% to 61% in CD8$^+$ cells and from 40% to 60% in the CD4$^+$ subset, with a proportional decrease in the prevalence of naïve and central memory phenotype cells. This activity mirrors the effector-enriched phenotype of CD5 CAR T cells (FIG. 2B), and parallels the intrinsically enhanced resistance of those subsets to other routes of self-directed cytotoxicity (Sun, et al., 1996; Balaji, et al., 2002).

It was determined if selective fratricide by CD5 CAR T cells would eliminate virus-specific T cells (VSTs) and thus potentially compromise anti-viral immunity. Autologous GFP$^+$ T cells were co-cultured with CD5 CAR T cells for 72 h, then purified GFP$^+$ T cells by cell sorting, and IFNγ

Figure 2D:
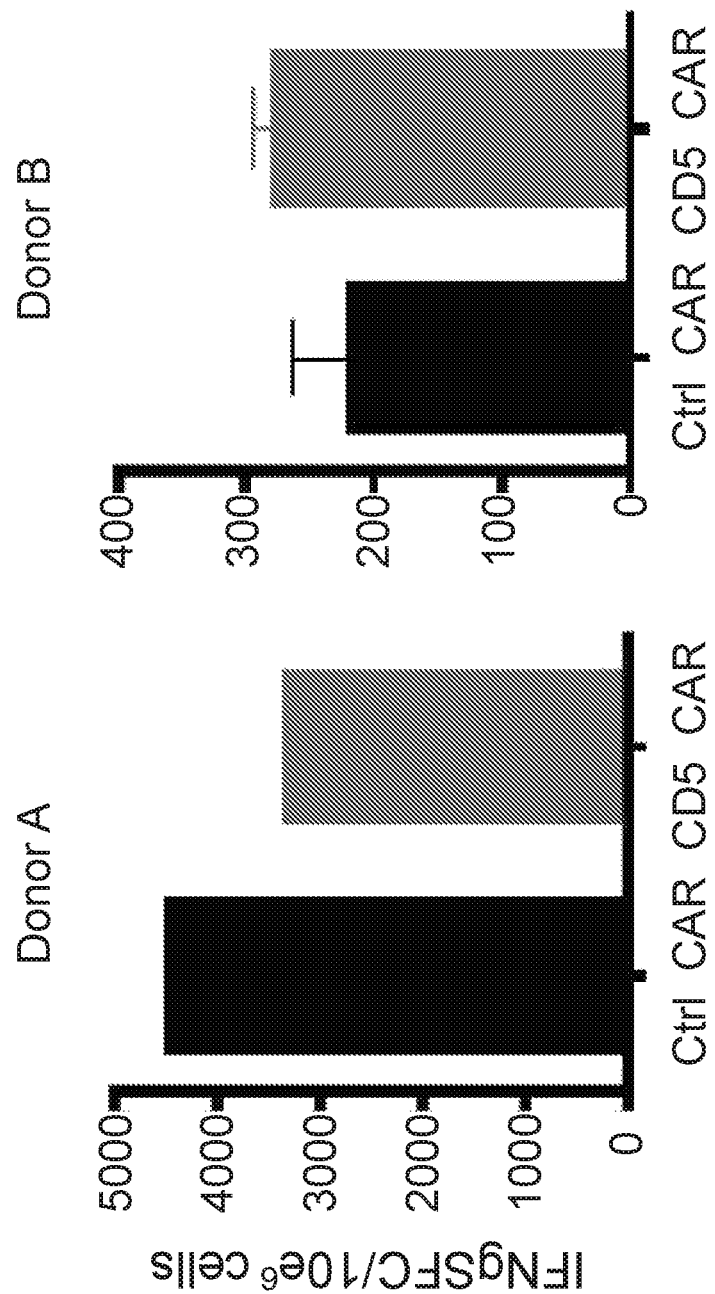

ELISpot was used to analyze the frequency of T cells reactive to a pool of peptide antigens derived from Cytomegalovirus, Epstein-Barr Virus and Adenoviruses. There was no significant change in the frequency of tri-virus-specific autologous T cells after co-culture with CD5 CAR T cells compared with control CAR (FIG. 2D). These data demonstrate that the limited and transient fratricide of CD5 CAR T cells does not preclude expansion of VSTs.

CD5 CAR T Cells Effectively Recognize and Eliminate Malignant T Cell Lines In Vitro.

Figure 3A:
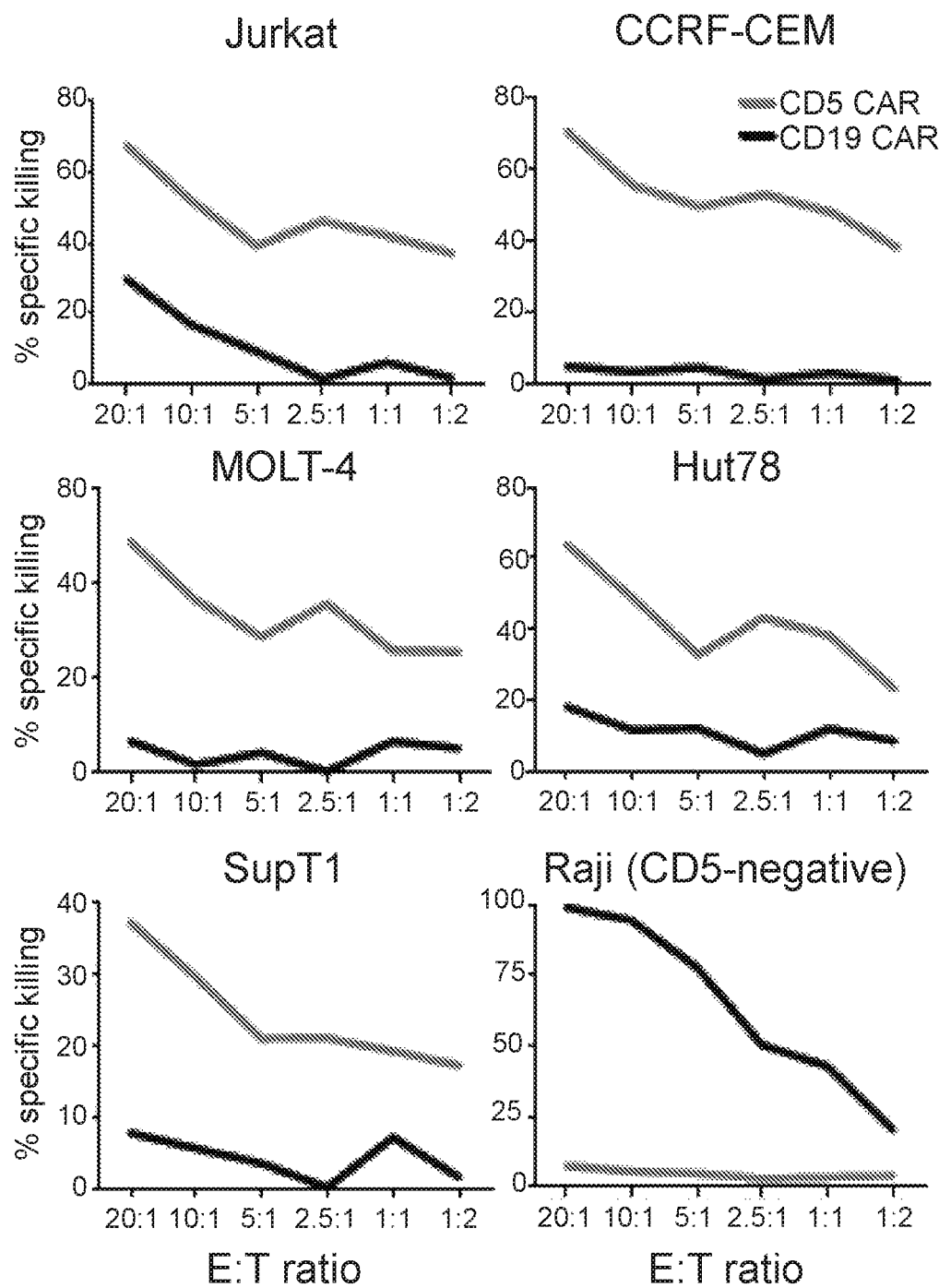
FIG. 3A-3D—CD5 CAR T cells eliminate malignant T cells in vitro.
Figures 1, 3B:
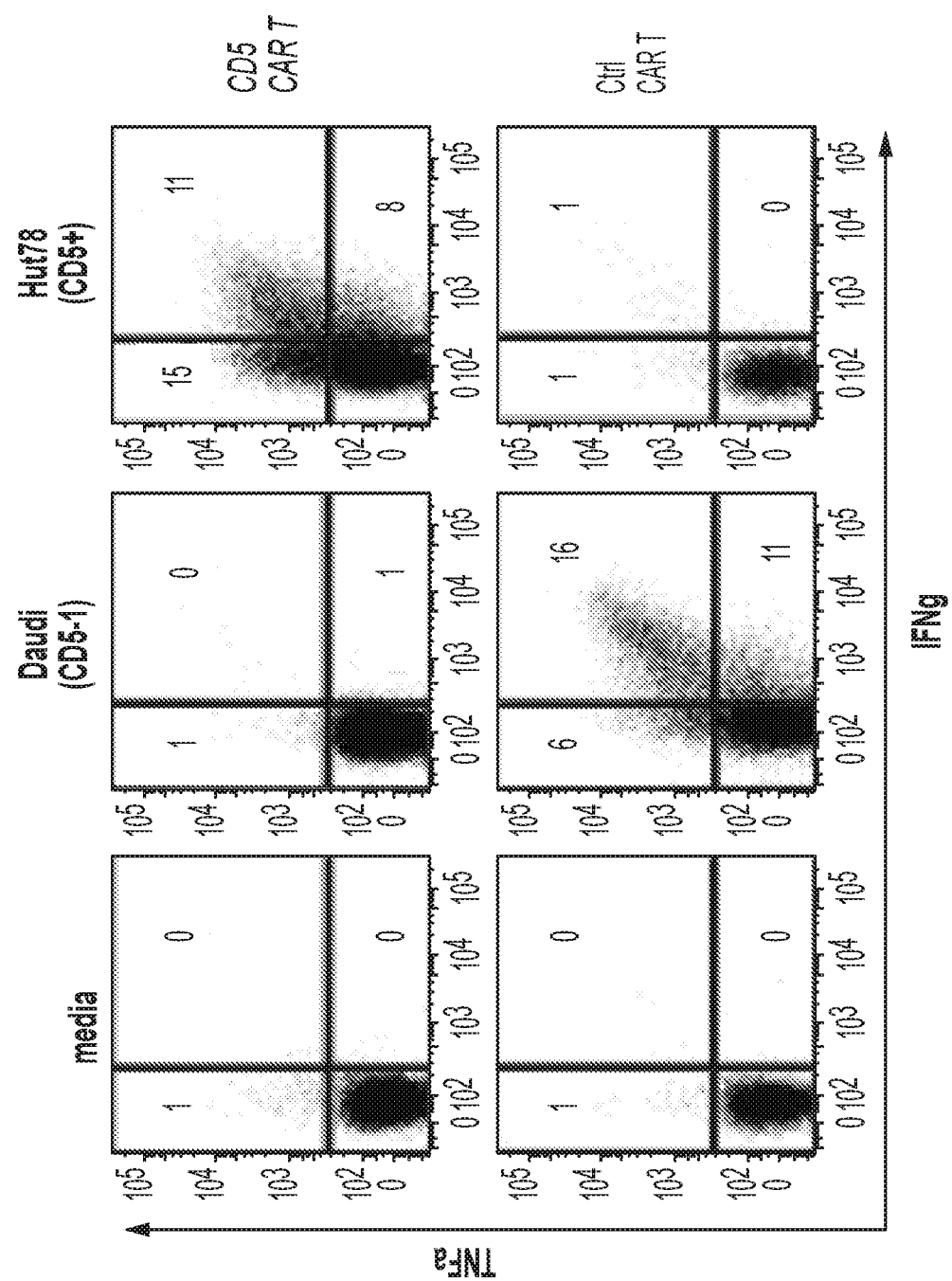
Figures 2, 3B:
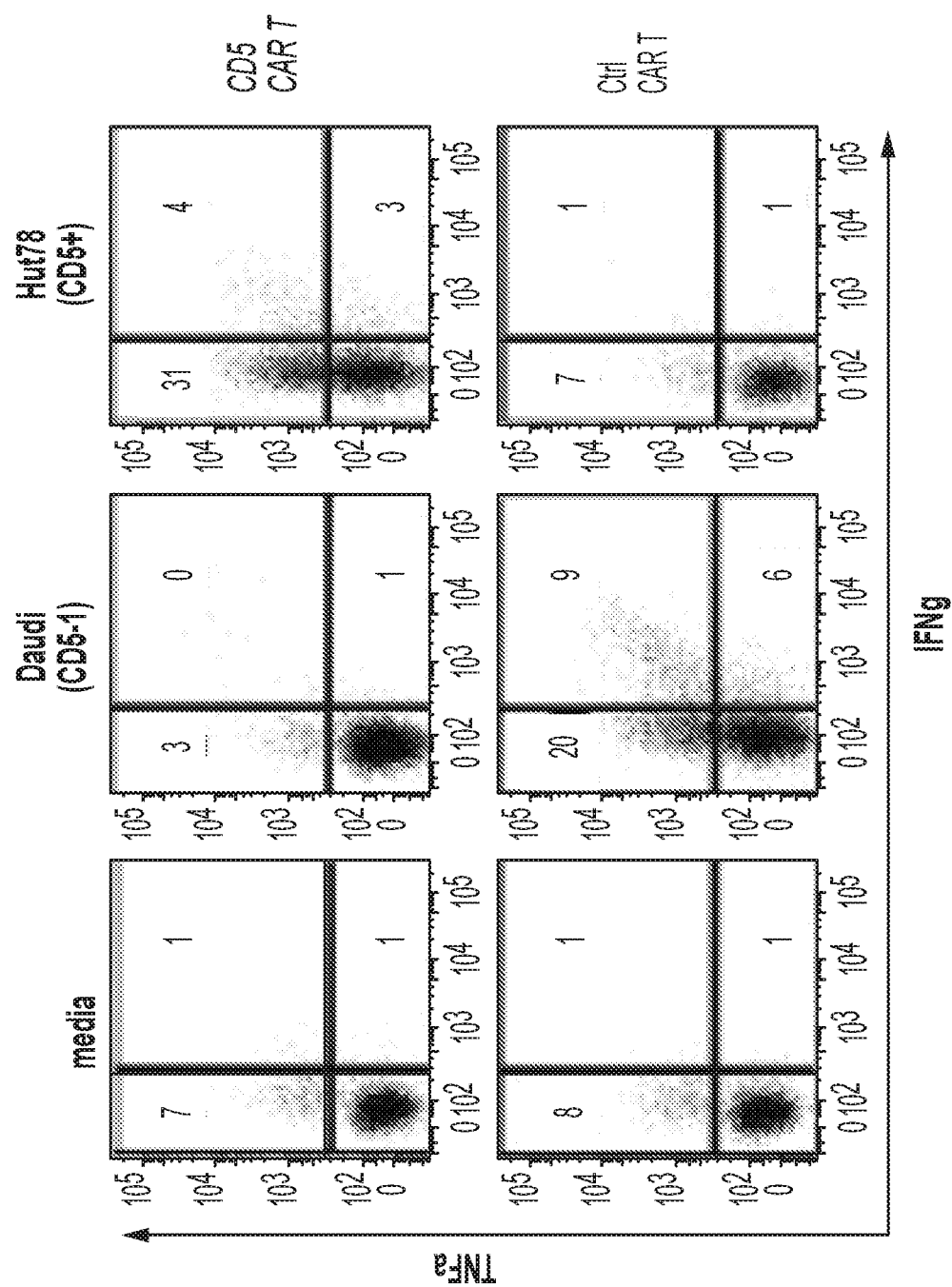
Figures 3, 3B:
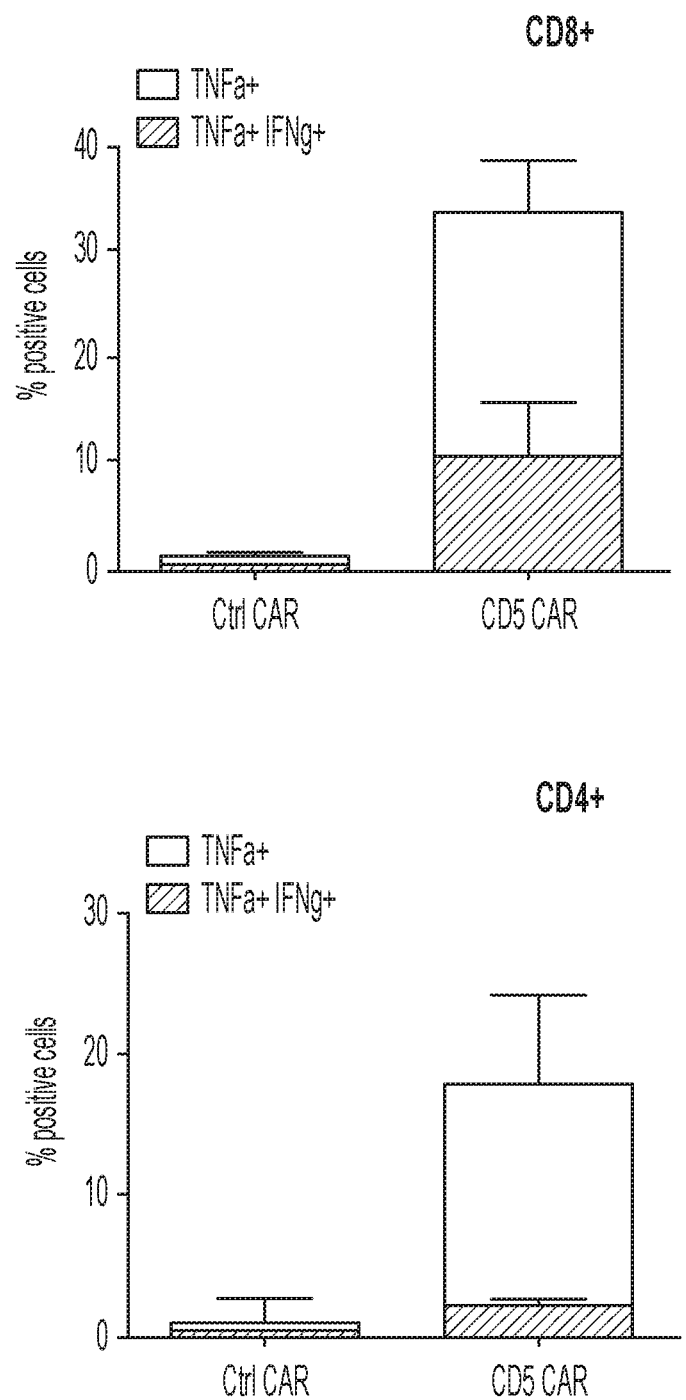

The capacity of CD5 CAR T cells to eradicate CD5$^+$ T-ALL and T lymphoma cell lines was evaluated. Compared to control CD19 CAR T cells, CD5 CAR T cells demonstrated significant cytotoxicity against 5 different T cell lines: Jurkat, CCRF-CEM, MOLT4, Hut78 and SupT1 (FIG. 3A). At the same time, the CD5$^-$ B cell line Raji was not recognized by CD5 CAR T cells (FIG. 3A), indicating the selectivity of the CD5 CAR T cells. Both CD4$^+$ and CD8$^+$ CD5 CAR T cells had significant production of IFNγ and TNFα when co-cultured with CD5$^+$ target cells Hut78, but not with the CD5$^-$ B cell line Daudi (FIG. 3B).

Figures 1, 3C:
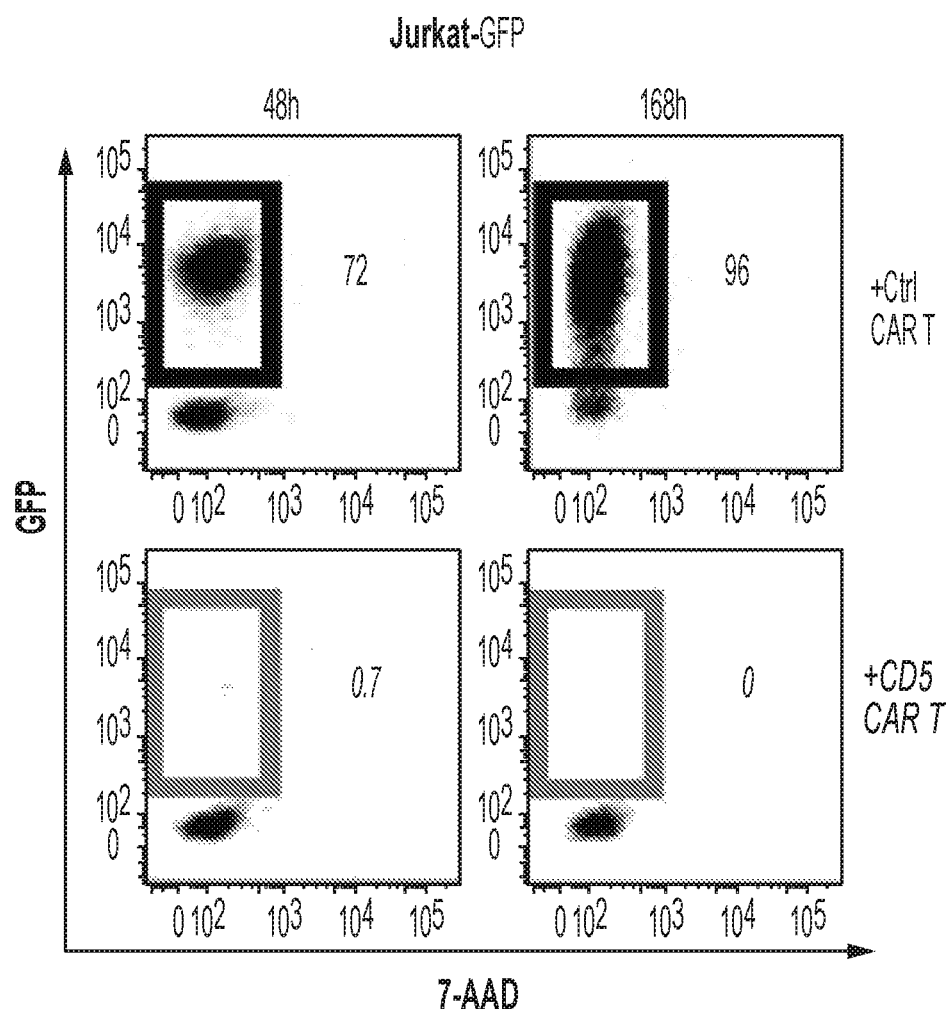
Figures 2, 3C:
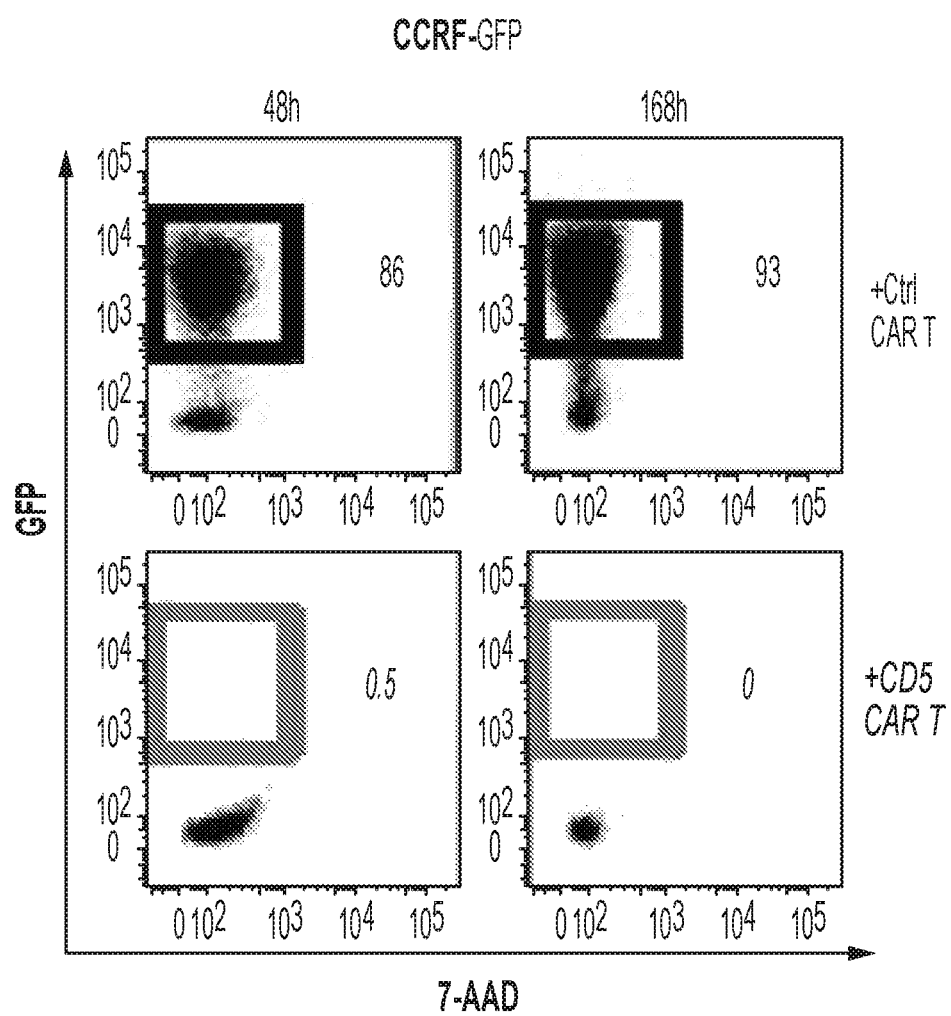
Figures 3, 3C:
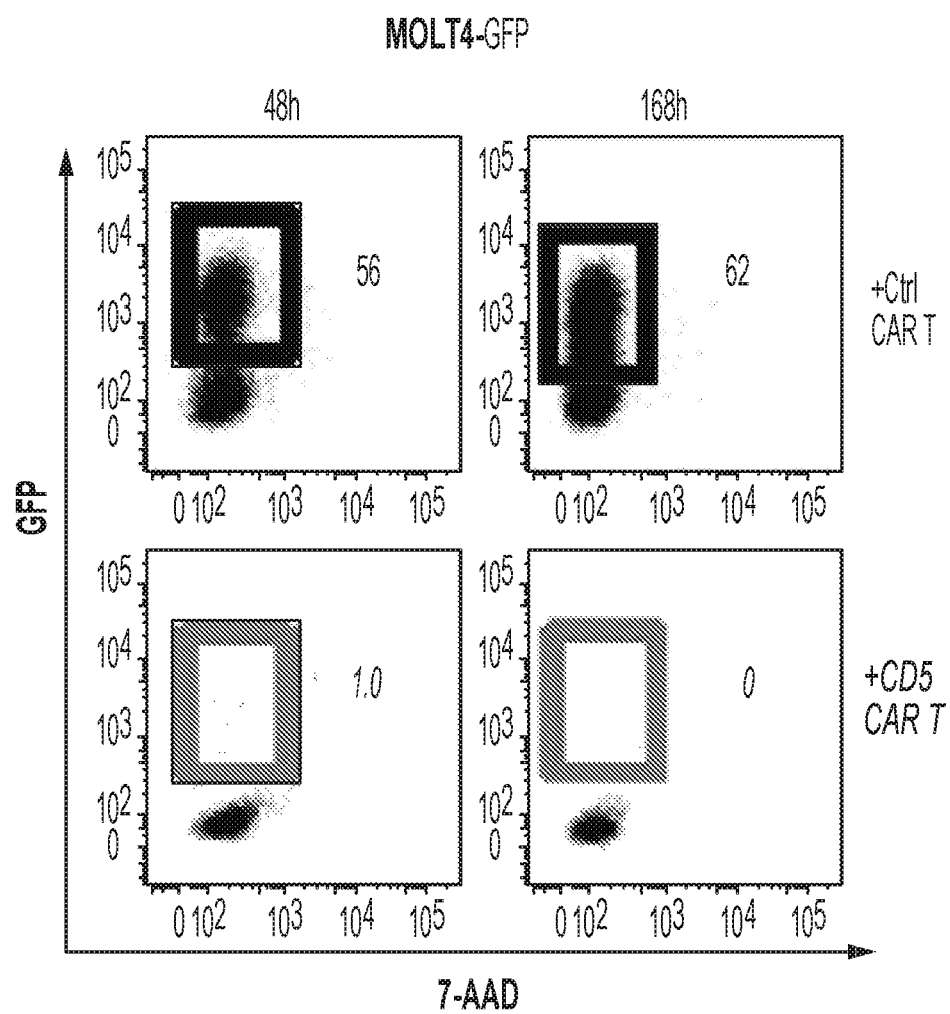
Figure 8:
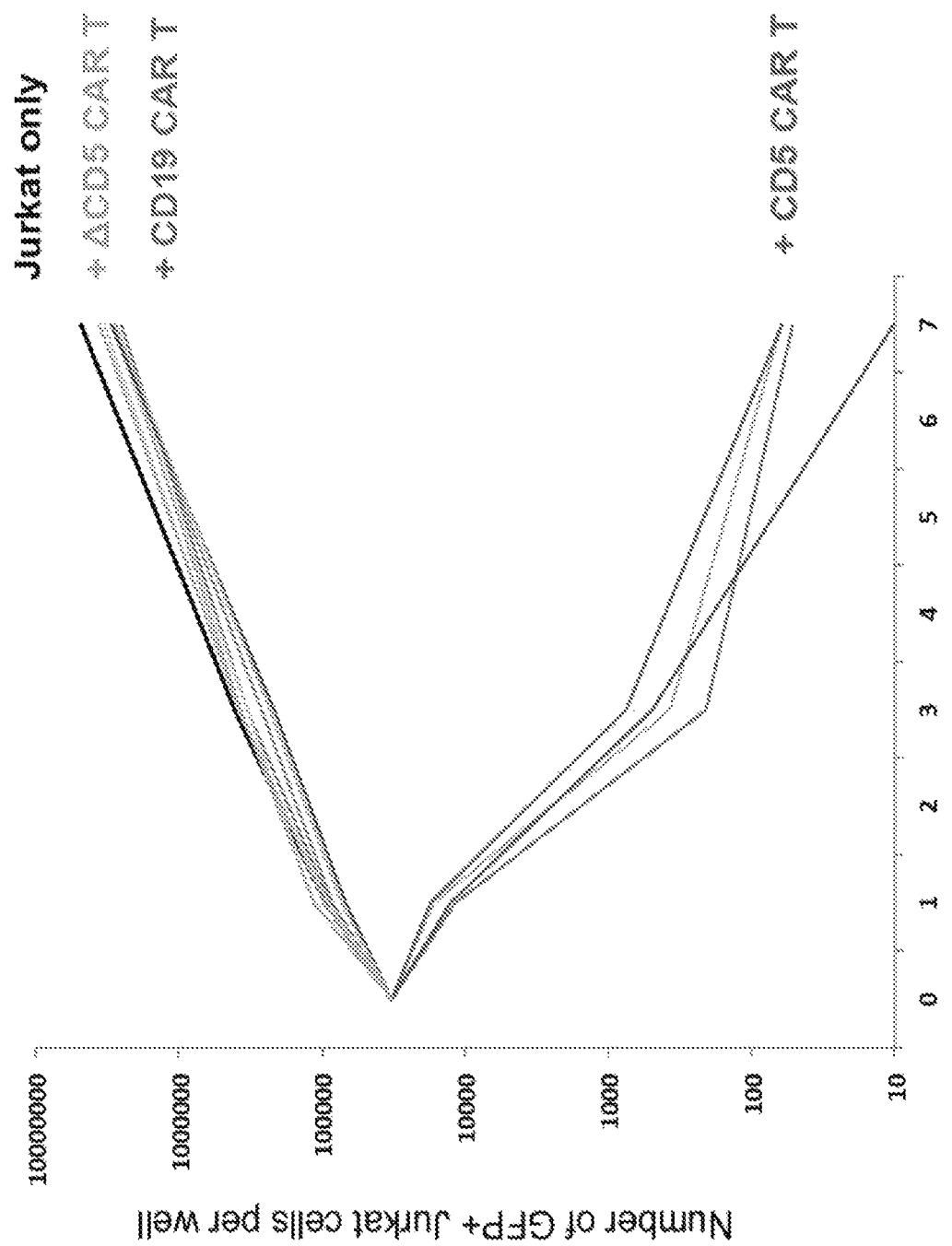
FIG. 8—Cytotoxicity of CD5 CAR T cells against Jurkat upon long co-culture. Jurkat-GFP cells were plated with T cells transduced with full-length CD5 CAR (red lines), CD19 CAR (blue lines) or truncated CD5 CAR (ΔCD5 CAR, yellow lines) at 1:4 E:T ratio, or without T cells (black line). Number of viable GFP+ target cells per well was calculated 1, 3 and 7 days after plating by flow cytometry using CountBright beads and 7-AAD staining. Lines represent individual donors (n=4).

To assess the ability of CD5 CAR T cells to suppress tumor cell line growth in longer co-culture, CAR T cells were co-cultured with GFP-expressing Jurkat, CCRF or MOLT4 cells and the survival of the target cells at multiple time points was analyzed. CD5 CAR T cells effectively eliminated >95% of target cells after 48 h (FIG. 3C), and after 7 days of co-culture, no measurable target cells remained (FIGS. 3C and 8). Unlike normal T cells, therefore, the malignant T cell lines were highly susceptible to CD5 CAR T cells.

Figure 3D:
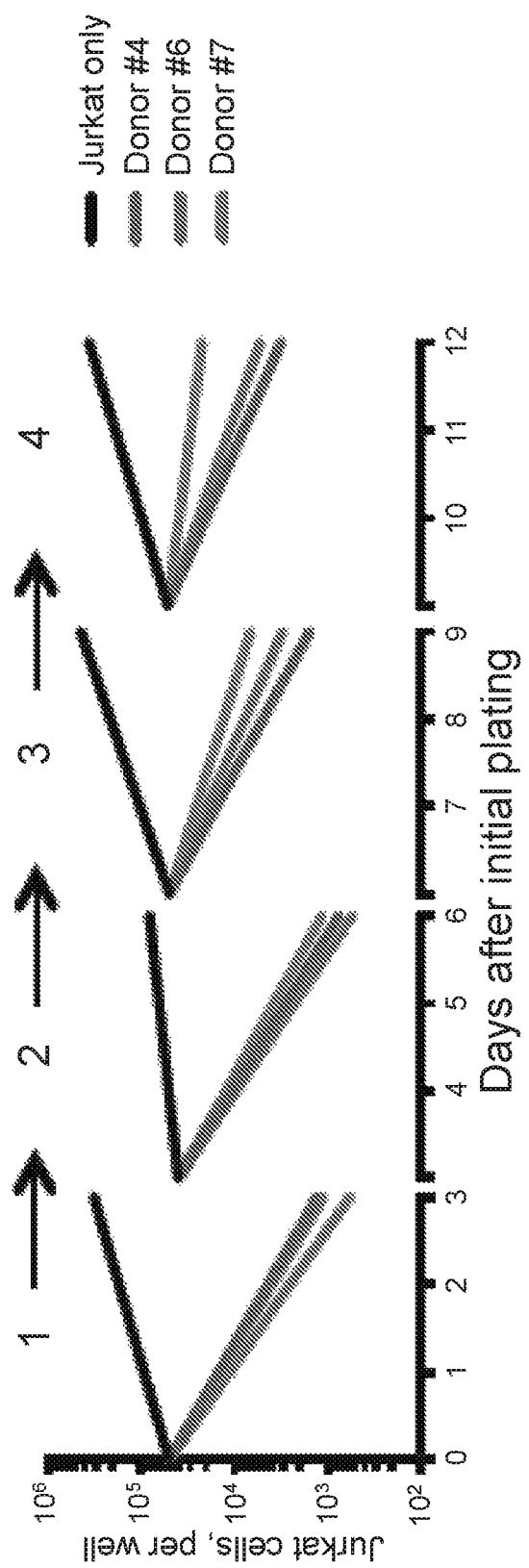

The effectiveness of cytotoxic T cell therapy likely requires the effector cells to sequentially kill multiple target cells. Therefore, the capacity was tested of CD5 CAR T cells to eliminate tumor cells in a sequential killing assay, in which fresh Jurkat cells were added to CD5 CAR T cells every 3 days to restore an effector-to-target ratio of 1:2. CD5 CAR T cells could eradicate freshly replenished Jurkat cells for at least 4 iterations (FIG. 3D).

Mechanisms of Differential Killing of Normal and Malignant T Cells.

Figure 9A:
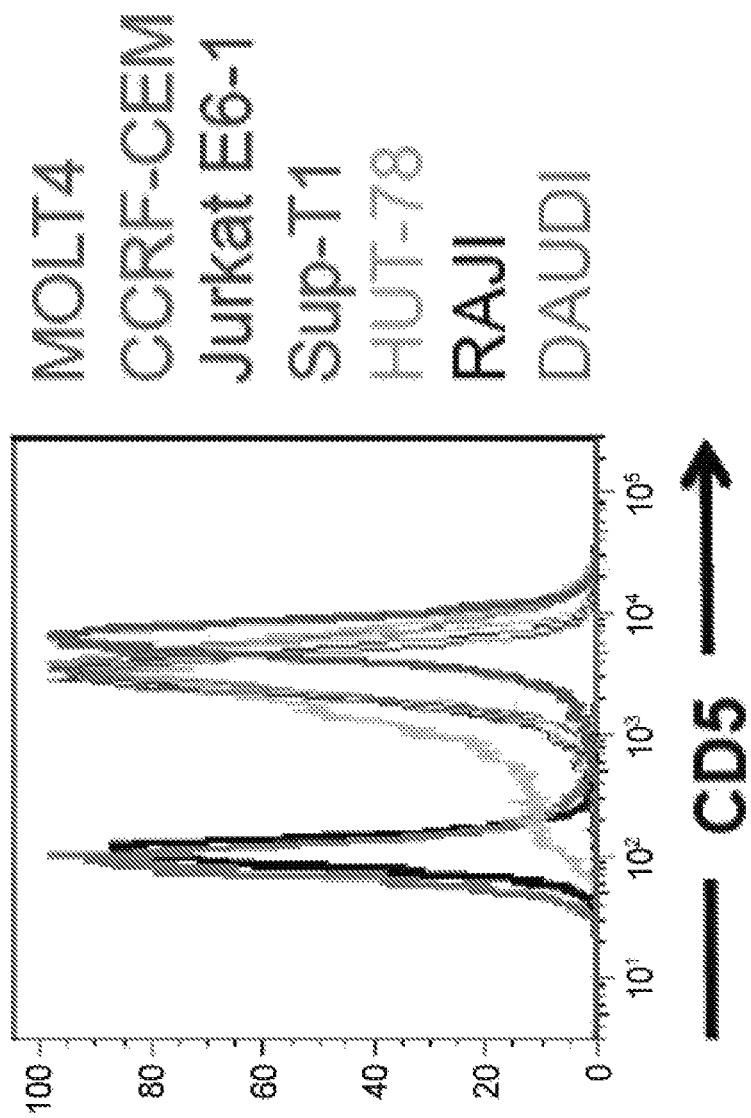
FIGS. 9A-9D—Surface expression of CD5 in T-ALL cell lines in resting state and upon co-culture with CD5 CAR T cells.
Figure 9B:
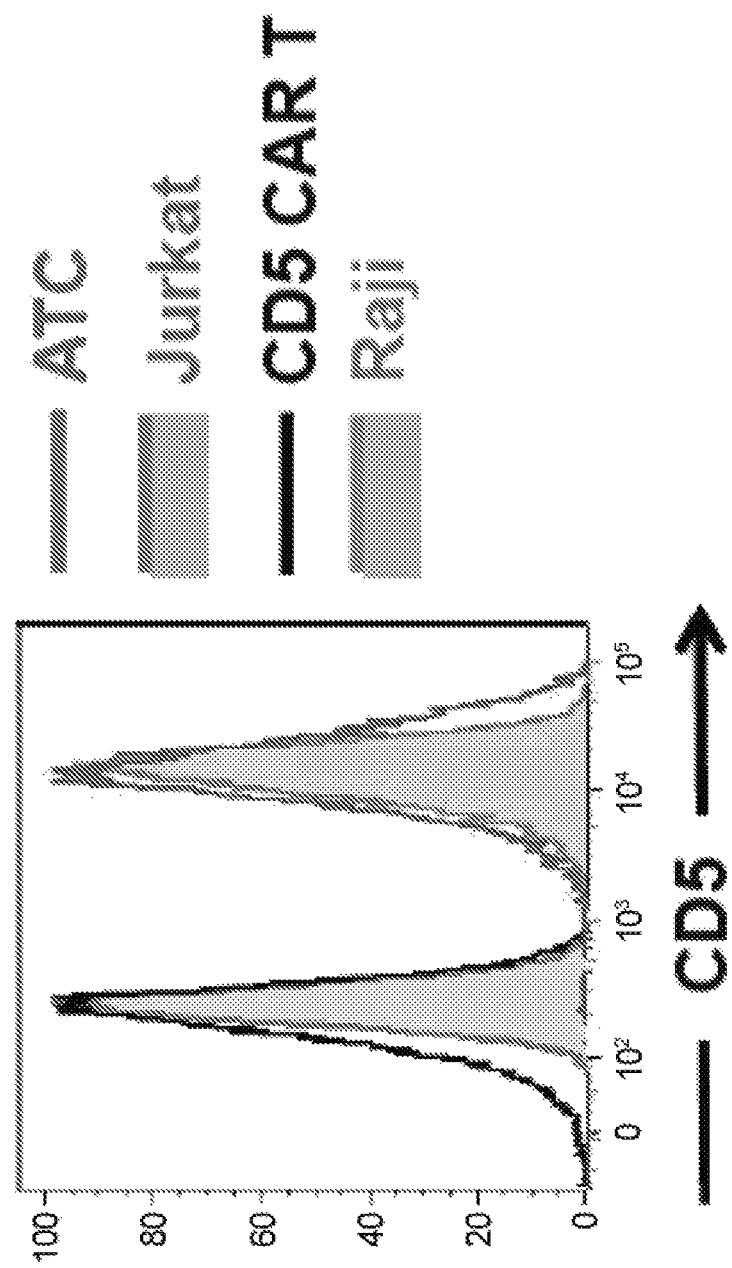
Figure 9C:
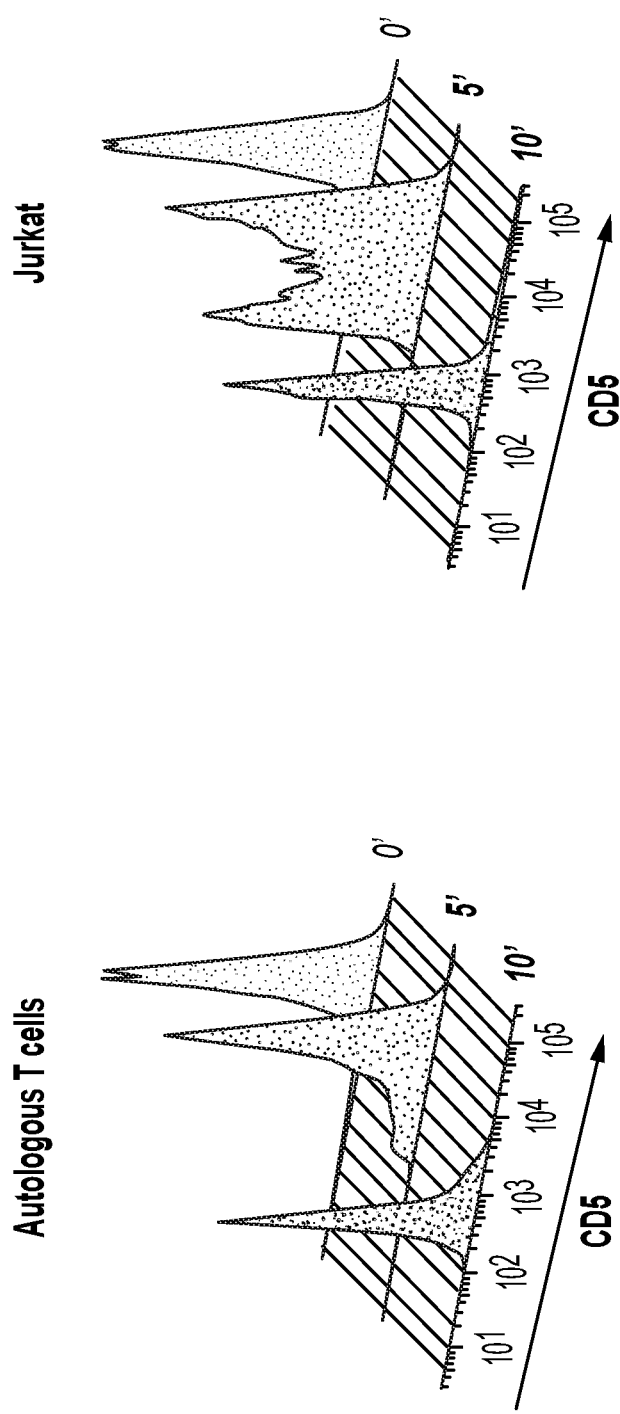
Figure 9D:
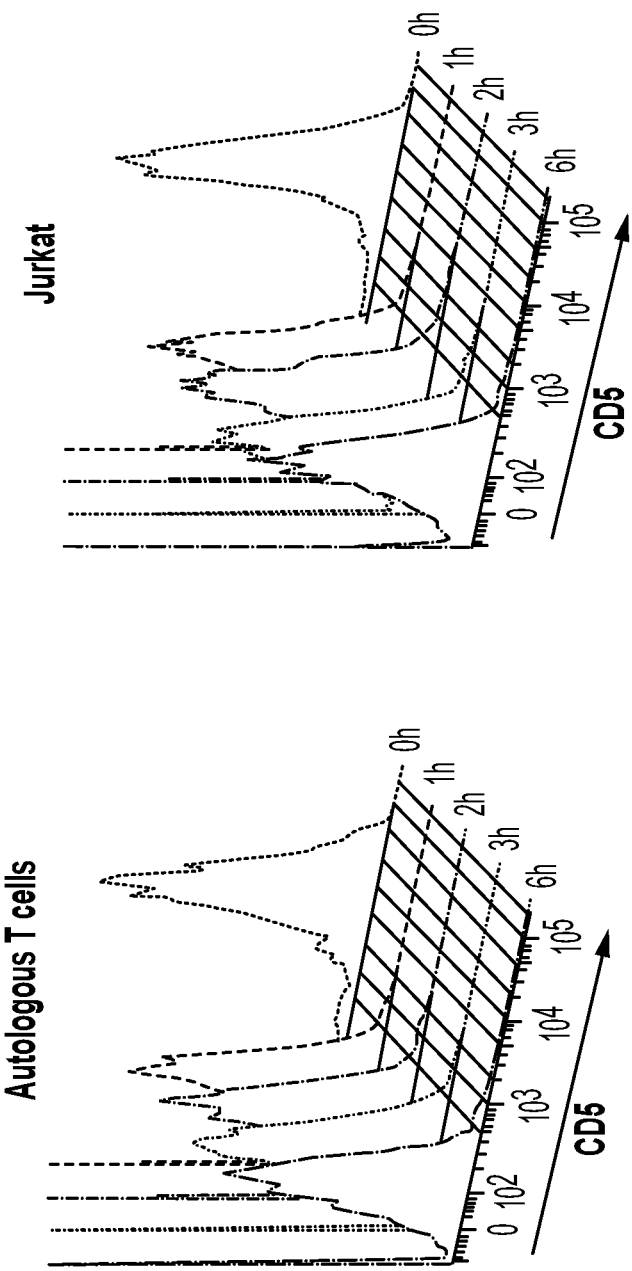

Enhanced cytotoxicity against leukemic cells might result from increased or more stable CD5 expression on the cell surface of malignant T cells. However, surface expression of CD5 was comparable in all leukemic cell lines and activated T cells (FIGS. 9A and 9B). Similar kinetics of CD5 downregulation was observed in normal and malignant T cells after mixing them with CD5 CAR T cells (FIGS. 9C and 9D). Initial binding of CAR molecules with CD5 triggered rapid internalization of unbound CD5 protein in both Jurkat and activated normal T cells, suggesting that the differential killing was unrelated to disparate persistence of CD5 antigen expression.

Figure 4A:
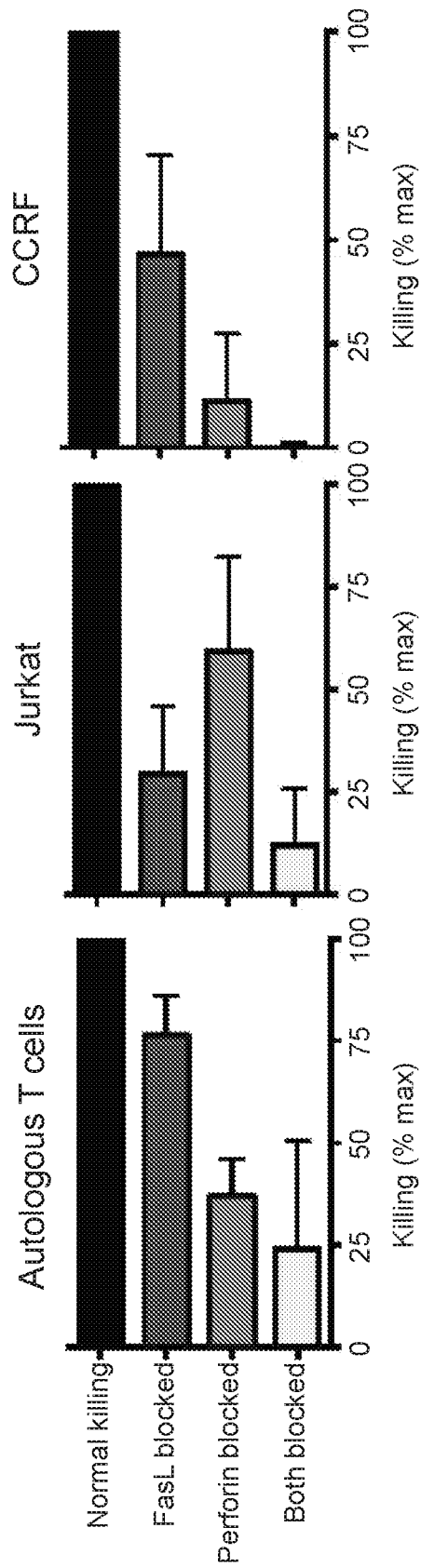
FIG. 4A-4F—Multiple mechanisms contribute to resistance to fratricide.

T-cell cytotoxicity is primarily mediated by two separate mechanisms: perforin/granzyme secretion and Fas/FasL-mediated apoptosis. It was determined which pathways contribute to the cytotoxicity of CD5 CAR T cells against normal and malignant target cells. CD5 CAR T cells were co-cultured with autologous T cells or Jurkat cells in the presence of brefeldin A (BFA) and anti-FasL antibodies (cooperatively blocking the FasL pathway), or concanamycin A (CMA) and EGTA (inhibiting the perforin pathway), or all four agents. Apoptosis of target cells was measured by Annexin V staining to determine residual cytotoxic effector activity. Blocking the FasL pathway did not significantly change the extent of cytotoxicity against autologous T cells, but perforin inhibition with CMA/EGTA reduced fratricide by 63%, (FIG. 4A, left) suggesting the predominance of this pathway in fratricidal killing. In contrast, cytotoxicity against Jurkat and CCRF cells was substantially decreased upon blocking FasL (FIG. 4A, central and right), highlighting the importance of this mechanism in killing malignant T cells in addition to the perforin-dependent pathway. Therefore, CD5 CAR T cells utilize both perforin- and Fas-mediated pathways to eliminate Jurkat and CCRF cells, while fratricide is predominantly mediated by a perforin-dependent mechanism.

Figure 4B:
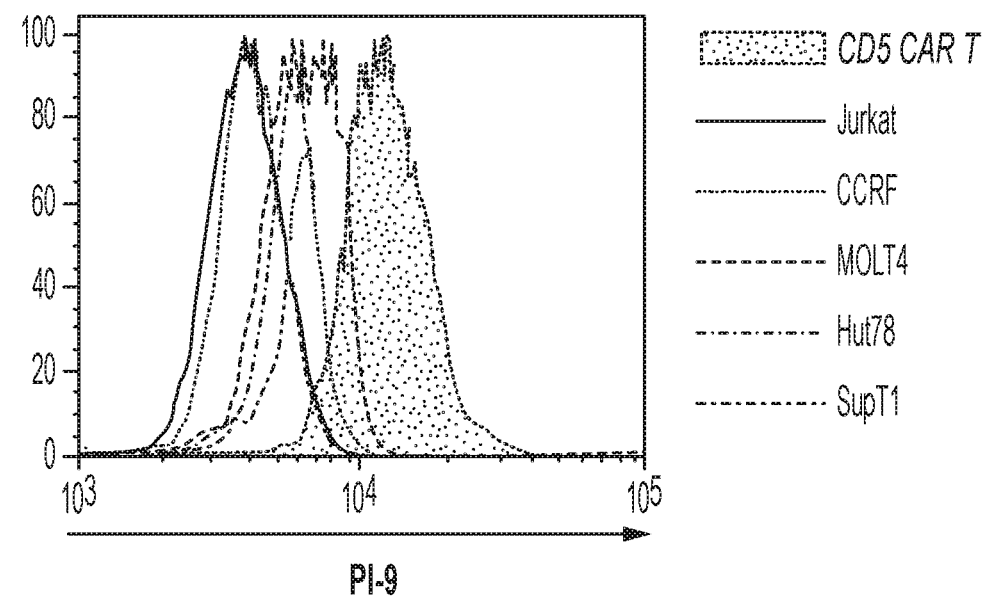
Figure 4B:
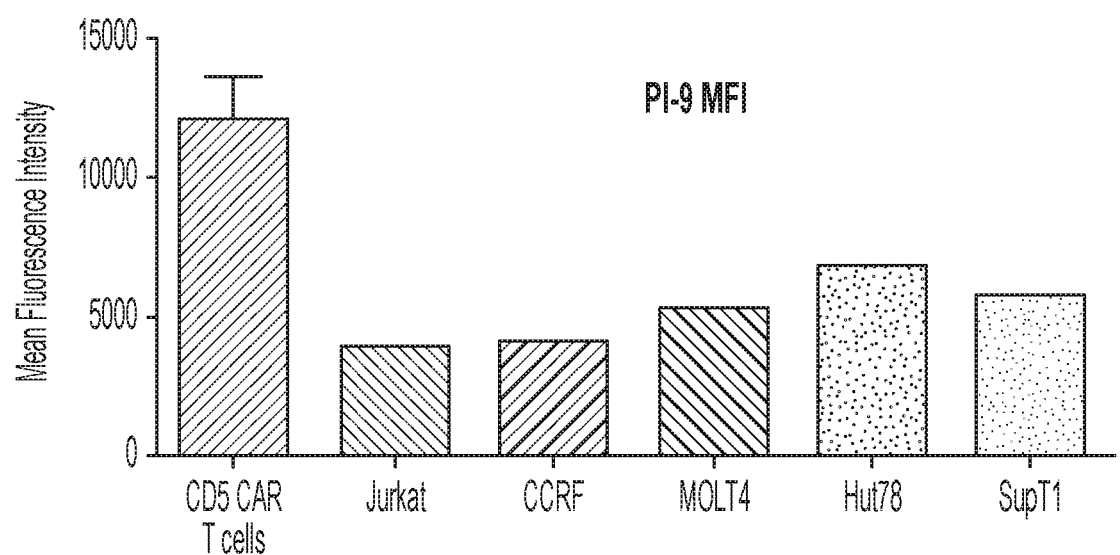
Figure 4C:
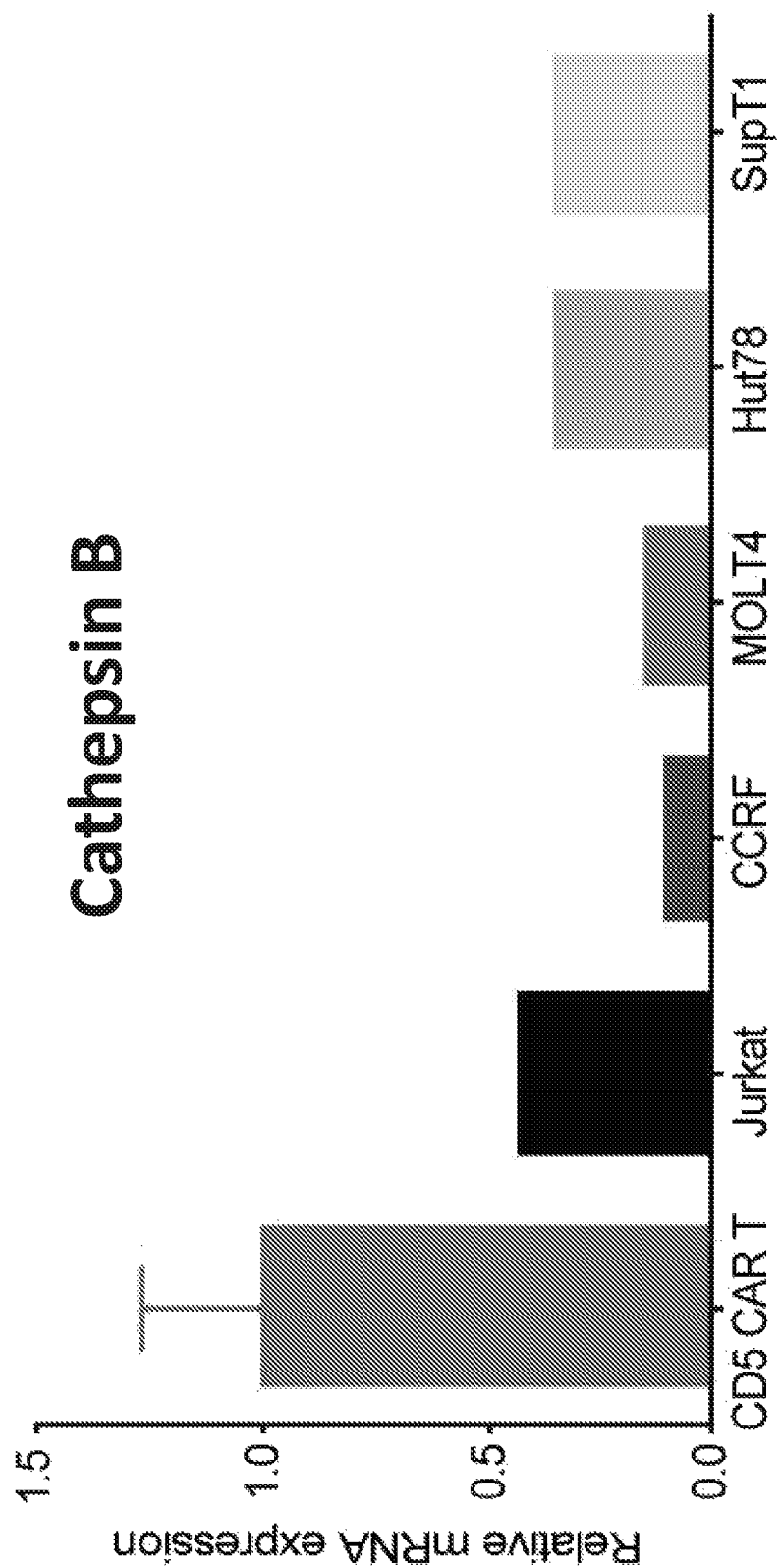

Effector T cells employ several mechanisms to protect themselves against autolysis by perforin and granzymes, including overexpression of the serine protease inhibitor PI-9, a specific inhibitor of granzyme B (Sun, et al., 1996), and cathepsin B that provides resistance to perforin (Balaji, et al., 2002). Both PI-9 (FIG. 4B) and cathepsin B (FIG. 4C) were upregulated in CD5 CAR T cells compared to T-ALL cell lines, providing a means by which CD5 CAR T cells can resist perforin/granzyme-mediated fratricide.

Figure 4D:
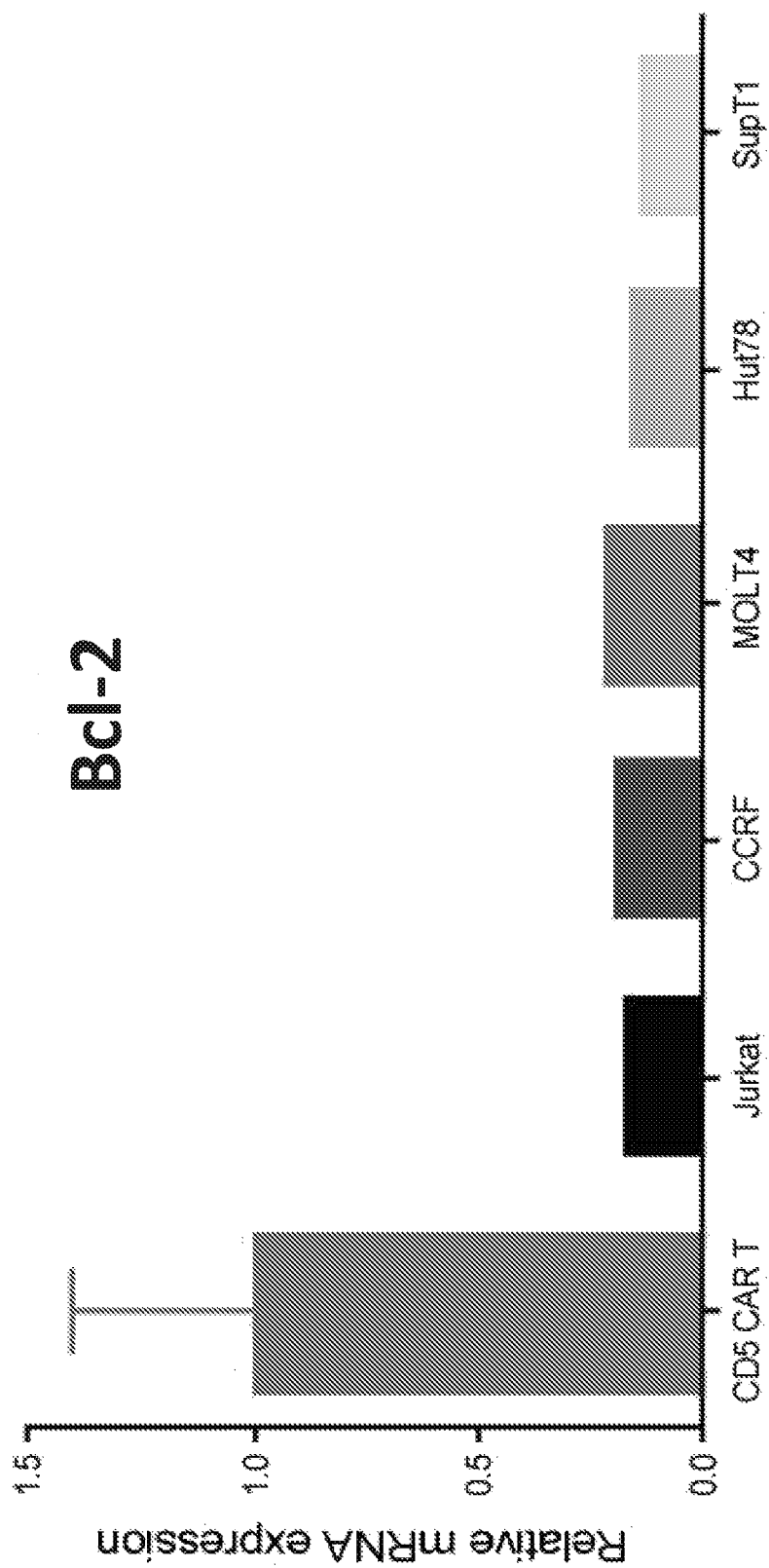
Figure 4E:
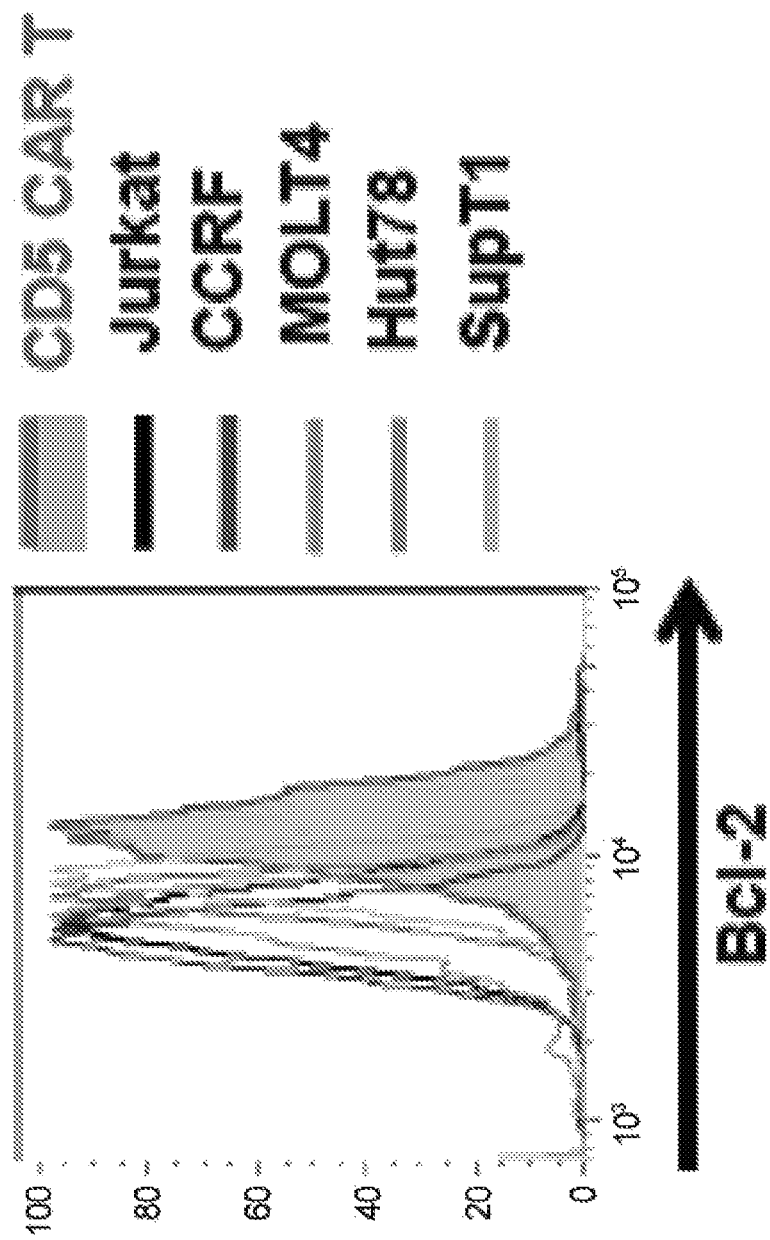
Figure 4F:
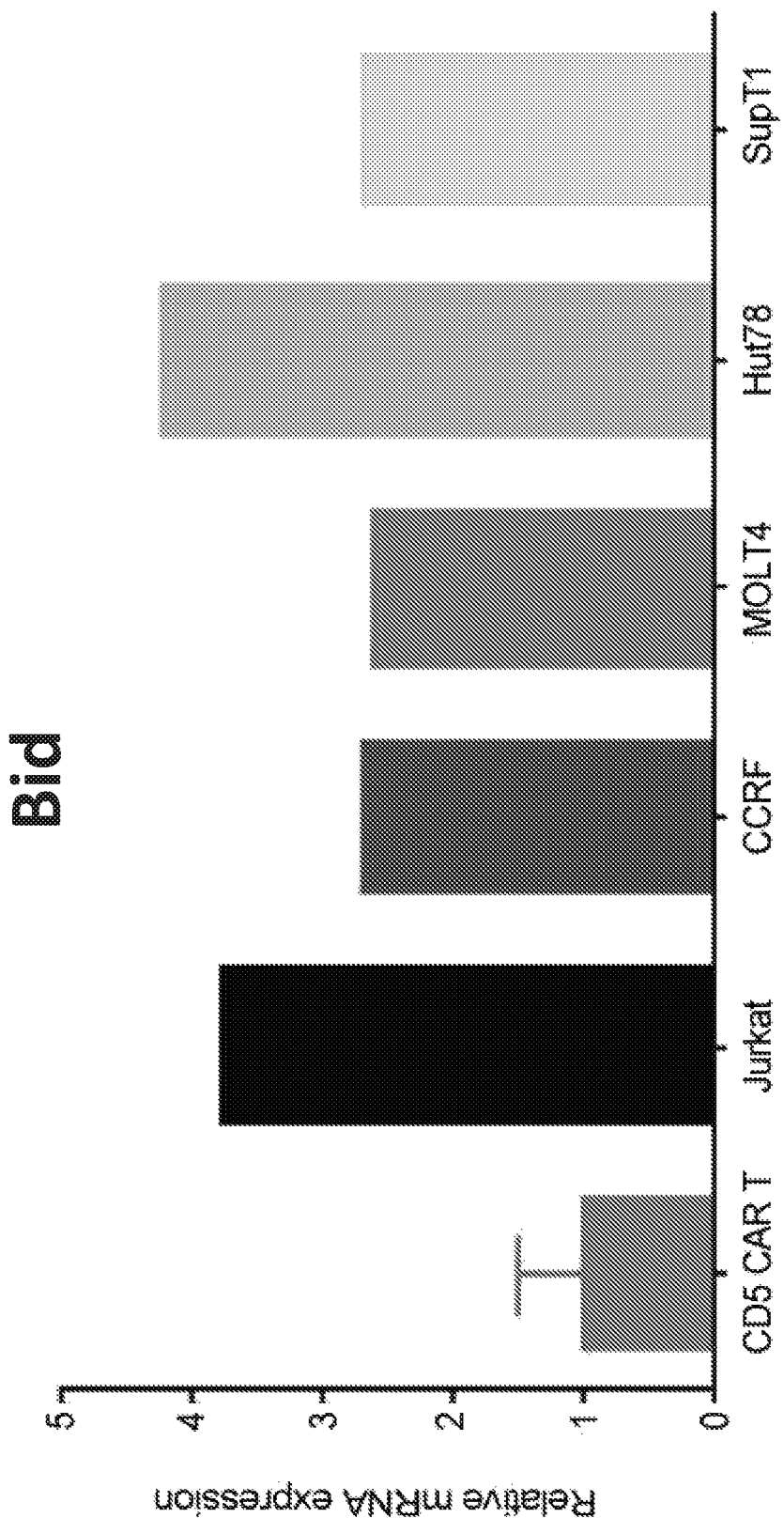
Figure 10:
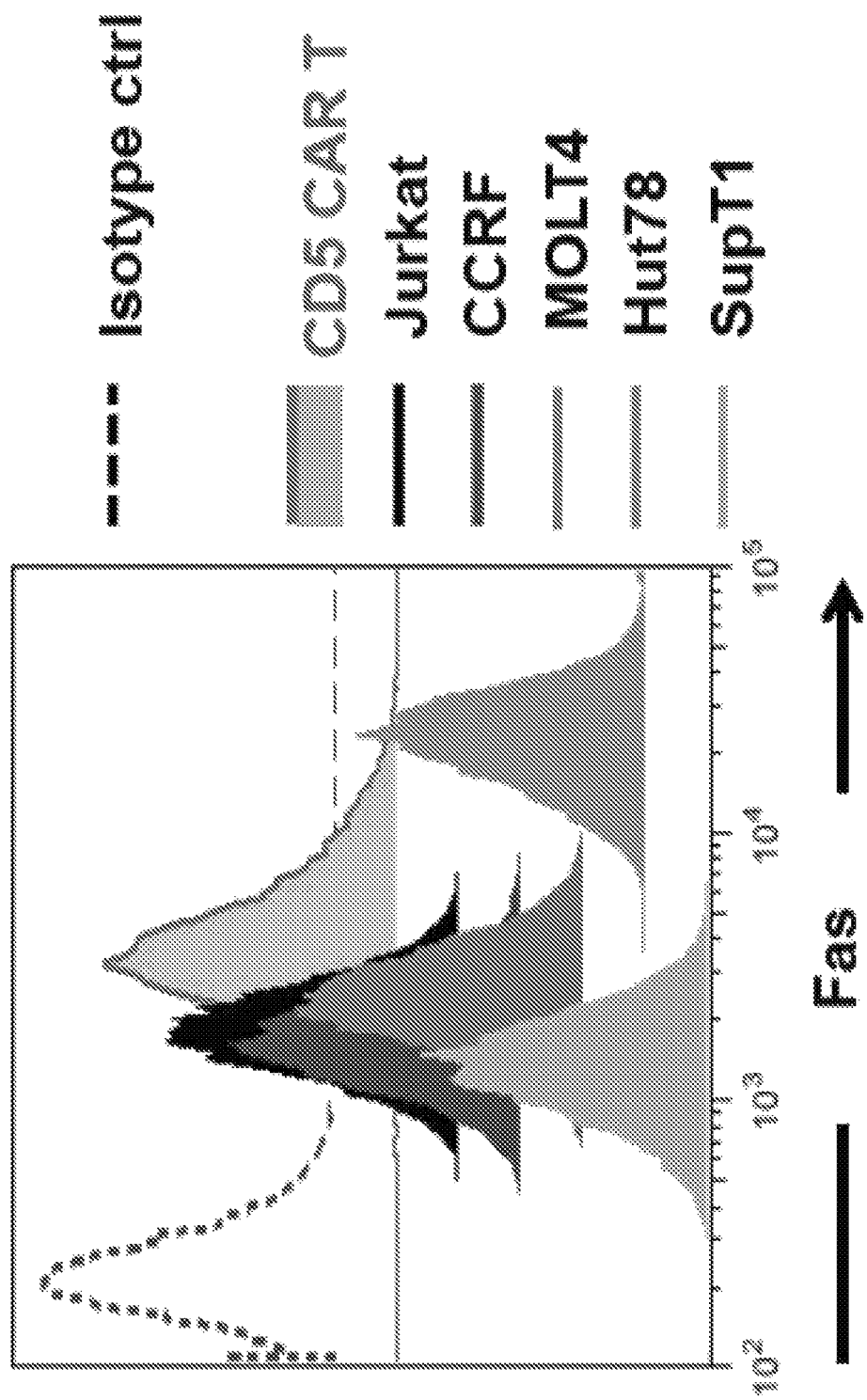
FIG. 10—Fas expression in CD5 CAR T cells and malignant T cell lines. CD5 CAR T cells (7 d post-transduction) and malignant T cell lines were stained with anti-Fas antibody and analyzed by flow cytometry.

Fas-mediated apoptosis is triggered by caspase 8-mediated cleavage of the pro-apoptotic protein bid and is inhibited by bcl-2 (Luo, et al., 1998). While both normal and malignant T cell lines expressed Fas on the cell surface (FIG. 10), levels of bcl-2 were significantly higher in CD5 CAR T cells (FIGS. 4D and 4E). Conversely, malignant T cells expressed more bid (FIG. 4F), which correlates with the enhanced sensitivity of T-ALL and T lymphoma cell lines to Fas-mediated cell death.

CD5 CAR T Cells Recognize and Kill Primary T-ALL Cells.

Figures 1, 5A:
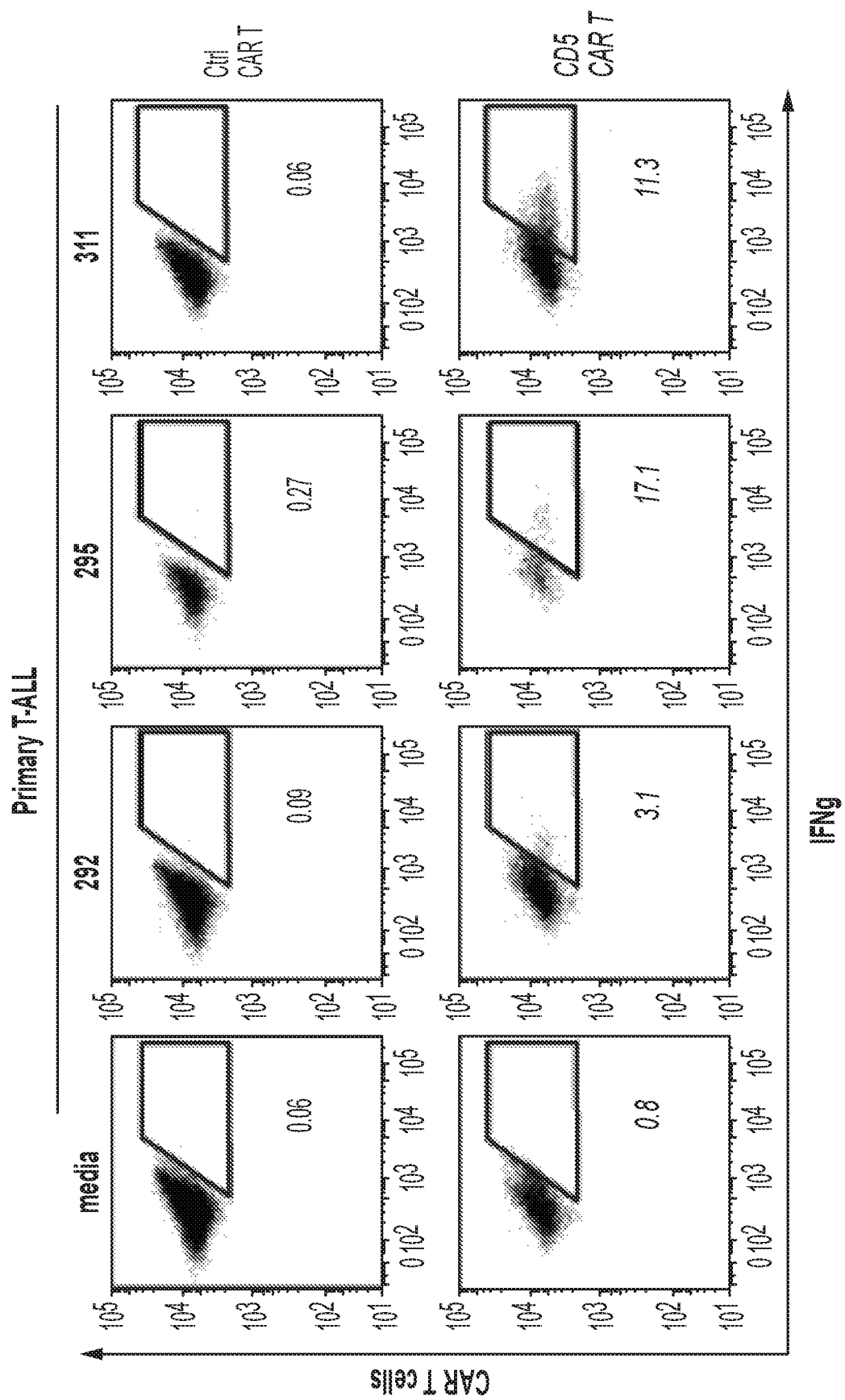
FIG. 5A-5E—CD5 CAR T cells recognize and kill primary T-ALL cells.
Figures 2, 5A:
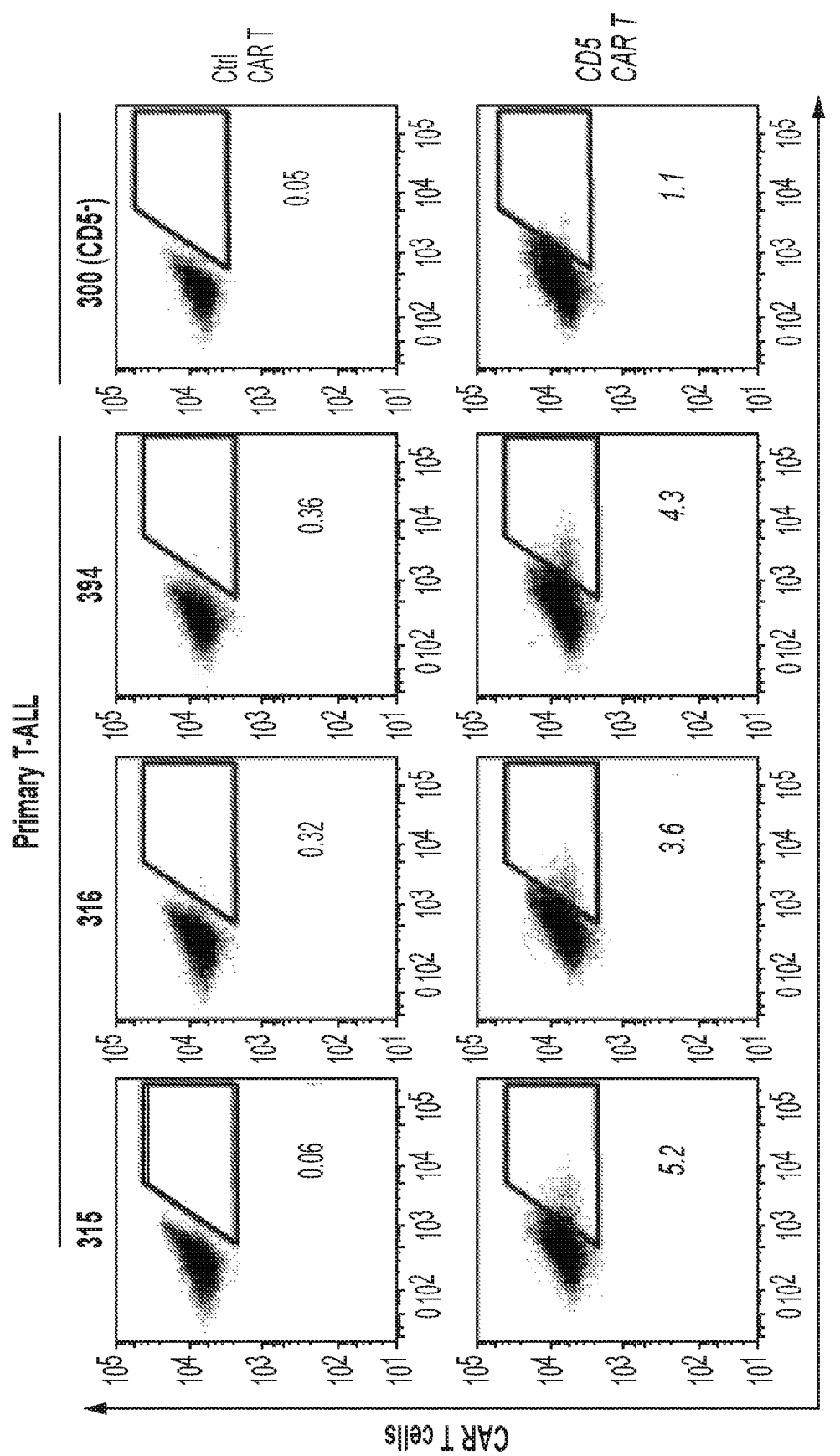
Figure 5B:
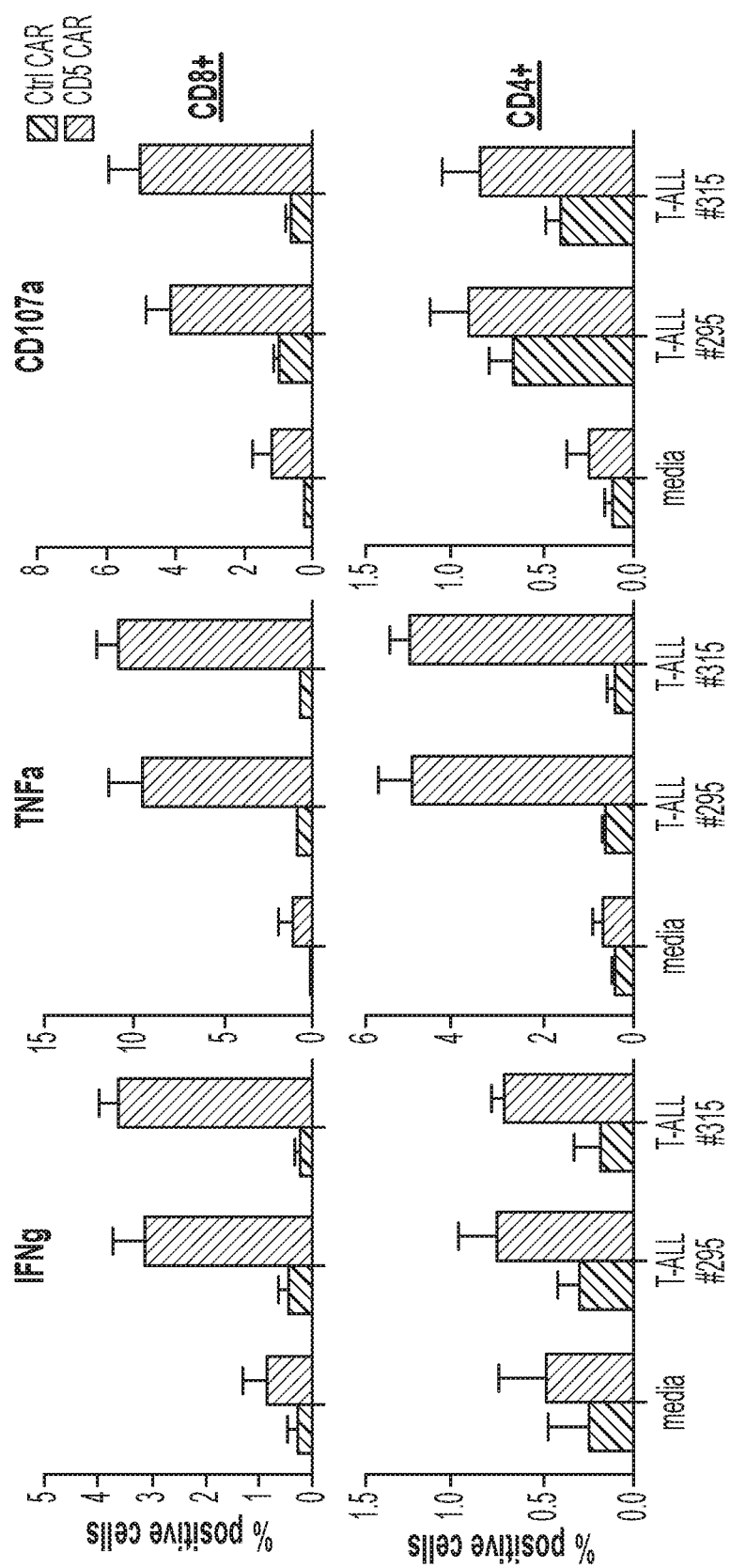
Figure 11:
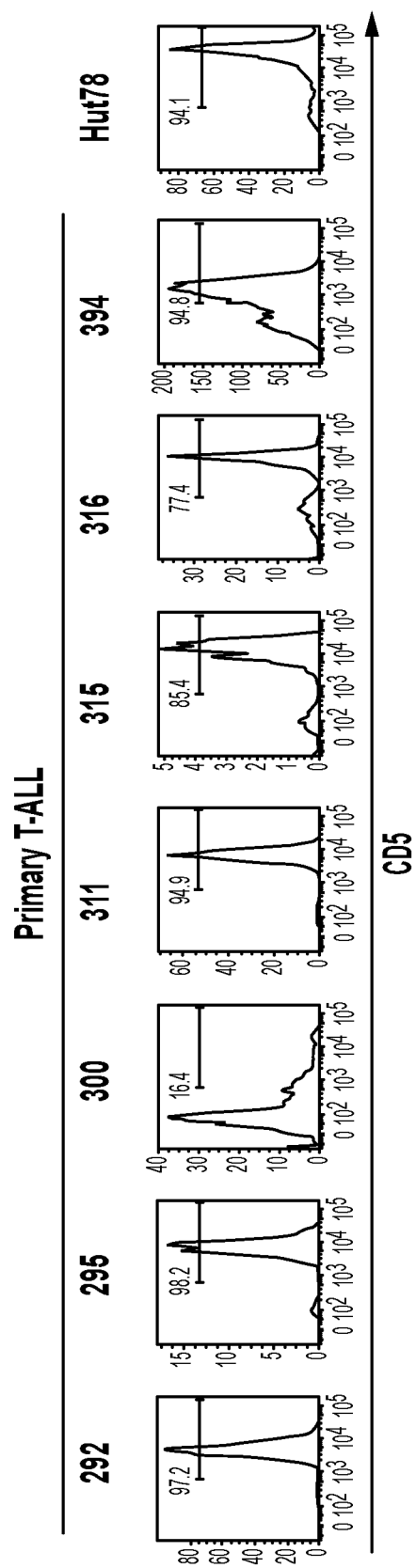
FIG. 11—Surface expression of CD5 in primary T-ALL blasts. Peripheral blood samples from T-ALL patients were stained with anti-CD5 antibody for 30' on ice and analyzed by flow cytometry. CD5 expression in Hut78 cell line is shown as a positive control.
Figures 1, 12A:
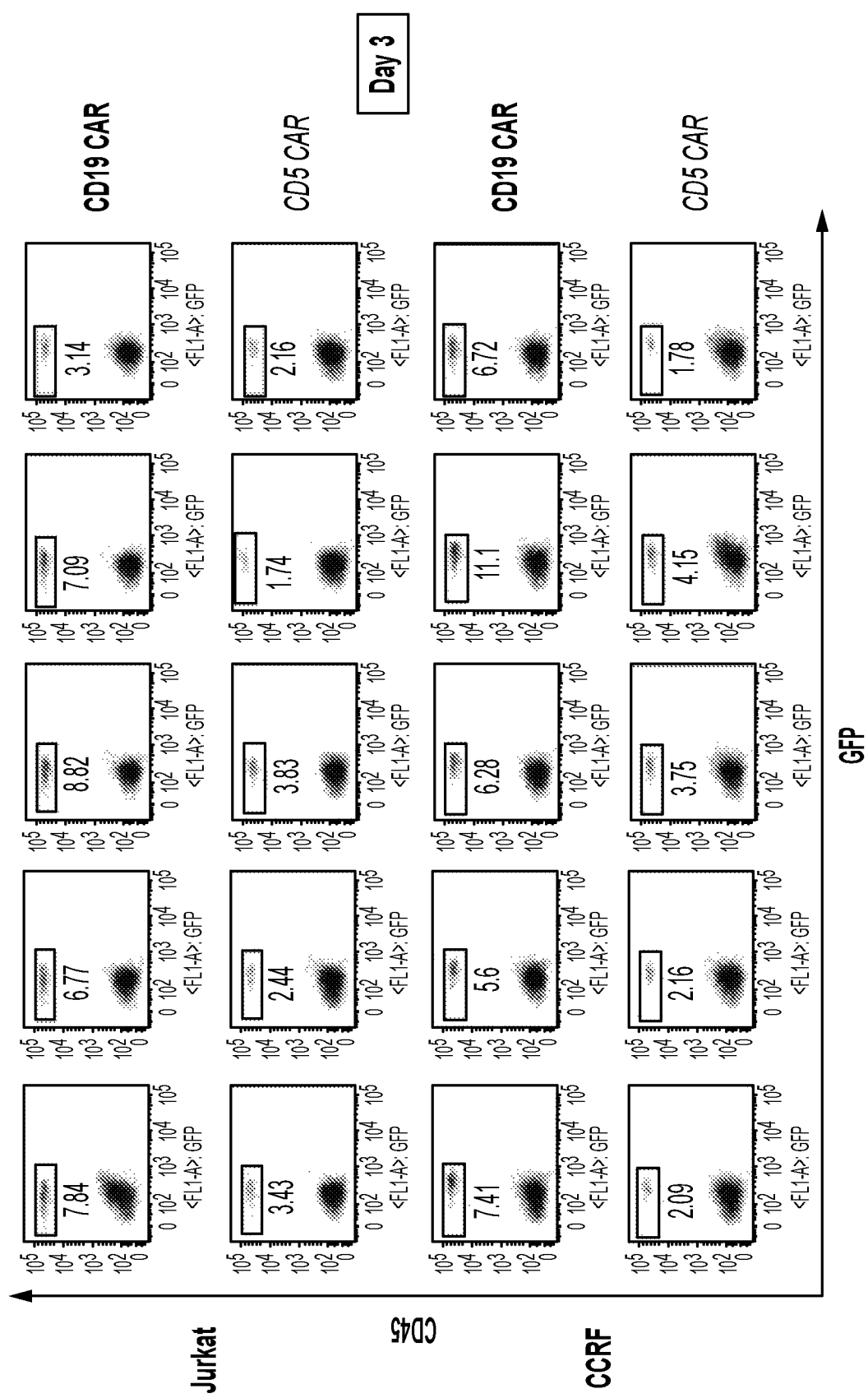
FIGS. 12A-12D—Frequency of CAR T cells in peripheral blood of mice after adoptive transfer.
Figures 2, 12A:
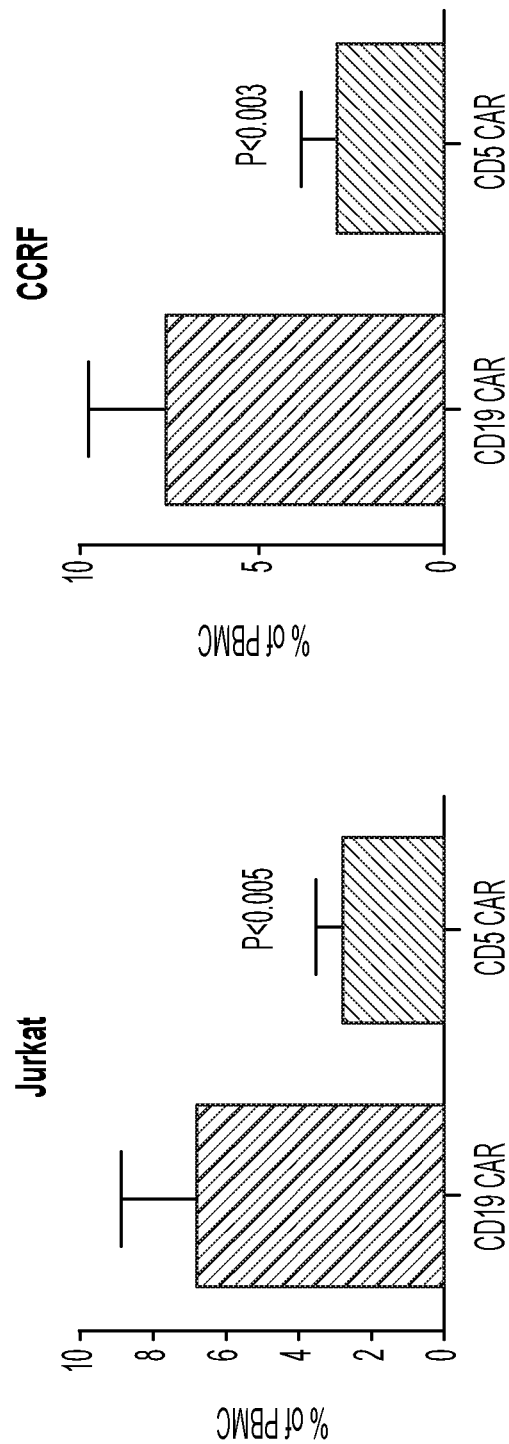
Figure 12B:
Figure 12C:
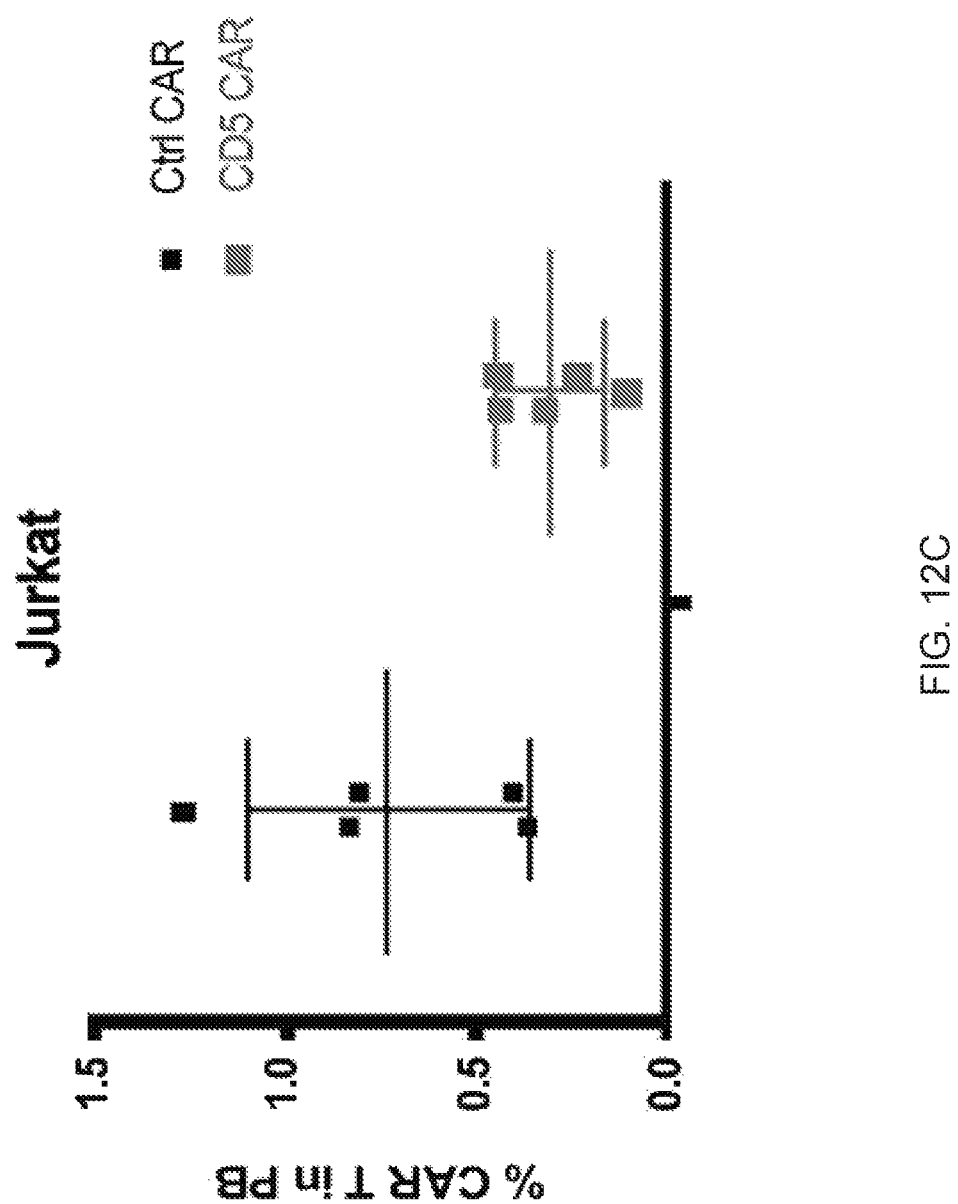
Figure 12D:
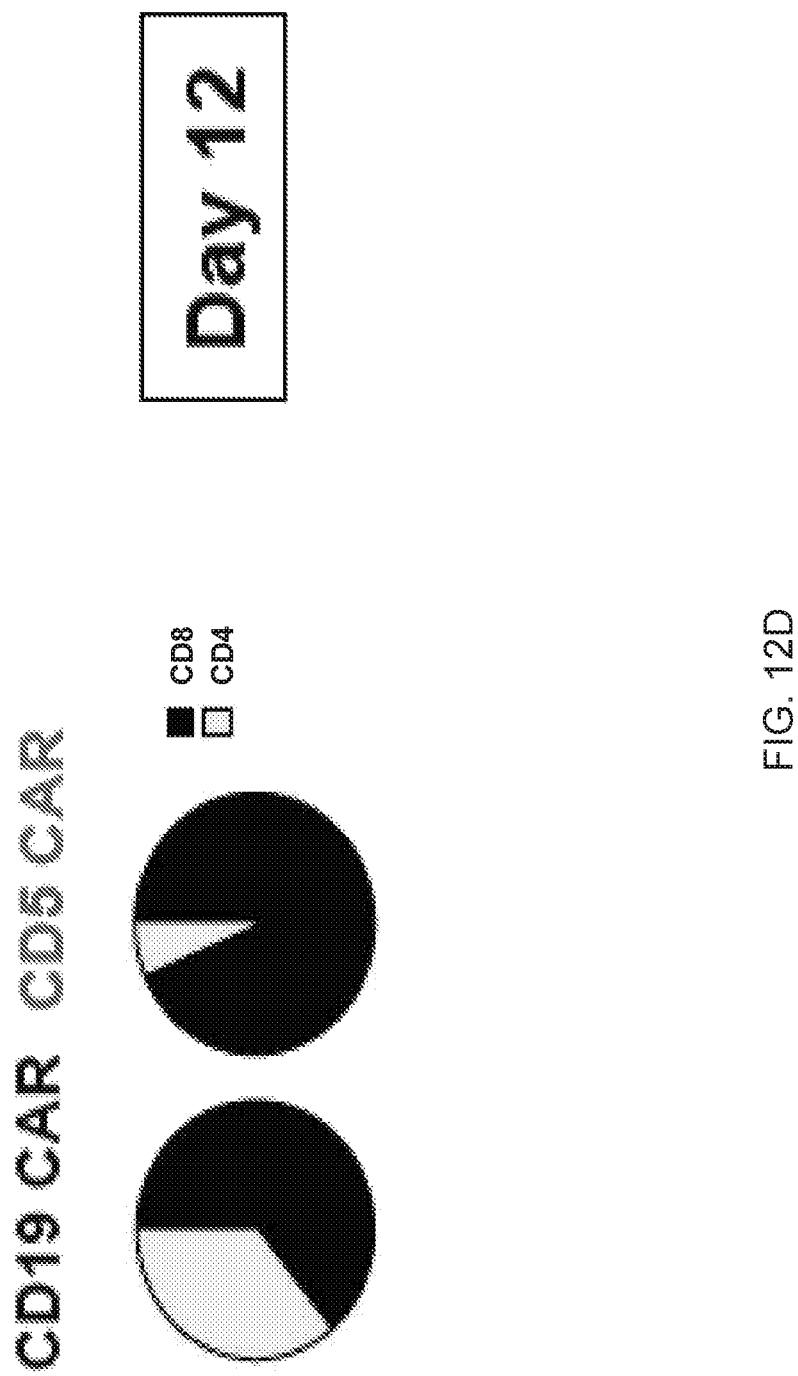

The ability of CD5 CAR T cells to respond to and kill primary tumor cells from T-ALL patients was evaluated. There was discernible cytokine production and degranulation by CD5 CAR T cells in response to primary T-ALL blasts from several patients (FIGS. 5A and 5B). Most of these T-ALL samples were CD5-positive except T-ALL #300 (FIG. 11), which elicited minimal production of IFNγ (FIG. 5B).

Figure 5C:
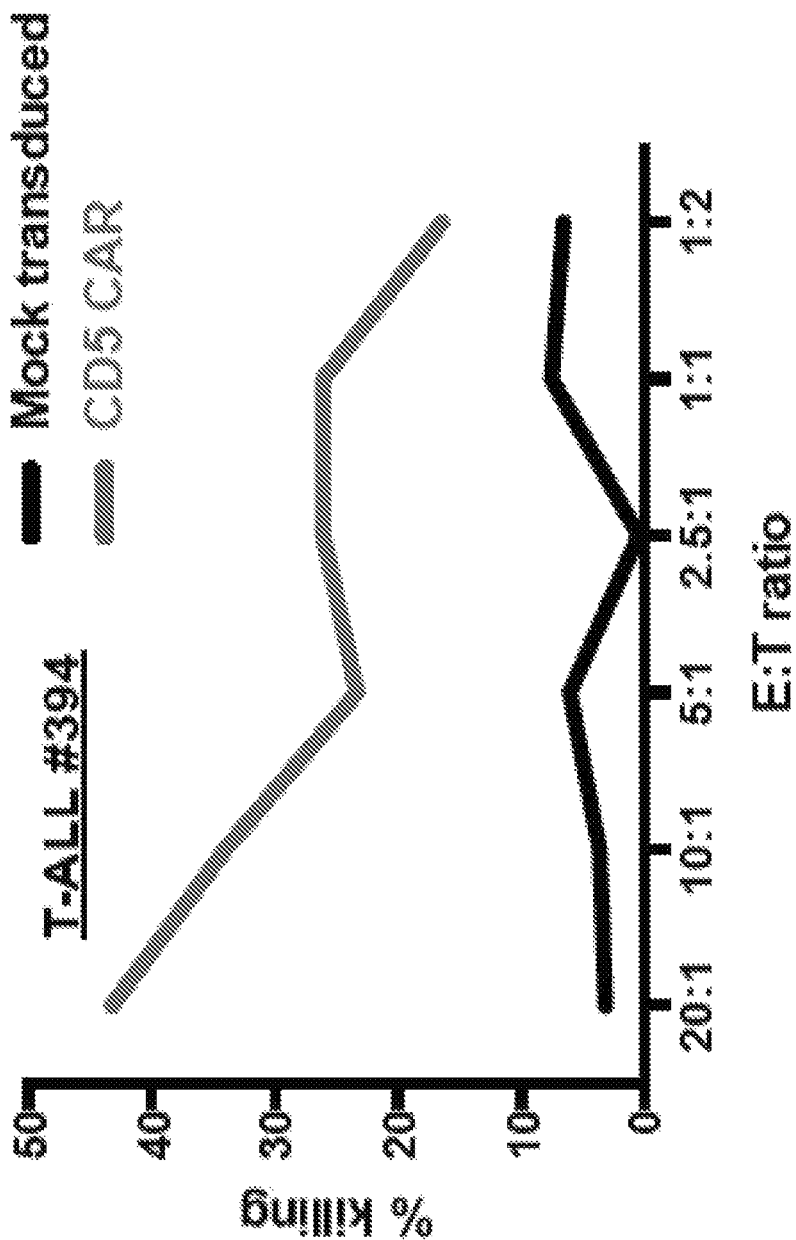
Figure 5D:
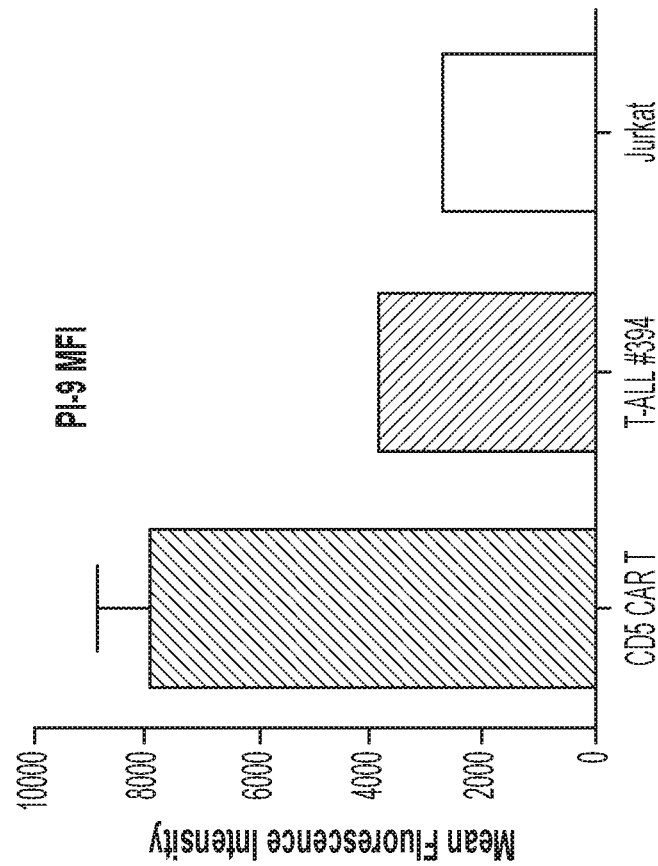
Figure 5D:
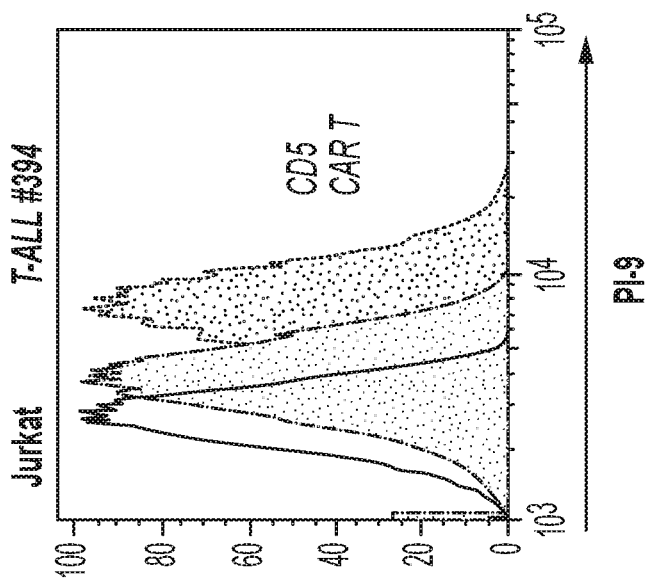
Figure 5E:
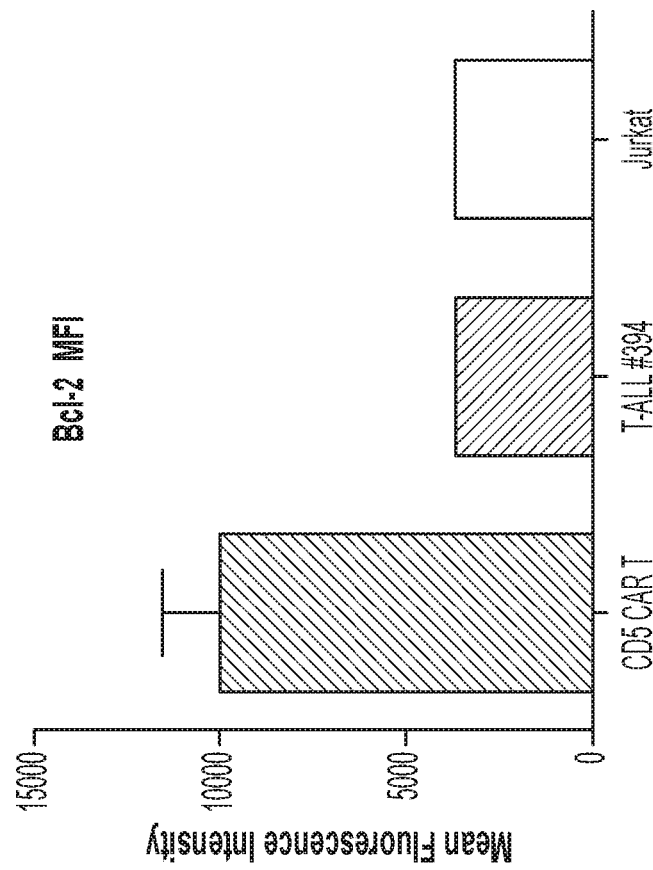
Figure 5E:
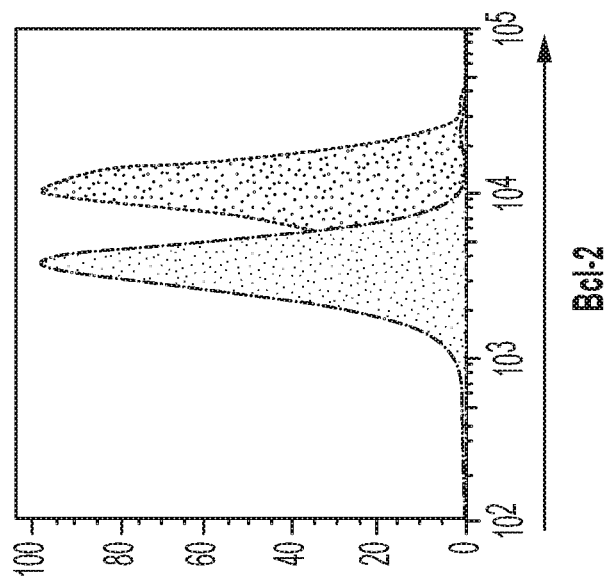

To assess cytotoxicity of CD5 CAR T cells against primary tumor cells, peripheral blood mononuclear cells of a T-ALL patient were purified and used as targets in a 5 hr Cr release assay with normal donor T cells transduced with either CD5 CAR or a mock retrovirus. There was substantial cytotoxicity with CD5 CAR T cells and minimal alloreactive killing from mock-transduced T cells (FIG. 5C). These data further strengthen the consideration that CD5 CAR T cells have a significant therapeutic potential to eradicate primary T-cell malignancies.

Efficient Control of T-ALL Progression by CD5 CAR T Cells In Vivo.

Figure 6A:
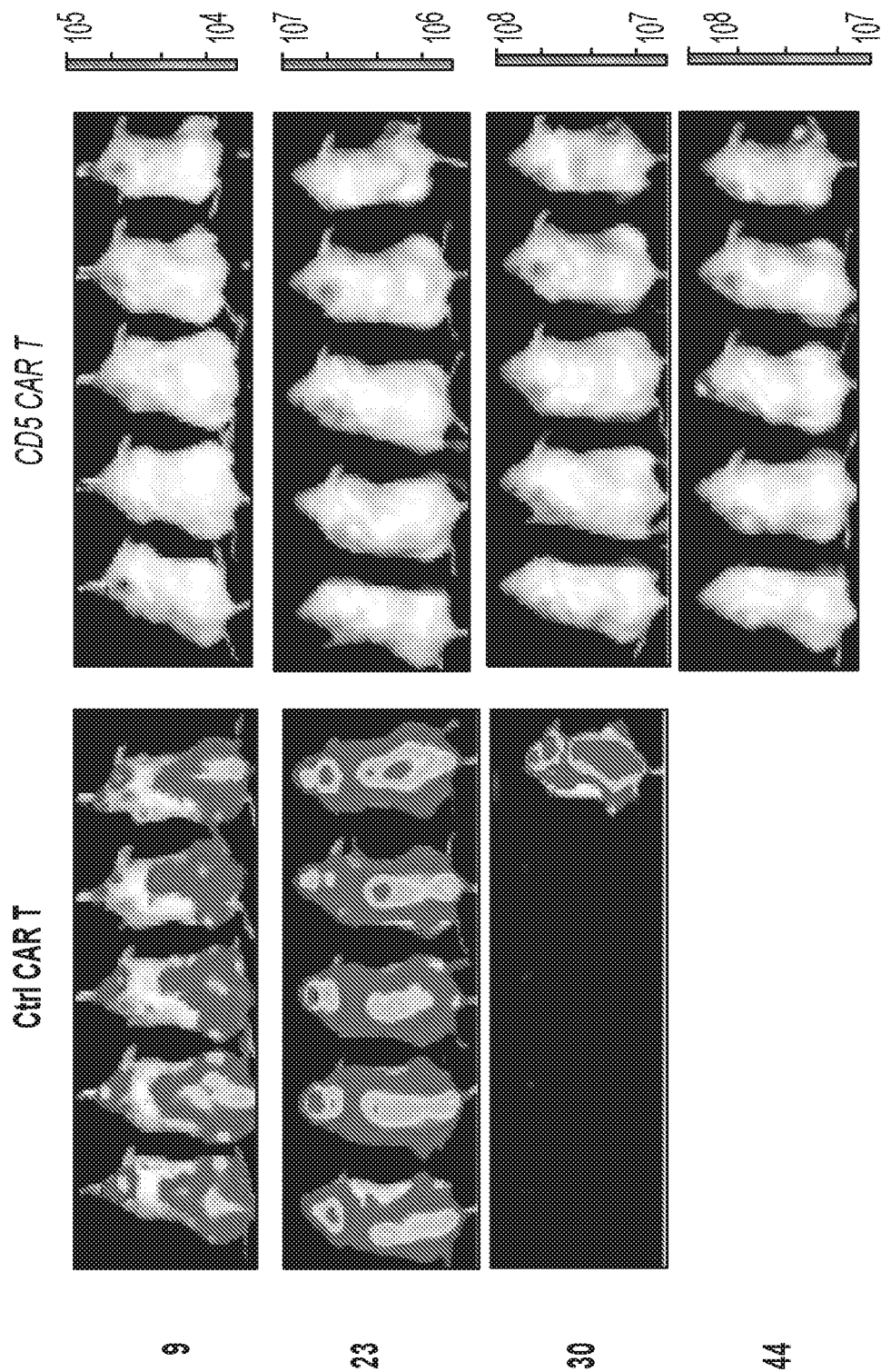
FIG. 6A-6G—CD5 CAR T cells control progression of T-ALL in xenograft mouse models.
Figure 6B:
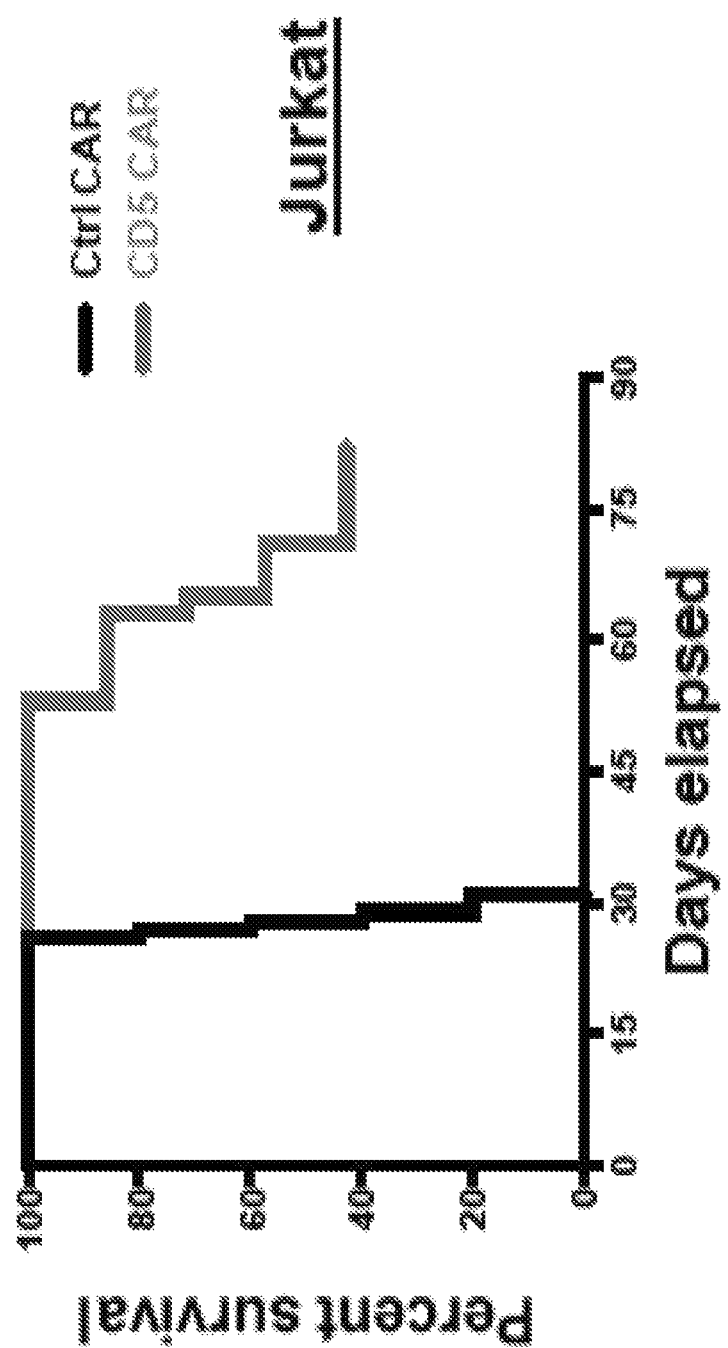

The ability of CAR T cells to suppress or eliminate malignant cells in vivo in xenograft mouse models may be an important predictor of their therapeutic efficacy in patients. A xenograft mouse model of disseminated T-ALL was established by intravenously engrafting NOD.SCID γ-chain deficient mice with firefly luciferase-expressing Jurkat cells and the capacity of CD5 CAR T cells (injected on day 3 and day 6 after tumor implantation) to control disease progression was evaluated by recording in vivo luminescence. Upon intravenous injection, Jurkat cells establish disseminated leukemia expanding preferentially in the spine, femur, head and pelvis (Christoph, et al., 2013), with limited numbers of cells in peripheral blood. Mice receiving control CD19 CAR T cells developed rapid disease progression and were euthanized by day 30 (FIGS. 6A and 6B). In contrast, mice receiving CD5 CAR T cells were significantly protected from rapid progression and their median survival was prolonged by >150% (28.0 days in control CAR group vs. 71.0 days in CD5 CAR group, P=0.0003) (FIGS. 6A and 6B).

Figure 6C:
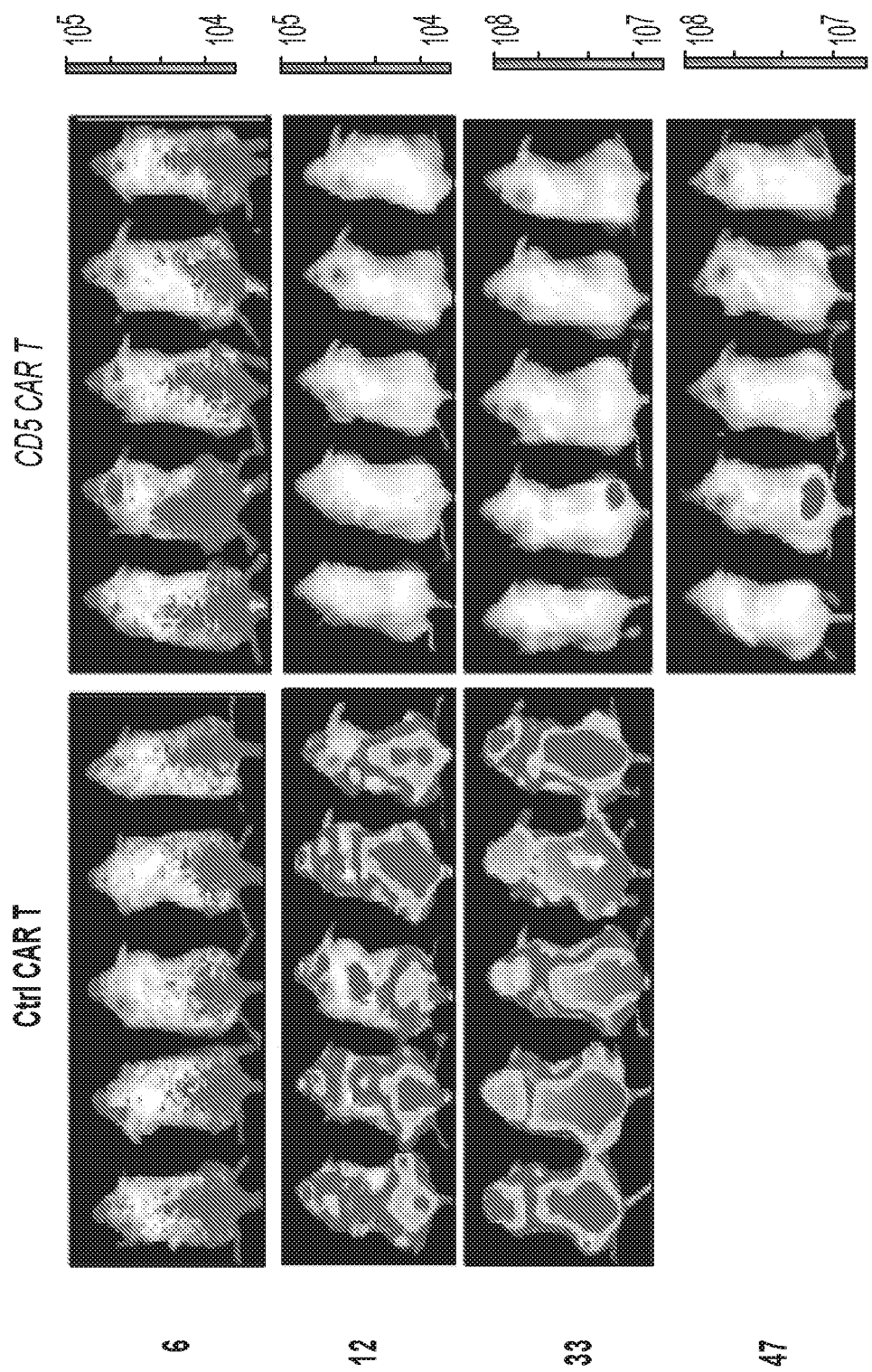
Figure 6D:
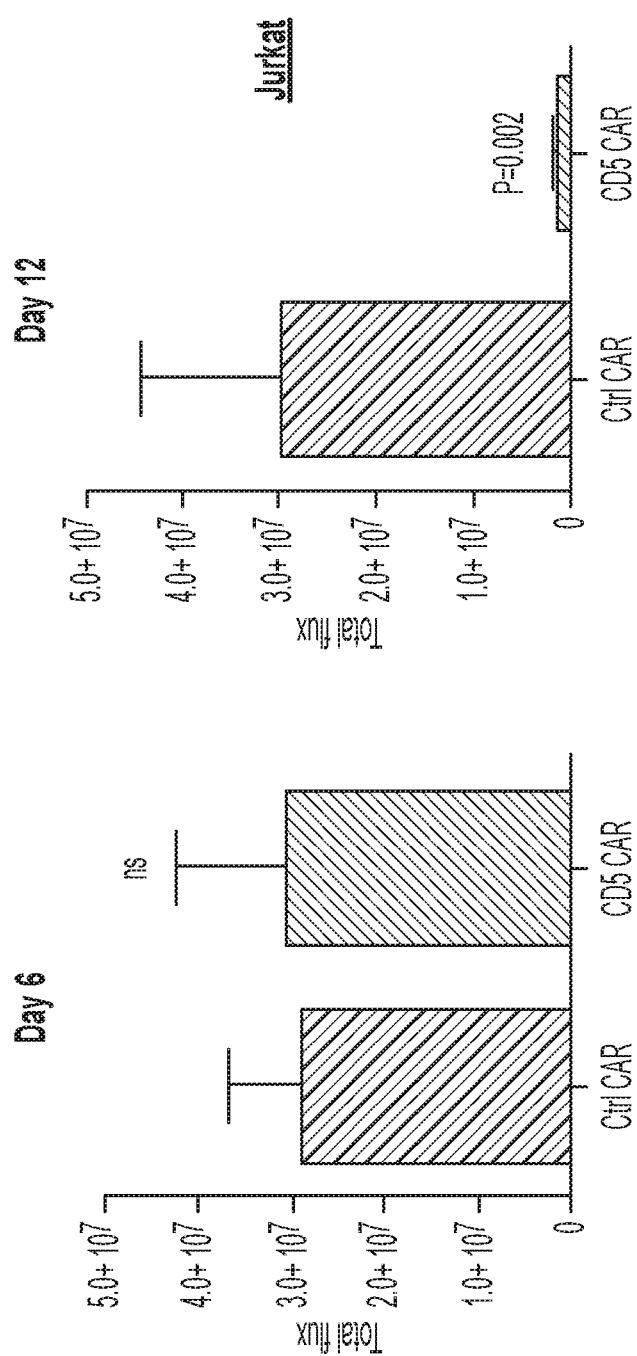

The capacity of CD5 CAR T cells to control established tumor was evaluated by injecting CAR T cells on day 6 and 9 post implantation. By day 6, the overall tumor burden in control and CD5 CAR groups was similar. In the group receiving CD5 CAR T cell injection, however, the disease was significantly reduced by day 12 (FIGS. 6C and 6D). No benefit was seen from CD19 CAR T cells despite their higher frequency in peripheral blood after infusion (FIG. 12).

Figure 6E:
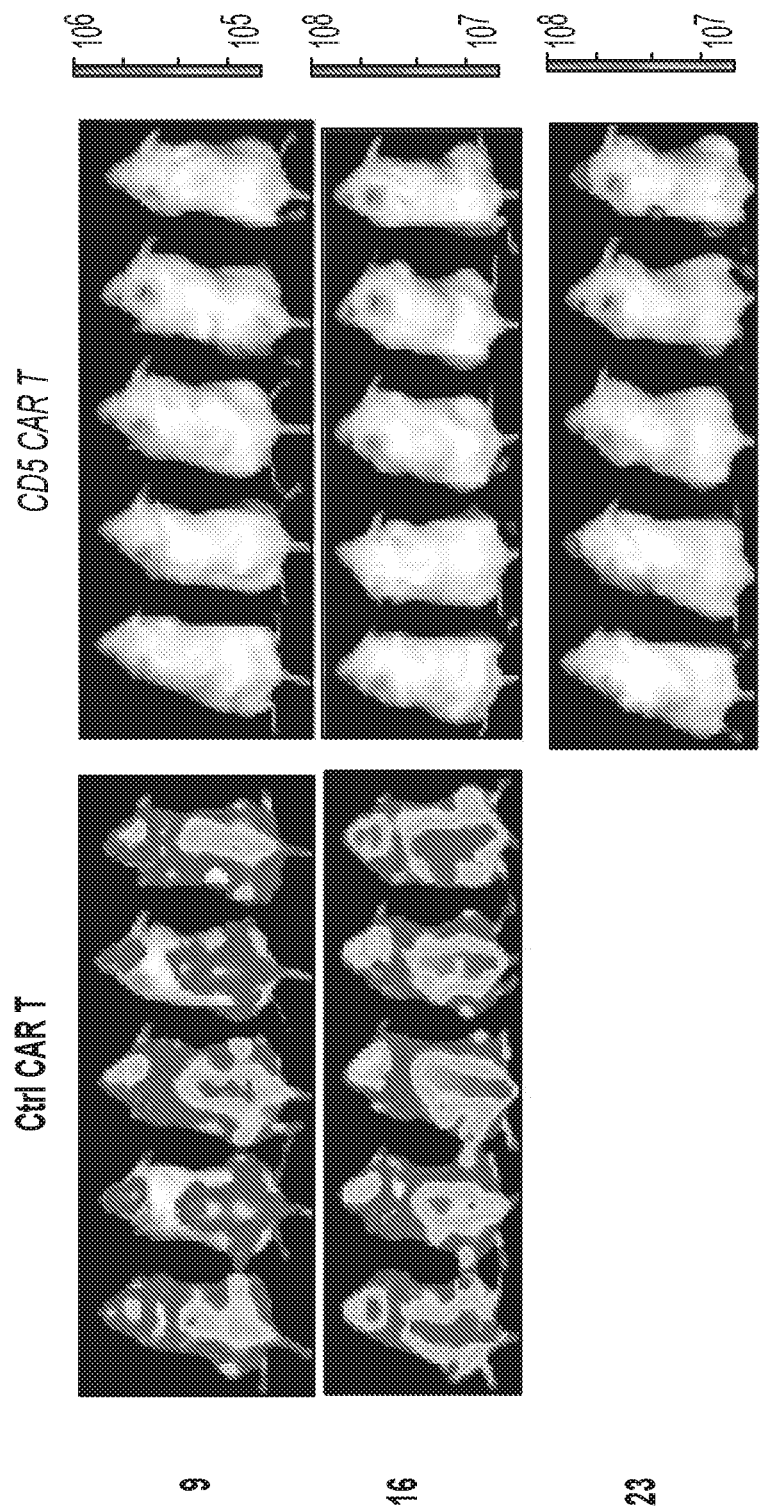
Figure 6F:
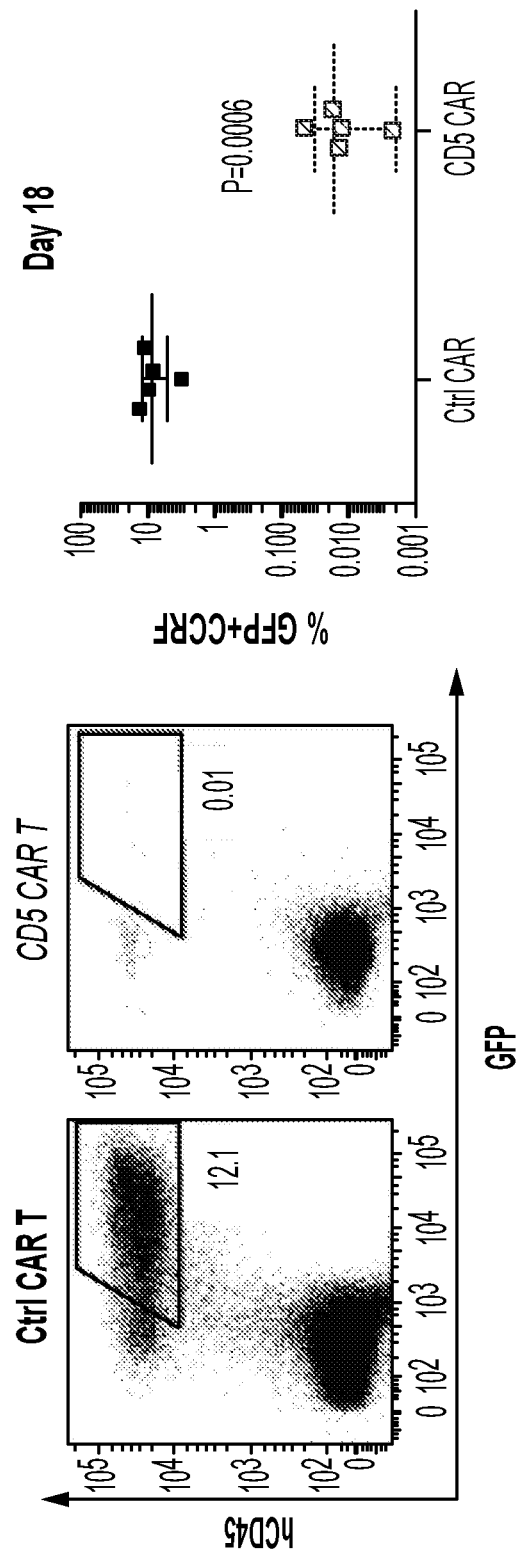
Figure 6G:
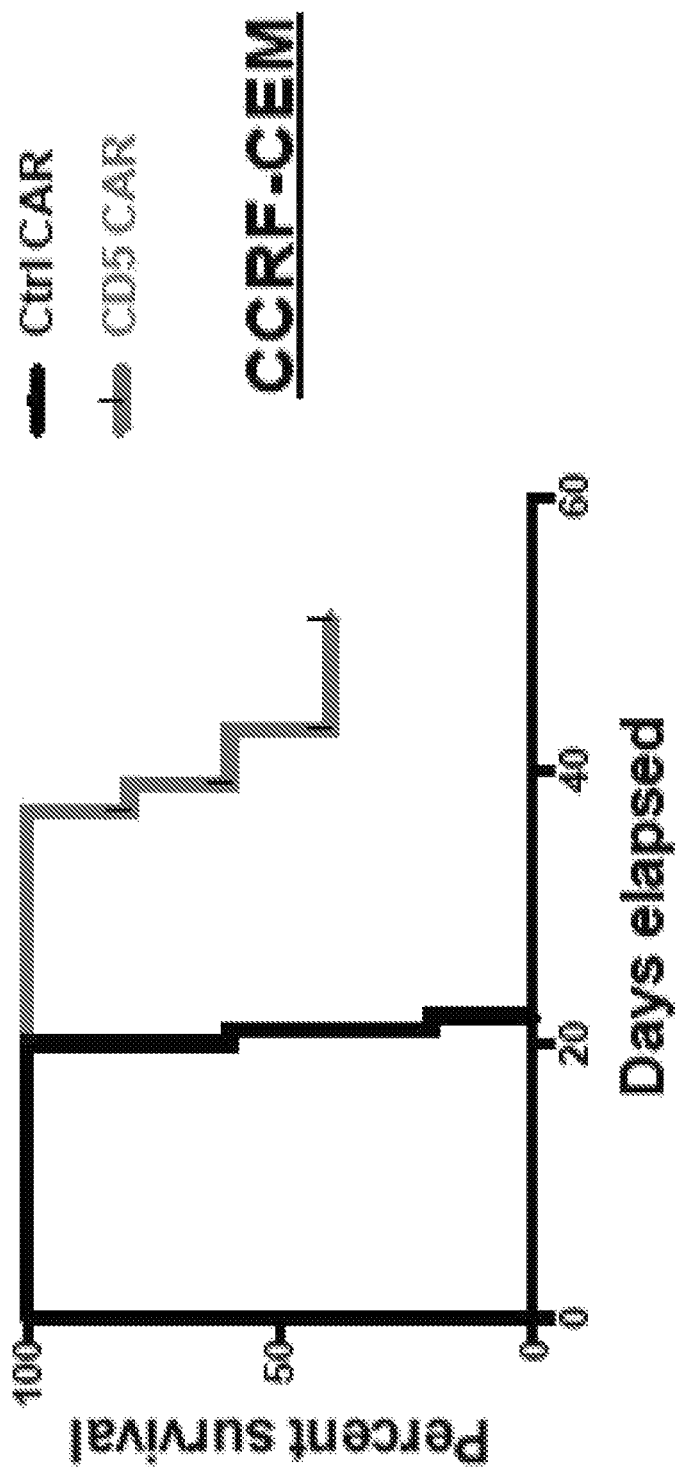
Figure 13:
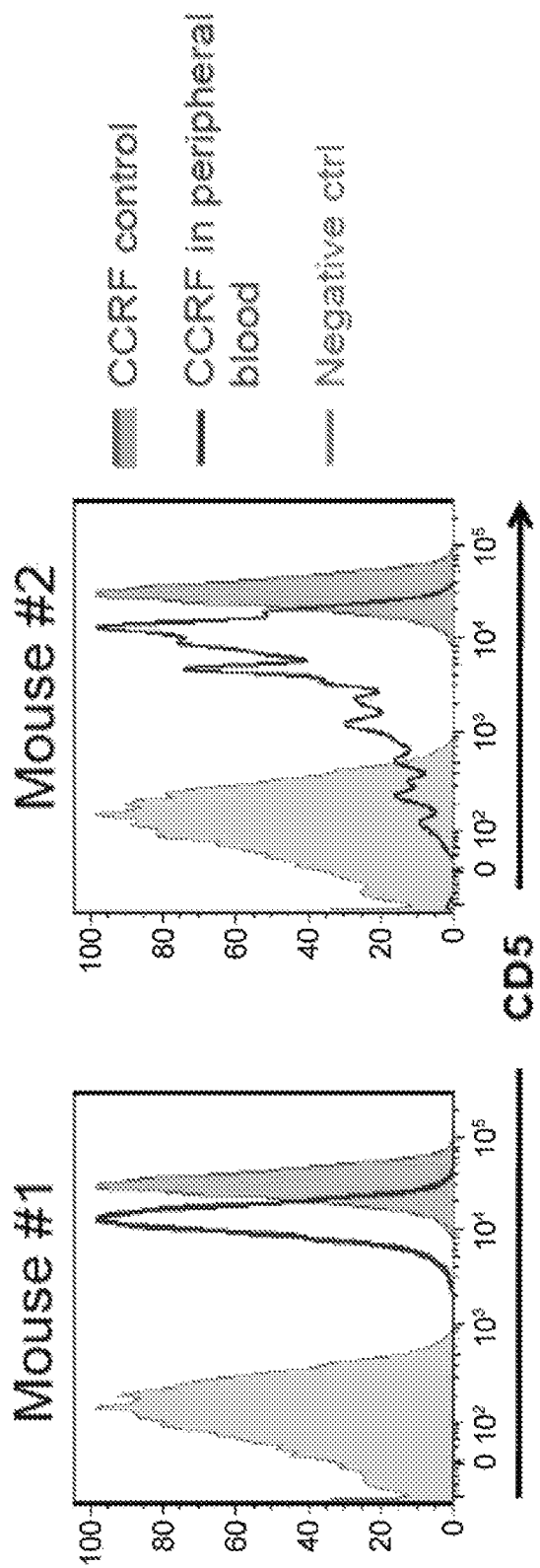
FIG. 13—Status of CD5 expression in surviving tumor cells in vivo after CD5 CAR T treatment. Peripheral blood of mice previously engrafted with GFP+CCRF-CEM and treated with CD5 CAR T cells was collected by tail vein bleeding. CD5 expression was analyzed by flow cytometry in hCD45+ GFP+ cells. CCRF control represents CD5 expression in CCRF cells in culture.

A second xenograft mouse model was established of an aggressive T-ALL by engrafting CCRF-CEM cells intravenously to produce a predominantly leukemic distribution of tumor with cells also detected in lymphoid organs. The ability of CD5 CAR T cells administered on day 3 and day 6 post-engraftment to suppress leukemia progression was tested. While the control mice succumbed to the disease by day 22, injection of CD5 CAR T cells significantly reduced tumor burden and disease progression (FIG. 6E). This benefit correlated with decreased frequency of CCRF cells in peripheral blood of mice 18 days post-engraftment (FIG. 6F) and extended median survival to 43.0 days vs. 21.0 in control mice (P<0.002) (FIG. 6G). Reemerging tumor cells in mice receiving CD5 CAR T cells still expressed CD5 (FIG. 13), suggesting that the lack of complete tumor eradication resulted from suboptimal performance of CAR T cells in mouse hosts rather than from antigen escape.

X. Materials and Methods

CD5 CAR Design. Anti-CD5 single chain variable fragment (scFv) was created using commercial gene synthesis and cloned into a backbone of a $2^{nd}$ generation CAR (anti-kappa chain) containing an IgG Fc spacer, transmembrane and cytoplasmic portions of CD28 and a TCR zeta chain (Vera, et al., 2006). VL and VH parts of the scFv were connected with a $(G_4S)_3$ linker. For the in vivo studies, the $C_H2$ portion of the IgG Fc spacer was removed. A truncated version of CD5 CAR (ΔCD5 CAR) was created by deleting cytoplasmic domains.

Retroviral Transduction and Expansion of T Cells.

Peripheral blood mononuclear cells were isolated from healthy volunteers with a Ficoll-Paque and stimulated with anti-CD3 (OKT3, Ortho Biotech) and anti-CD28 (BD Pharmingen) antibodies for 48 h in CTL media (45% RPMI-1640, 45% Click's media, 10% FBS, supplemented with L-glutamin, penicillin and streptomycin). After that, T cells were transferred to a retronectin-coated plate with pre-bound retrovirus and transduced twice on day 2 and day 3. T cells were then transferred to another plate and expanded in the presence of IL-7 (10 ng/ml) and IL-15 (5 ng/ml). CD19 CAR (Savoldo, et al., 2011) and ΔCD5 CAR were used as controls. Efficiency of transduction routinely exceeded 90%. For some experiments, activated T cells were transduced with a GFP+ retrovirus in parallel to obtain GFP+ autologous T cells.

In Vitro T Cell Assays.

Cell lines Jurkat (clone E6-1, ATCC #TIB-152), CCRF-CEM (ATCC #CCL-119), MOLT-4 (ATCC #CRL-1582), Hut 78 (ATCC #TIB-161), SupT1 (ATCC #CRL-1942), Raji (ATCC #CCL-86) and Daudi (ATCC #CCL-213) were purchased from ATCC and expanded according to ATCC recommendations. For some experiments, Jurkat, CCRF-CEM and MOLT-4 cells were transduced with a GFP-FFluc-expressing retrovirus and purified by cell sorting. For long co-culture experiments, GFP+ Jurkat and CCRF-CEM cells were purified by single-cell sorting.

Cytotoxicity of CD5 CAR T cells was assessed via standard Cr release assays or long co-culture experiments with GFP+ target cells. In the co-culture experiments CAR T cells and target cells were plated in 96-well flat bottom plates at 1:4 or 1:2 effector-to-target ratios (target cell number was constant at 50,000) in CTL media. After 3 days of co-culture, cells were transferred to a 24-well plate with fresh media to accommodate cell expansion. Number of viable target cells was calculated with flow cytometry using CountBright counting beads (Life Technologies) and 7-AAD staining. No exogenous cytokines were added.

Sequential Killing Assay.

CD5 CAR T cells were plated with GFP+ Jurkat cells in 96-well flat bottom plates at a 1:2 effector-to-target ratio (25,000 CAR T and 50,000 Jurkat cells per well in 200 ul of CTL media without cytokines). Seventy-two hours later, cells were collected and counted with flow cytometry using CountBright counting beads and 7-AAD. CD5 CAR T cells were then replated (25,000 per well) and reconstituted with fresh Jurkat-GFP cells (50,000 per well). Cell counting and replating was repeated after 72 hours with total of 4 iterations. No exogenous cytokines were added to the culture.

Inhibition of Perforin- and FasL-Mediated Cytotoxicity.

CD5 CAR T cells were preincubated for 2 h at 37° C. in the presence of 50 nM concanamycin A (CMA) or 10 ul/ml brefeldin A (BFA), or both in 100 ul of complete CTL media per well in a 96 well flat bottom plate. Thirty minutes before the end of preincubation, anti-FasL antibody (Nok-1, LEAF purified, Biolegend) was added to a final concentration of 40 ug/ml to BFA-pretreated CAR T cells. EGTA/MgCl2 was added to CMA-pretreated cells to a final concentration of 2 mM before adding target cells (GFP+ autologous T cells, Jurkat or CCRF) at an E:T ratio 1:2. Cytotoxicity was assessed by Annexin V staining (BD Biosciences) of GFP+ target cells 2 h later and normalized to the media control. Toxicity of all inhibitors was assessed by Annexin V staining of CAR T cells and did not exceed background levels of apoptosis.

Flow Cytometry.

Anti-human CD45RA, CD45, CD62L, CD4, CD8, CD3, CD5 (clones UCHT-2 and L17F12), IFNγ and TNFα antibodies were purchased from BD Biosciences and Beckman Coulter. Anti-human CD107a was purchased from eBioscience. Intracellular cytokine staining was performed using BD Perm III buffer according to manufacturer's instructions. Protein expression of PI-9 and Bcl-2 was performed with anti-human PI-9 (ABD Serotec) and anti-Bcl-2 (BD Biosciences) antibodies using fixation and permeabilization with 100% ice cold methanol. Flow cytometric data was acquired with BC Gallios and BD LSRII cytometers and analyzed using FlowJo ver. 9 (Tree Star).

ELISpot Assay.

ELIspot analysis was used to quantitate the frequency of T cells that secreted IFN-γ in response to AdV, EBV and CMV antigens. As a positive control, ATCs were stimulated with Staphylococcal enterotoxin B (1 µg/mL; Sigma-Aldrich). Hexon and penton (Adv), IE1 and pp65 (CMV), and EBNA1, LMP1, LMP2 (EBV) pepmixes, diluted to 1 µg/mL, were used as a stimulus. Responder T cells were resuspended at $0.5-1\times10^6$/mL. Ninety-six well filtration plates (MultiScreen, #MAHAS4510, Millipore) were coated with 10 µg/mL anti-IFN-γ antibody (Catcher-mAB91-DIK, Mabtech) overnight at 4° C., then washed and blocked with CTL medium for 1 hour at 37° C. Cells were incubated for 20 hours, and the plates were washed and incubated with the secondary biotin conjugated anti-IFN-γ monoclonal antibody (Detector-mAB, 7-B6-1-Biotin; Mabtech) followed by incubation with avidin-biotinylated horseradish peroxidase complex (Vectastain Elite ABC Kit, Standard, #PK6100; Vector Laboratories) and developed with AEC substrate (Sigma-Aldrich). Plates were sent for evaluation to Zellnet Consulting. Data are plotted as spot-forming cells (SFC) versus input cell numbers.

Primary T-ALL.

De-identified frozen peripheral blood samples from T-ALL patients were thawed, rested in RPMI-1640 media supplemented with 20% FBS for 2 h and used for analysis. Low viability of cells upon thawing precluded cytotoxicity assays in all samples except #394, which was freshly processed. The protocol for collection of peripheral blood T-ALL patients was approved by the Institutional Review Board (IRB) at Baylor College of Medicine.

Mouse Xenograft Models.

Five- to seven-week-old female NOD.Cg-Prkdc$^{scid}$Il2rg$^{tm1Wjl}$/SzJ (NSG) mice (The Jackson Laboratory) were inoculated intravenously with either $3\times10^6$ Jurkat or $1\times10^6$ CCRF-CEM cells engineered to express FFluc-GFP fusion protein. Three and six days later, mice received $10\times10^6$ T cells transduced with either control (CD19) or CD5 CAR intravenously. Tumor burden was monitored by recording luminescence after injecting D-Luciferin (150 ug/kg intraperitoneally) with an IVIS Imaging system (Caliper Life Sciences). Living Image ver. 2.6 was used to visualize and calculate total luminescence. In some experiments, CAR T cells were injected on day 6 and 9 after inoculating Jurkat cells. Mice were euthanized after developing hind limb paralysis. Peripheral blood was collected by tail vein bleeding. All procedures were done in compliance with the Institutional Animal Care and Usage Committee of Baylor College of Medicine.

qPCR.

Total RNA was extracted using RNEasy Mini Plus kit (QIAgen) and cDNA was synthesized with Superscript III First-Strand Synthesis System (Invitrogen). Quantitative PCR was performed with SYBR Green Universal Mastermix (Bio-rad) using iQ5 Thermal Cycler (Bio-Rad). The following primers were used: CD5 (set 1) forward, 5'-CTCACCCGTTCCAACTCGAAG-3' (SEQ ID NO: 1) and reverse, 5'-TGGCAGACTTTTGACGCTTGA-3' (SEQ ID NO: 2); (set 2) forward, 5'-TGACCTGCTTAGAACCCCAGA-3' (SEQ ID NO: 3) and reverse, 5'-GCTGCCGCTGTAGAACTCC-3' (SEQ ID NO: 4); Bcl-2 forward, 5'-GGTGGGGTCATGTGTGTGG-3' (SEQ ID NO: 5) and reverse, 5'-CGGTTCAGGTACTCAGTCATCC-3' (SEQ ID NO: 6); Bid forward, 5'-ATGGACCGTAGCATCCCTCC-3' (SEQ ID NO: 7) and reverse, 5'-GTAGGTGCGTAGGTTCTGGT-3' (SEQ ID NO: 8); Cathepsin B forward, 5'-ACAACGTGGACATGAGCTACT-3' (SEQ ID NO: 9) and reverse, 5'-TCGGTAAACATAACTCTCTGGGG-3' (SEQ ID NO: 10); GAPDH forward, 5'-GCACCGTCAAGGCTGAGAAC-3' (SEQ ID NO: 11) and reverse, 5'-ATGGTGGTGAAGACGCCAGT-3' (SEQ ID NO: 12).

Statistical Analysis.

Unpaired 2-tailed Student's t-test was used to determine statistical significance, with P values indicated in the text and figures. Statistical analysis of the Kaplan-Meier survival curves was done using log rank (Mantel-Cox) test. Data are presented as mean±SD unless noted otherwise. All P values were calculated with Prism 6 (GraphPad).

EXAMPLE 3

Modifications of CD5 Chimeric Antigen Receptors

In particular embodiments, a CD5 CAR has modifications to one or more components of the polynucleotide encoding the CAR and/or the immune cell harboring the polynucleotide. In certain embodiments, a particular anti-CD5 scFv is utilized, including those that are not specifically listed elsewhere herein. For the intracellular signaling domains, any suitable combination may be employed, and the skilled artisan knows how to test the efficacy and safety of the combinations based on routine practices described elsewhere herein.

One CAR component that may be varied depending on the particular CD5 CAR is the spacer and/or hinge region. A spacer region links the antigen binding domain to the transmembrane domain. In specific embodiments the spacer is flexible enough to allow the antigen binding domain to orient in different directions to facilitate antigen recognition. In certain embodiments, the hinge region is from IgG1. In specific embodiments, the CH2CH3 region of immunoglobulin and portions of CD3 are utilized. The IgG4 hinge and CH3 only may be employed, in certain aspects, and in some cases the CD8a stalk is utilized.

Figure 14:
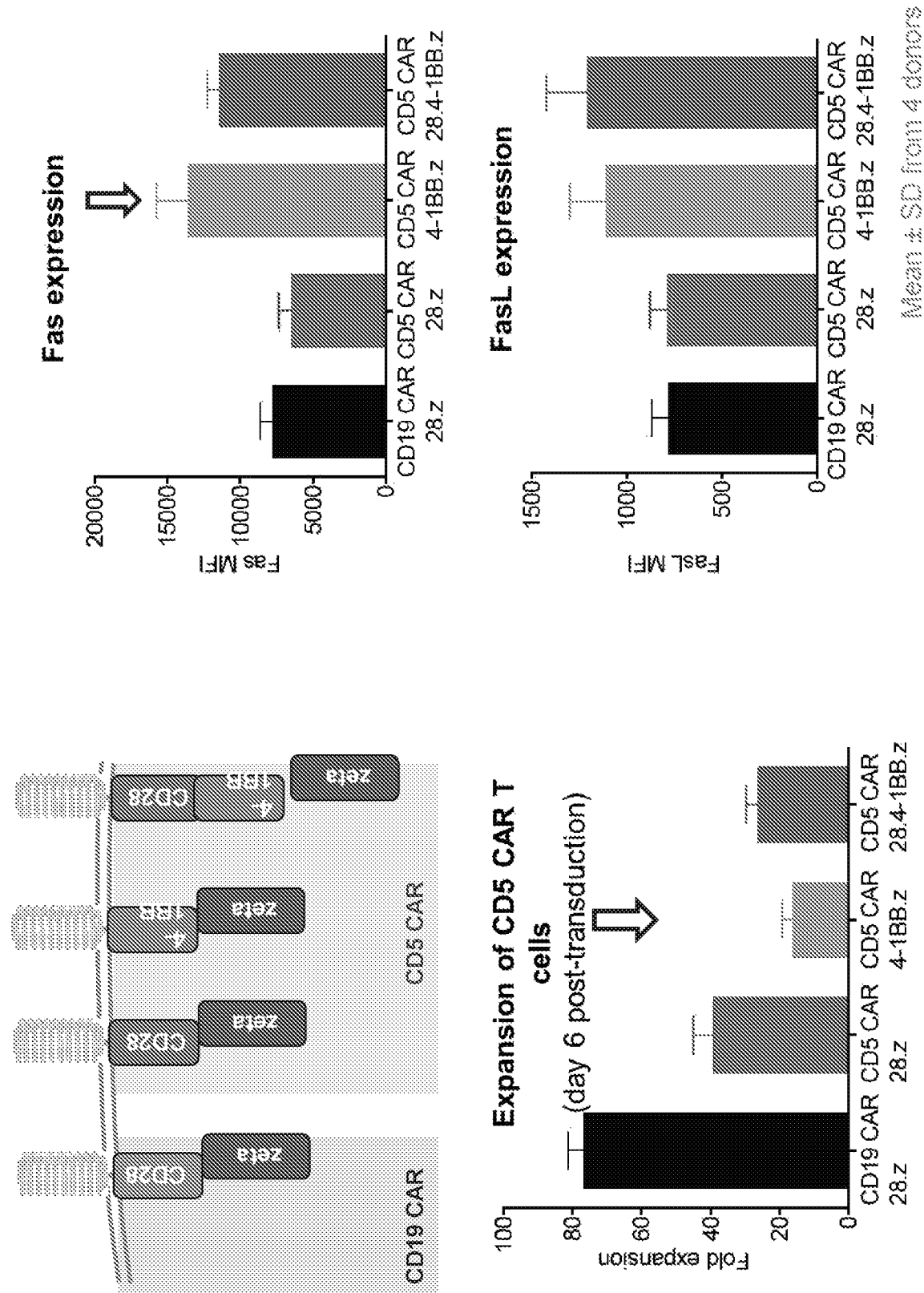

FIG. 14 shows that 4-1BB signaling enhances fratricide of CD5 CAR T cells. The bar graph on the left side of FIG. 14 shows relative expansion of T cells transduced with either control CD19 CAR or CD5 CAR containing various signaling domains (28.z, 4-1BB.z and 28.4-1BB.z) calculated at day 6 post-transduction. The bar graphs on the right shows relative expression of Fas and FasL on cell surface of CAR-transduced T cells measured by flow cytometry. Enhanced expression of Fas and FasL in 4-1BB domain-harboring T cells may contribute to enhanced fratricide. As such, it may be desirable to use a costimulatory domain other than one from 4-1BB in the construction of the CD5 chimeric antigen receptors provided herein.

Figure 15:
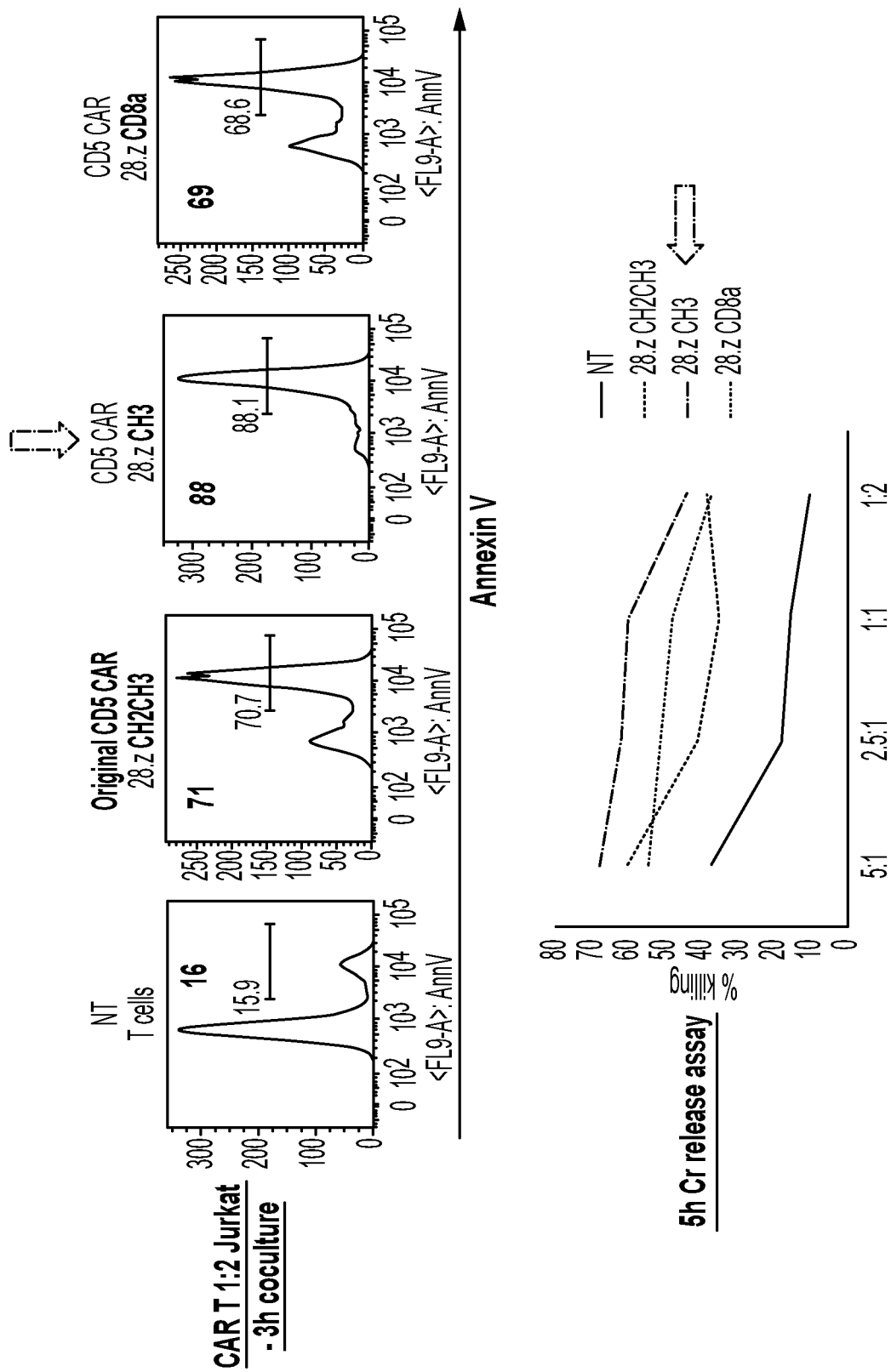
FIG. 15—Cytotoxicity tests with CD5 CARs with CH3 and CD8a spacer/hinges.

FIG. 15 demonstrates cytotoxicity tests with CD5 CARs with CH3 and CD8 α spacer/hinges. Top figure shows Annexin V staining of Jurkat cells after 3 h of coculture with either control (NT cells) or CD5 CAR containing different spacers. The graph on the bottom of FIG. 15 demonstrates cytotoxic activity of T cells expressing CD5 CAR with different spacers against Jurkat cells in a 5 hr Cr release assay. The CH3 spacer, alone, resulted in superior cell killing as compared to the CH2CH3 spacer or the CD8a spacer.

Figure 16:
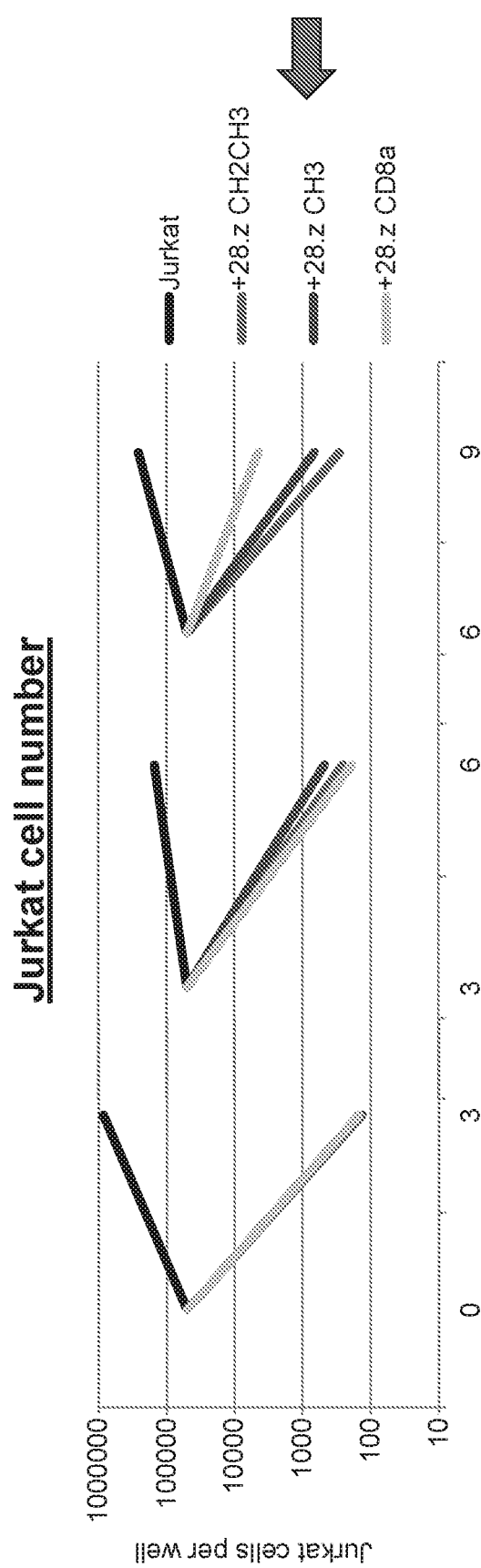
FIG. 16—Sequential killing using CD5 CARs having CH3 and CD8a spacer/hinges.

FIG. 16 shows sequential killing using CD5 CARs having CH3 and CD8 α spacer/hinges. T cells transduced with CD5 CAR containing different spacers were subjected to a sequential killing assay with Jurkat cell targets. The figure shows a decrease in target cell numbers in each iteration.

Figure 17:
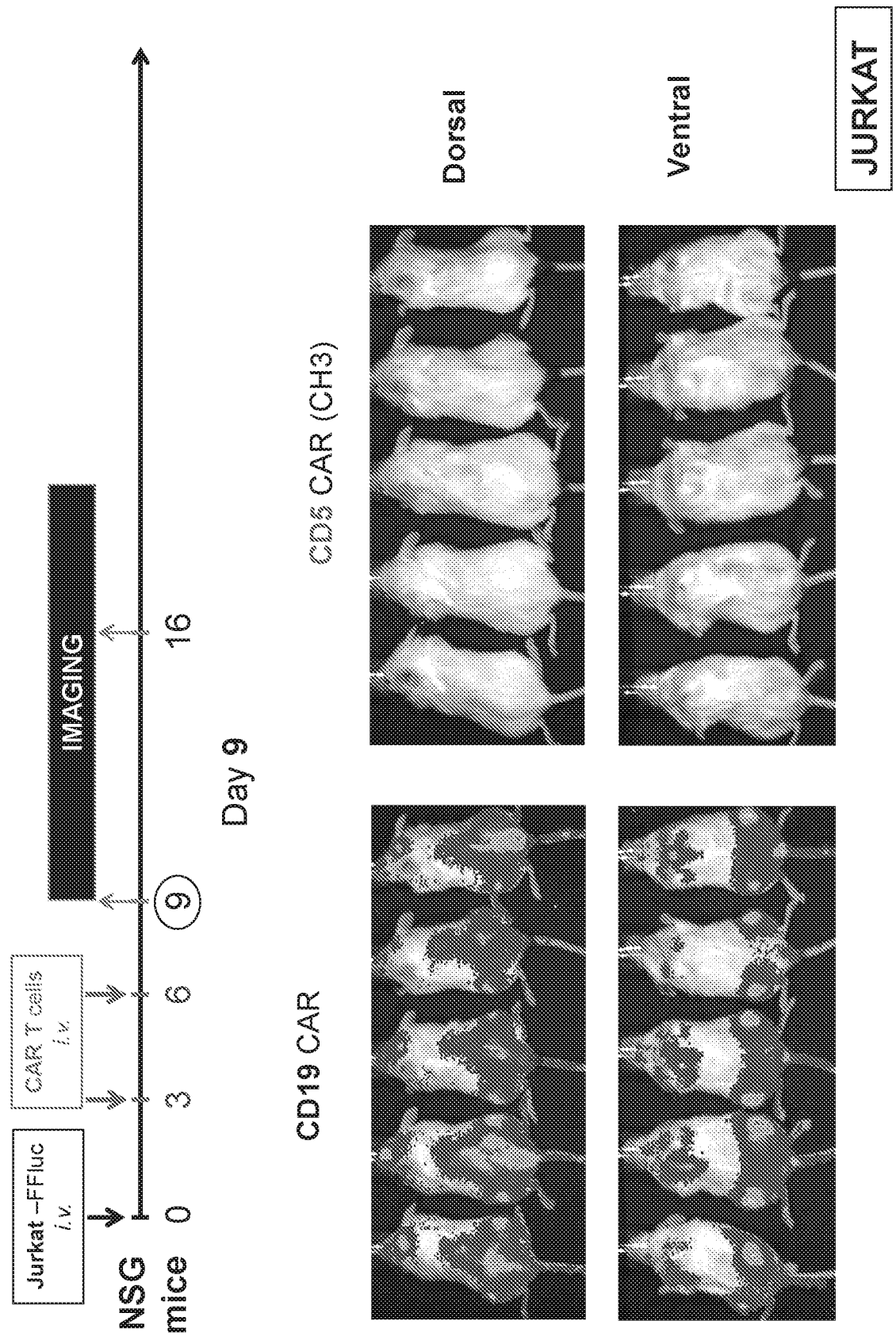
FIG. 17—Tumor burden 9 days post-implantation in vivo in a Jurkat model.

FIG. 17 demonstrates tumor burden 9 days post-implantation in vivo in a Jurkat mouse model. Tumor burden in mice from the experiment shown in FIG. 6A showing both dorsal and ventral projections on day 9 post tumor engraftment.

Figure 18:
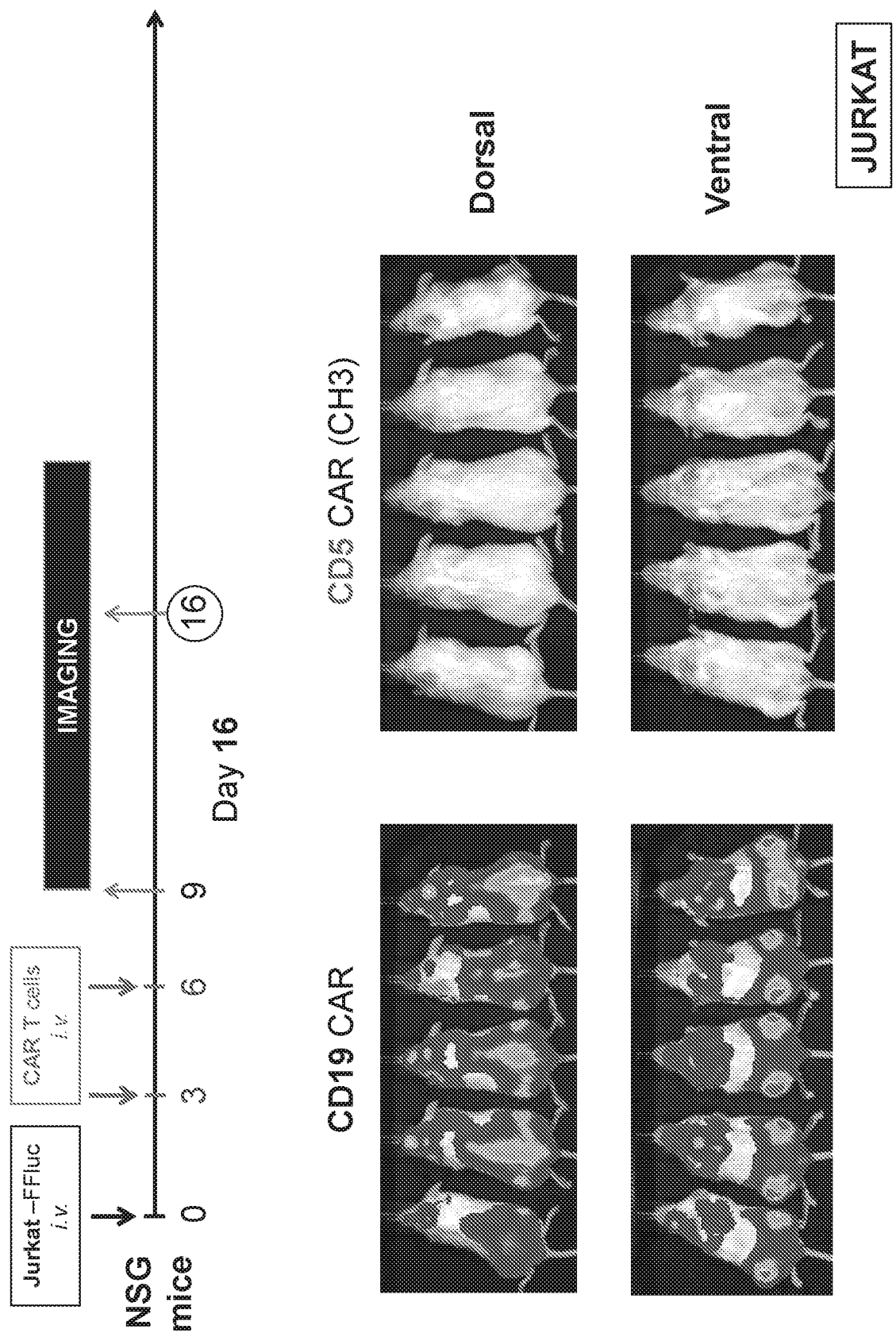
FIG. 18—Tumor burden 16 days post-implantation in vivo in a Jurkat model.

FIG. 18 demonstrates tumor burden 16 days post-implantation in vivo in a Jurkat model. Tumor burden in mice from the experiment shown in FIG. 6A showing both dorsal and ventral projections on day 16 post tumor engraftment.

Figure 19:
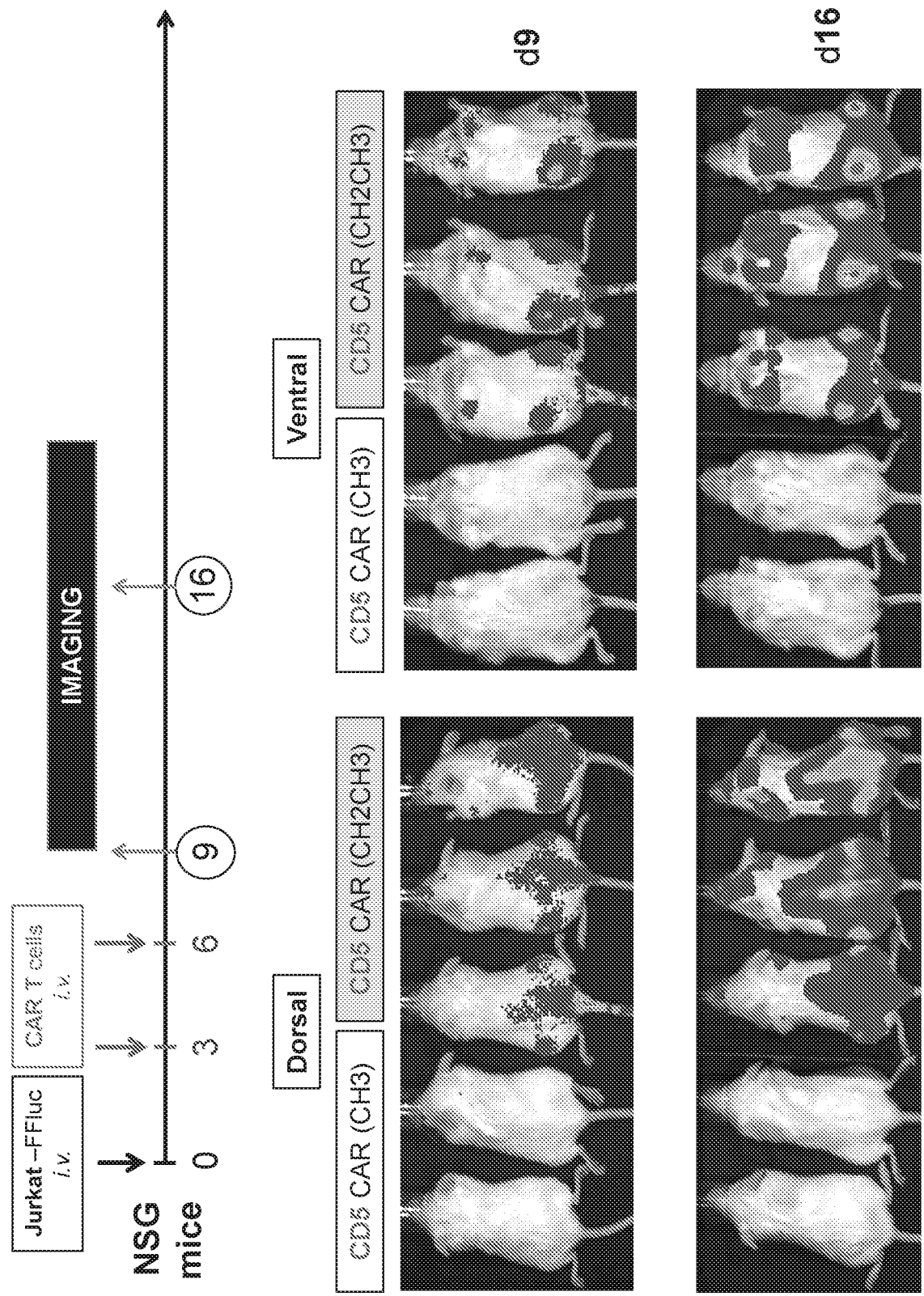
FIG. 19—Comparison of CD5 CARs having CH2CH3 hinge vs. CD5 CARs having CH3 hinge. Shading indicates the presence in the mice of Jurkat cells expressing firefly luciferase.

FIG. 19 indicates a comparison of CD5 CARs having CH2CH3 hinge vs.

CD5 CARs having CH3 hinge, including experimental design (above) and images of experimental mice. CD5 CAR T cells with either full (CH2CH3) or truncated (CH3) IgG spacer were injected to mice previously engrafted with Jurkat-FFluc cells as outlined above on day 3 and day 6 post tumor engraftment. Tumor burden in mice is shown on day 9 and day 16 demonstrating superior tumor control by T cells transduced with CD5 CAR harboring CH3 spacer.

Figure 20:
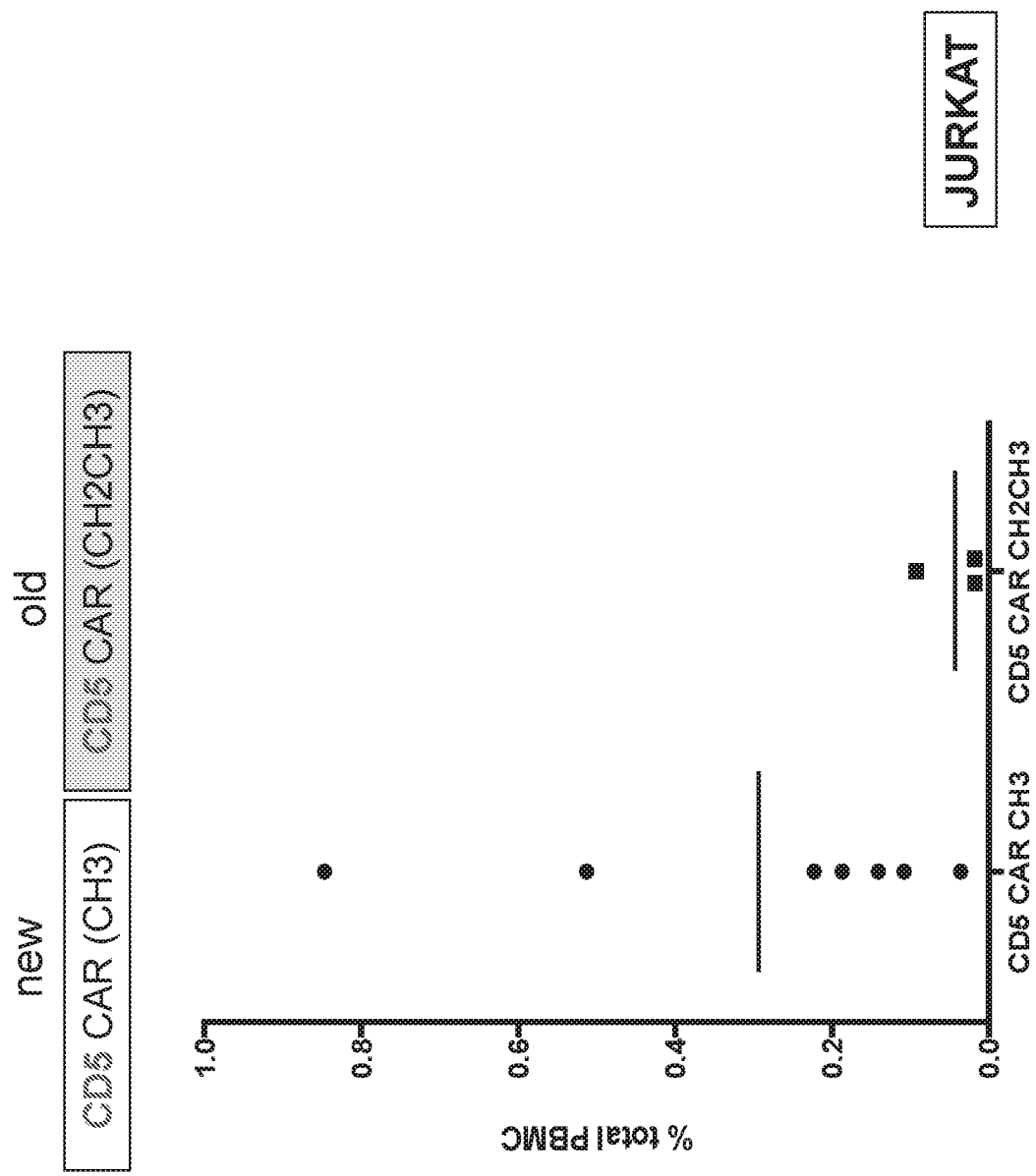
FIG. 20—Persistence of CD5 CAR T cells in blood 3 days after injection in a Jurkat model; comparison of CH2CH3 hinge vs. CH3 hinge.

FIG. 20 displays persistence of CD5 CAR T cells in blood 3 days after injection in a Jurkat model; comparison of CH2CH3 hinge vs. CH3 hinge. Mice described in FIG. 19 were subjected to tail vein bleeding 72 h after last CAR T injection. Frequency of CD5 CAR T cells in peripheral blood was measured by flow cytometry.

Figure 21:
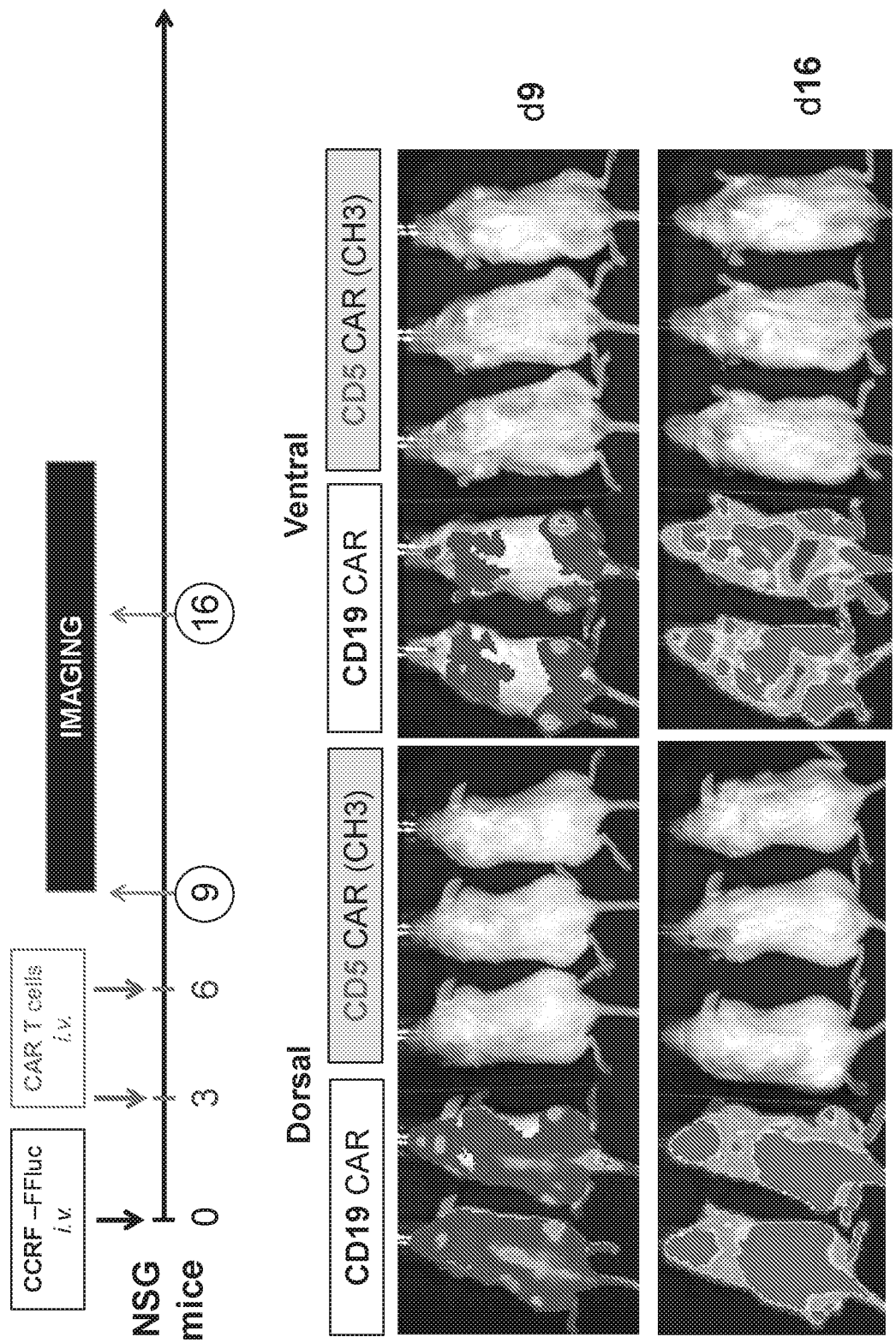
FIG. 21—Tumor burden post-implantation in a CCRF model using CD5 CARs comprising CH3 hinge.

FIG. 21 shows tumor burden post-implantation in a CCRF model using CD5 CARs comprising CH3 hinge. CCRF is an acute lymphoblastic leukemia-derived cell line. T cells transduced with either control CD19 CAR or CD5 CAR were injected to mice previously engrafted with CCRF-FFluc cells as outlined above on day 3 and day 6 post tumor engraftment. Tumor burden in mice is shown on day 9 and day 16.

Figure 22:
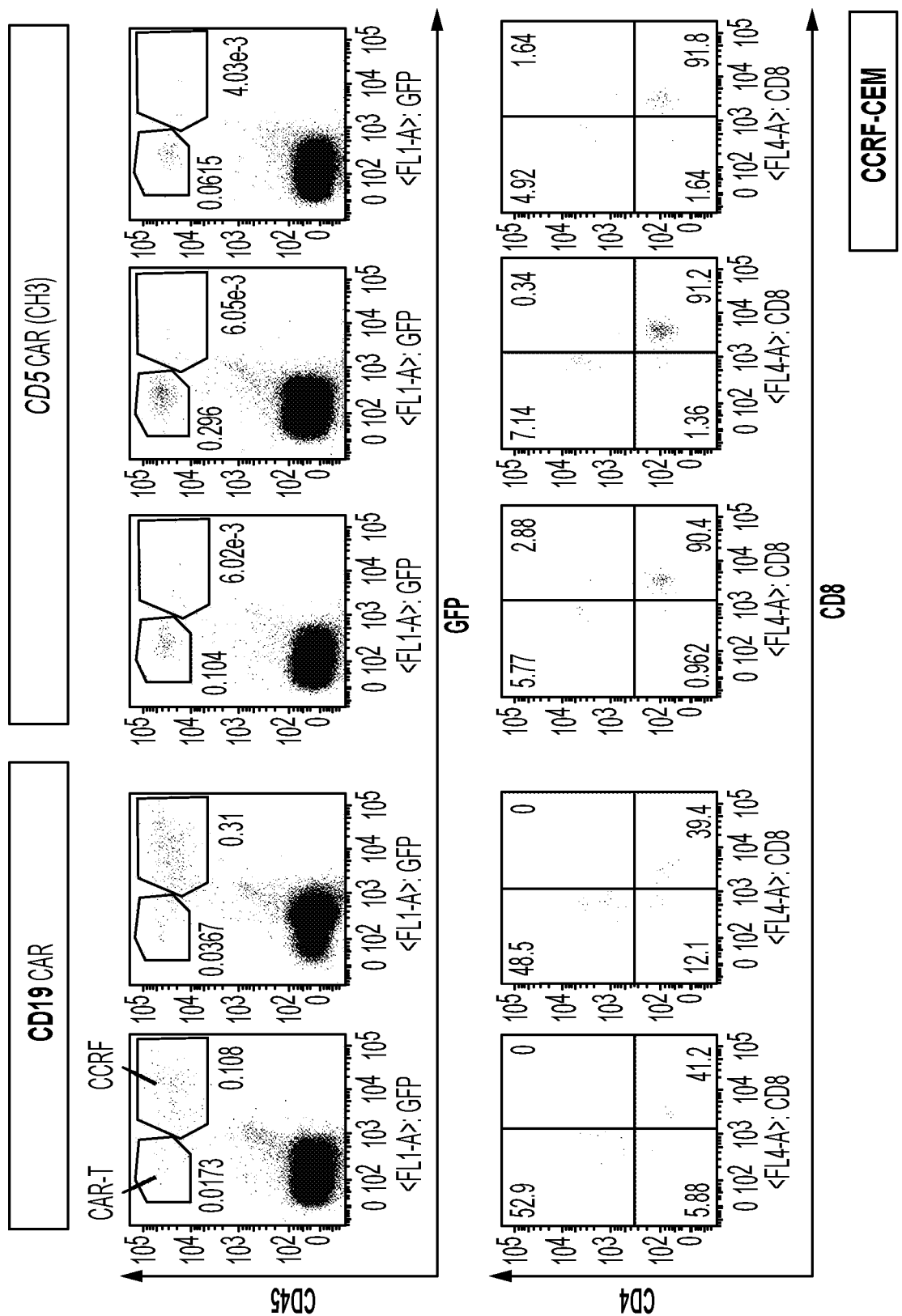
FIG. 22—CD5 CAR T cells (where CAR has a CH3 hinge) and tumor burden in blood 3 days after CAR T cell injection using a CCRF-CEM model.

FIG. 22 provides CD5 CAR T cells (where CAR has CH3 hinge) and tumor burden in blood 3 days after CAR T cell injection using a CCRF-CEM model. Relative frequency of CAR T (hCD45+ GFP−) and CCRF-CEM (hCD45+ GFP+) cells in peripheral blood of mice engrafted with CCRF-CEM and injected with CD19 CAR or CD5 CAR T cells 3 and 6 days post tumor engraftment. Peripheral blood was collected 3 days after last CAR T injection.

Figure 23:
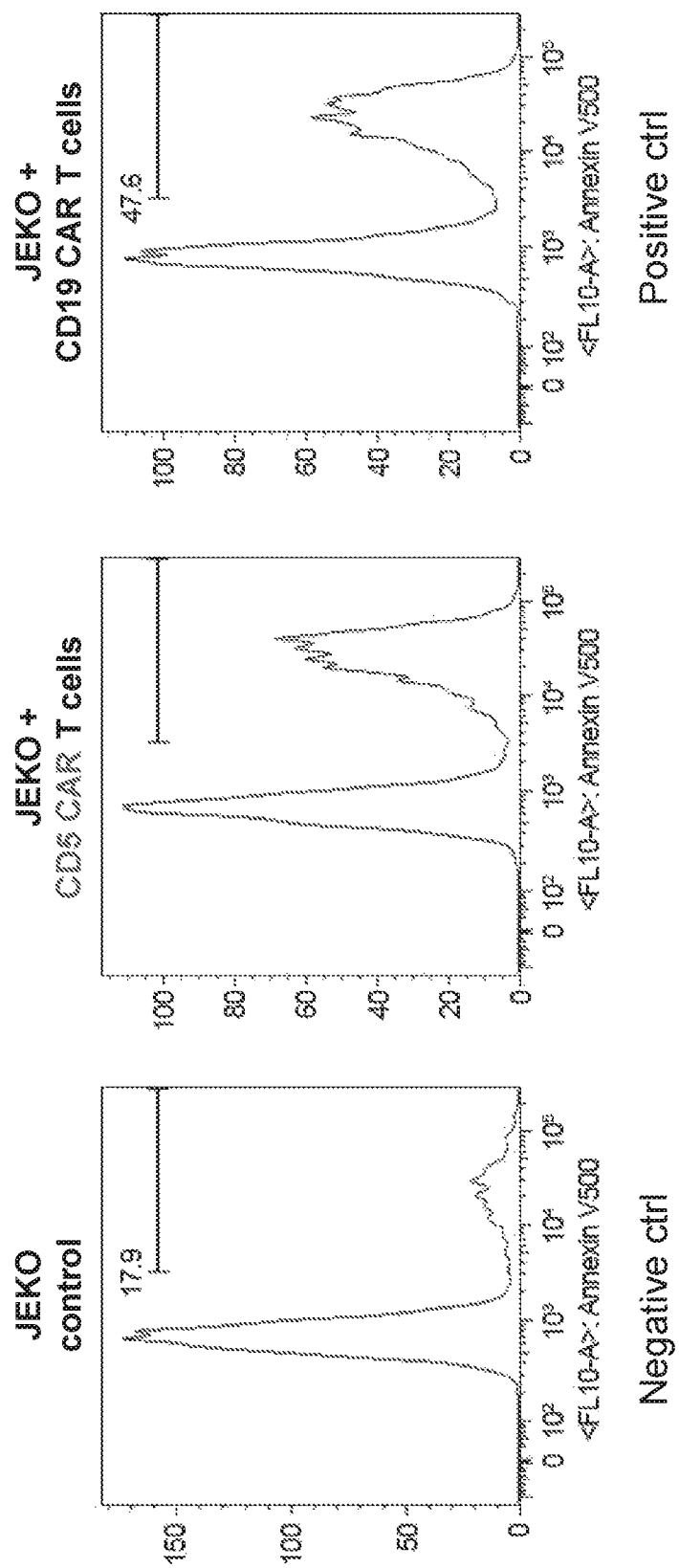
FIG. 23—CD5 CAR T cells are cytotoxic against B-CLL cell line JEKO-1.

FIG. 23 shows That CD5 CAR T cells are cytotoxic against B-CLL cell line JEKO-1. CD19 CAR T and CD5 CAR T cells were cocultured with JEKO-1 (a CD5+CD19+ B-CLL/MCL cell line) for 24 h at a 1:2 E:T ratio. Histograms show percent AnnexinV-positive (apoptotic) JEKO cells after 24 h of coculture.

What is claimed is:

1. As a composition of matter, immune cells that express a chimeric antigen receptor (CAR) that targets CD5, wherein the CAR comprises the amino acid sequence of SEQ ID NO:13 or SEQ ID NO:14.

2. The composition of claim 1, wherein the cells are T cells, NK cells, dendritic cells, or a mixture thereof.

3. The composition of claim 1, wherein the CAR is expressed from a recombinant polynucleotide.

4. The composition of claim 3, wherein the polynucleotide further comprises a suicide gene, a cytokine, an additional CAR, a cytokine receptor, or a chimeric cytokine receptor.

5. The composition of claim 1, wherein the immune cells comprise a polynucleotide that comprises a suicide gene, a cytokine, an additional CAR, a cytokine receptor, or a chimeric cytokine receptor, wherein said polynucleotide is a different molecule than the polynucleotide that expresses the CAR that targets CD5.

6. The composition of claim 1, wherein the CAR comprises a co-stimulatory molecule endodomain selected from the group consisting of CD28, CD27, 4-1BB, OX40, ICOS, and a combination thereof.

7. The composition of claim 1, wherein the CAR comprises a co-stimulatory molecule endodomain that is not 4-1BB.

8. The composition of claim 4, wherein the additional CAR is an activating CAR or an inhibitory CAR.

9. The composition of claim 2, wherein said T cells are CD4+ T cells.

10. The composition of claim 2, wherein said T cells are CD8+ T cells.

11. The composition of claim 2, wherein said T cells are Treg cells.

12. The composition of claim 1, wherein the CAR comprises one or more scFvs, in addition to an scFV comprised in SEQ ID NO:13 or SEQ ID NO:14.

13. The composition of claim 12, wherein the one or more scFvs in addition to the scFv comprised in SEQ ID NO:13 or SEQ ID NO:14 targets CD19, CD20, CD22, Kappa or light chain, Glypican-3, CD30, CD33, CD123, CD38, ROR1, ErbB2, ErbB3/4, EGFR VIII, carcinoembryonic antigen, EGP2, EGP40, mesothelin, TAG72, PSMA, NKG2D ligands, B7-H6, IL-13 receptor α2, IL-11 receptor R α, MUC1, MUC16, CA9, GD2, GD3, HMW-MAA, CD171, Lewis Y, G250/CAIX, HLA-AI MAGE A1, HLA-A2 NY-ESO-1, PSC1, folate receptor-α, CD44v7/8, 8H9, NCAM, VEGF receptors, 5T4, Fetal AchR, NKG2D ligands, CD44v6 or CD7.

14. The composition of claim 1, wherein the CAR comprises a transmembrane domain selected from the group consisting of CD3-zeta, CD28, CD8α, CD4, or a combination thereof.

15. The composition of claim 1, wherein the CAR comprises a spacer derived from IgG CH3 without the CH2 domain.

16. The composition of claim 1, wherein the spacer is derived from CD8α.

17. The composition of claim 1, wherein the CAR comprises amino acid sequence of SEQ ID NO:14.

18. The composition of claim 1, wherein the CAR comprises the amino acid sequence of SEQ ID NO:13.

19. The composition of claim 1, wherein the CAR comprises a CD5scFv, a leader sequence, a CH2+CH3 IgG1 spacer, a hinge, CD28 transmembrane domain, CD28 co-stimulatory endodomain, and CD3zeta.

* * * * *

SEQUENCE LISTING

```
<160> NUMBER OF SEQ ID NOS: 17

<210> SEQ ID NO 1
<211> LENGTH: 21
<212> TYPE: DNA
<213> ORGANISM: Artificial Sequence
<220> FEATURE:
<223> OTHER INFORMATION: Synthetic Primer

<400> SEQUENCE: 1
ctcacccgtt ccaactcgaa g                                          21

<210> SEQ ID NO 2
<211> LENGTH: 21
<212> TYPE: DNA
<213> ORGANISM: Artificial Sequence
<220> FEATURE:
<223> OTHER INFORMATION: Synthetic Primer

<400> SEQUENCE: 2
tggcagactt ttgacgcttg a                                          21

<210> SEQ ID NO 3
<211> LENGTH: 21
<212> TYPE: DNA
<213> ORGANISM: Artificial Sequence
<220> FEATURE:
<223> OTHER INFORMATION: Synthetic Primer

<400> SEQUENCE: 3
tgacctgctt agaaccccag a                                          21

<210> SEQ ID NO 4
<211> LENGTH: 19
<212> TYPE: DNA
<213> ORGANISM: Artificial Sequence
<220> FEATURE:
<223> OTHER INFORMATION: Synthetic Primer

<400> SEQUENCE: 4
gctgccgctg tagaactcc                                             19

<210> SEQ ID NO 5
<211> LENGTH: 19
<212> TYPE: DNA
<213> ORGANISM: Artificial Sequence
<220> FEATURE:
<223> OTHER INFORMATION: Synthetic Primer

<400> SEQUENCE: 5
ggtggggtca tgtgtgtgg                                             19
```

<210> SEQ ID NO 6
<211> LENGTH: 22
<212> TYPE: DNA
<213> ORGANISM: Artificial Sequence
<220> FEATURE:
<223> OTHER INFORMATION: Synthetic Primer

<400> SEQUENCE: 6
cggttcaggt actcagtcat cc                                    22

<210> SEQ ID NO 7
<211> LENGTH: 20
<212> TYPE: DNA
<213> ORGANISM: Artificial Sequence
<220> FEATURE:
<223> OTHER INFORMATION: Synthetic Primer

<400> SEQUENCE: 7
atggaccgta gcatccctcc                                       20

<210> SEQ ID NO 8
<211> LENGTH: 20
<212> TYPE: DNA
<213> ORGANISM: Artificial Sequence
<220> FEATURE:
<223> OTHER INFORMATION: Synthetic Primer

<400> SEQUENCE: 8
gtaggtgcgt aggttctggt                                       20

<210> SEQ ID NO 9
<211> LENGTH: 21
<212> TYPE: DNA
<213> ORGANISM: Artificial Sequence
<220> FEATURE:
<223> OTHER INFORMATION: Synthetic Primer

<400> SEQUENCE: 9
acaacgtgga catgagctac t                                     21

<210> SEQ ID NO 10
<211> LENGTH: 23
<212> TYPE: DNA
<213> ORGANISM: Artificial Sequence
<220> FEATURE:
<223> OTHER INFORMATION: Synthetic Primer

<400> SEQUENCE: 10
tcggtaaaca taactctctg ggg                                   23

<210> SEQ ID NO 11
<211> LENGTH: 20
<212> TYPE: DNA
<213> ORGANISM: Artificial Sequence
<220> FEATURE:
<223> OTHER INFORMATION: Synthetic Primer

<400> SEQUENCE: 11
gcaccgtcaa ggctgagaac                                       20

<210> SEQ ID NO 12
<211> LENGTH: 20
<212> TYPE: DNA
<213> ORGANISM: Artificial Sequence
<220> FEATURE:

<223> OTHER INFORMATION: Synthetic Primer

<400> SEQUENCE: 12
atggtggtga agacgccagt                                                    20

<210> SEQ ID NO 13
<211> LENGTH: 686
<212> TYPE: PRT
<213> ORGANISM: Homo sapiens

<400> SEQUENCE: 13

Met Glu Phe Gly Leu Ser Trp Leu Phe Leu Val Ala Ile Leu Lys Gly
1               5                   10                  15

Val Gln Cys Ile Asp Ala Met Gly Asn Ile Gln Leu Val Gln Ser Gly
            20                  25                  30

Pro Glu Leu Lys Lys Pro Gly Glu Thr Val Lys Ile Ser Cys Lys Ala
        35                  40                  45

Ser Gly Tyr Thr Phe Thr Asn Tyr Gly Met Asn Trp Val Lys Gln Ala
    50                  55                  60

Pro Gly Lys Gly Leu Arg Trp Met Gly Trp Ile Asn Thr His Thr Gly
65                  70                  75                  80

Glu Pro Thr Tyr Ala Asp Asp Phe Lys Gly Arg Phe Ala Phe Ser Leu
                85                  90                  95

Glu Thr Ser Ala Ser Thr Ala Tyr Leu Gln Ile Asn Asn Leu Lys Asn
            100                 105                 110

Glu Asp Thr Ala Thr Tyr Phe Cys Thr Arg Arg Gly Tyr Asp Trp Tyr
        115                 120                 125

Phe Asp Val Trp Gly Ala Gly Thr Thr Val Thr Val Ser Ser Gly Gly
    130                 135                 140

Gly Gly Ser Gly Gly Gly Gly Ser Gly Gly Gly Gly Ser Asp Ile Lys
145                 150                 155                 160

Met Thr Gln Ser Pro Ser Ser Met Tyr Ala Ser Leu Gly Glu Arg Val
                165                 170                 175

Thr Ile Thr Cys Lys Ala Ser Gln Asp Ile Asn Ser Tyr Leu Ser Trp
            180                 185                 190

Phe His His Lys Pro Gly Lys Ser Pro Lys Thr Leu Ile Tyr Arg Ala
        195                 200                 205

Asn Arg Leu Val Asp Gly Val Pro Ser Arg Phe Ser Gly Ser Gly Ser
    210                 215                 220

Gly Gln Asp Tyr Ser Leu Thr Ile Ser Ser Leu Asp Tyr Glu Asp Met
225                 230                 235                 240

Gly Ile Tyr Tyr Cys Gln Gln Tyr Asp Glu Ser Pro Trp Thr Phe Gly
                245                 250                 255

Gly Gly Thr Lys Leu Glu Met Lys Gly Ser Gly Asp Pro Ala Glu Pro
            260                 265                 270

Lys Ser Pro Asp Lys Thr His Thr Cys Pro Pro Cys Pro Ala Pro Glu
        275                 280                 285

Leu Leu Gly Gly Pro Ser Val Phe Leu Phe Pro Pro Lys Pro Lys Asp
    290                 295                 300

Thr Leu Met Ile Ser Arg Thr Pro Glu Val Thr Cys Val Val Val Asp
305                 310                 315                 320

Val Ser His Glu Asp Pro Glu Val Lys Phe Asn Trp Tyr Val Asp Gly
                325                 330                 335

Val Glu Val His Asn Ala Lys Thr Lys Pro Arg Glu Glu Gln Tyr Asn
            340                 345                 350

Ser Thr Tyr Arg Val Val Ser Val Leu Thr Val Leu His Gln Asp Trp
            355                 360                 365

Leu Asn Gly Lys Glu Tyr Lys Cys Lys Val Ser Asn Lys Ala Leu Pro
        370                 375                 380

Ala Pro Ile Glu Lys Thr Ile Ser Lys Ala Lys Gly Gln Pro Arg Glu
385                 390                 395                 400

Pro Gln Val Tyr Thr Leu Pro Pro Ser Arg Asp Glu Leu Thr Lys Asn
                405                 410                 415

Gln Val Ser Leu Thr Cys Leu Val Lys Gly Phe Tyr Pro Ser Asp Ile
            420                 425                 430

Ala Val Glu Trp Glu Ser Asn Gly Gln Pro Glu Asn Asn Tyr Lys Thr
        435                 440                 445

Thr Pro Pro Val Leu Asp Ser Asp Gly Ser Phe Phe Leu Tyr Ser Lys
    450                 455                 460

Leu Thr Val Asp Lys Ser Arg Trp Gln Gln Gly Asn Val Phe Ser Cys
465                 470                 475                 480

Ser Val Met His Glu Ala Leu His Asn His Tyr Thr Gln Lys Ser Leu
                485                 490                 495

Ser Leu Ser Pro Gly Lys Lys Asp Pro Lys Phe Trp Val Leu Val Val
            500                 505                 510

Val Gly Gly Val Leu Ala Cys Tyr Ser Leu Leu Val Thr Val Ala Phe
        515                 520                 525

Ile Ile Phe Trp Val Arg Ser Lys Arg Ser Arg Leu Leu His Ser Asp
    530                 535                 540

Tyr Met Asn Met Thr Pro Arg Arg Pro Gly Pro Thr Arg Lys His Tyr
545                 550                 555                 560

Gln Pro Tyr Ala Pro Pro Arg Asp Phe Ala Ala Tyr Arg Ser Arg Val
                565                 570                 575

Lys Phe Ser Arg Ser Ala Asp Ala Pro Ala Tyr Gln Gln Gly Gln Asn
            580                 585                 590

Gln Leu Tyr Asn Glu Leu Asn Leu Gly Arg Arg Glu Glu Tyr Asp Val
        595                 600                 605

Leu Asp Lys Arg Arg Gly Arg Asp Pro Glu Met Gly Gly Lys Pro Arg
    610                 615                 620

Arg Lys Asn Pro Gln Glu Gly Leu Tyr Asn Glu Leu Gln Lys Asp Lys
625                 630                 635                 640

Met Ala Glu Ala Tyr Ser Glu Ile Gly Met Lys Gly Glu Arg Arg Arg
                645                 650                 655

Gly Lys Gly His Asp Gly Leu Tyr Gln Gly Leu Ser Thr Ala Thr Lys
            660                 665                 670

Asp Thr Tyr Asp Ala Leu His Met Gln Ala Leu Pro Pro Arg
        675                 680                 685

<210> SEQ ID NO 14
<211> LENGTH: 270
<212> TYPE: PRT
<213> ORGANISM: Homo sapiens

<400> SEQUENCE: 14

Met Glu Phe Gly Leu Ser Trp Leu Phe Leu Val Ala Ile Leu Lys Gly
1               5                   10                  15

Val Gln Cys Ile Asp Ala Met Gly Asn Ile Gln Leu Val Gln Ser Gly
            20                  25                  30

Pro Glu Leu Lys Lys Pro Gly Glu Thr Val Lys Ile Ser Cys Lys Ala

```
            35                  40                  45
Ser Gly Tyr Thr Phe Thr Asn Tyr Gly Met Asn Trp Val Lys Gln Ala
 50                  55                  60

Pro Gly Lys Gly Leu Arg Trp Met Gly Trp Ile Asn Thr His Thr Gly
65                  70                  75                  80

Glu Pro Thr Tyr Ala Asp Asp Phe Lys Gly Arg Phe Ala Phe Ser Leu
                85                  90                  95

Glu Thr Ser Ala Ser Thr Ala Tyr Leu Gln Ile Asn Asn Leu Lys Asn
            100                 105                 110

Glu Asp Thr Ala Thr Tyr Phe Cys Thr Arg Arg Gly Tyr Asp Trp Tyr
        115                 120                 125

Phe Asp Val Trp Gly Ala Gly Thr Thr Val Thr Val Ser Ser Gly Gly
    130                 135                 140

Gly Gly Ser Gly Gly Gly Gly Ser Gly Gly Gly Gly Ser Asp Ile Lys
145                 150                 155                 160

Met Thr Gln Ser Pro Ser Ser Met Tyr Ala Ser Leu Gly Glu Arg Val
                165                 170                 175

Thr Ile Thr Cys Lys Ala Ser Gln Asp Ile Asn Ser Tyr Leu Ser Trp
            180                 185                 190

Phe His His Lys Pro Gly Lys Ser Pro Lys Thr Leu Ile Tyr Arg Ala
        195                 200                 205

Asn Arg Leu Val Asp Gly Val Pro Ser Arg Phe Ser Gly Ser Gly Ser
    210                 215                 220

Gly Gln Asp Tyr Ser Leu Thr Ile Ser Ser Leu Asp Tyr Glu Asp Met
225                 230                 235                 240

Gly Ile Tyr Tyr Cys Gln Gln Tyr Asp Glu Ser Pro Trp Thr Phe Gly
                245                 250                 255

Gly Gly Thr Lys Leu Glu Met Lys Gly Ser Gly Asp Pro Ala
            260                 265                 270

<210> SEQ ID NO 15
<211> LENGTH: 236
<212> TYPE: PRT
<213> ORGANISM: Homo sapiens

<400> SEQUENCE: 15

Glu Pro Lys Ser Pro Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140
```

-continued

```
Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys Lys Asp Pro Lys
225                 230                 235

<210> SEQ ID NO 16
<211> LENGTH: 68
<212> TYPE: PRT
<213> ORGANISM: Homo sapiens

<400> SEQUENCE: 16

Phe Trp Val Leu Val Val Gly Gly Val Leu Ala Cys Tyr Ser Leu
1               5                   10                  15

Leu Val Thr Val Ala Phe Ile Ile Phe Trp Val Arg Ser Lys Arg Ser
                20                  25                  30

Arg Leu Leu His Ser Asp Tyr Met Asn Met Thr Pro Arg Arg Pro Gly
            35                  40                  45

Pro Thr Arg Lys His Tyr Gln Pro Tyr Ala Pro Pro Arg Asp Phe Ala
        50                  55                  60

Ala Tyr Arg Ser
65

<210> SEQ ID NO 17
<211> LENGTH: 112
<212> TYPE: PRT
<213> ORGANISM: Homo sapiens

<400> SEQUENCE: 17

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
                20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
        50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
            85                  90                  95

Thr Lys Asp Thr Tyr Asp Ala Leu His Met Gln Ala Leu Pro Pro Arg
        100                 105                 110
```